United States Patent
Al-Ali et al.

(10) Patent No.: US 12,004,881 B2
(45) Date of Patent: *Jun. 11, 2024

(54) AUTOMATED CONDITION SCREENING AND DETECTION

(71) Applicant: Masimo Corporation, Irvine, CA (US)

(72) Inventors: Ammar Al-Ali, San Juan Capistrano, CA (US); Bilal Muhsin, Irvine, CA (US); Omar Ahmed, Lake Forest, CA (US); Jad Adel Wafeeq, Mission Viejo, CA (US); Fahad Abdulrahman Alaql, Riyadh (SA); Keith Ward Indorf, Lake Elsinore, CA (US)

(73) Assignee: Masimo Corporation, Irvine, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 17/451,409

(22) Filed: Oct. 19, 2021

(65) Prior Publication Data

US 2022/0031254 A1 Feb. 3, 2022

Related U.S. Application Data

(60) Continuation of application No. 16/442,268, filed on Jun. 14, 2019, now Pat. No. 11,172,890, which is a
(Continued)

(51) Int. Cl.
*A61B 5/00* (2006.01)
*A61B 5/02* (2006.01)
(Continued)

(52) U.S. Cl.
CPC ........ *A61B 5/7275* (2013.01); *A61B 5/02028* (2013.01); *A61B 5/0205* (2013.01);
(Continued)

(58) Field of Classification Search
CPC ... A61B 5/0002; A61B 5/0205; A61B 5/1455; A61B 5/14551; A61B 5/14552;
(Continued)

(56) References Cited

U.S. PATENT DOCUMENTS

| 4,869,253 A | 9/1989 | Craig, Jr. et al. |
| 4,960,128 A | 10/1990 | Gordon et al. |

(Continued)

FOREIGN PATENT DOCUMENTS

WO WO 2013/103885 7/2013

OTHER PUBLICATIONS

U.S. Appl. No. 16/425,706, Automated CCHD Screening and Detection, filed May 29, 2019.
(Continued)

*Primary Examiner* — Chu Chuan Liu
(74) *Attorney, Agent, or Firm* — Knobbe, Martens, Olson & Bear, LLP

(57) ABSTRACT

Embodiments are disclosed that enable an electronic device to instruct as user how to user one or more noninvasive sensors to measure one or more physiological parameters of a patient. In one embodiment, the measured parameters are used to obtain a diagnosis, such as a diagnosis of a critical congenital heart defect.

20 Claims, 39 Drawing Sheets

Related U.S. Application Data continuation-in-part of application No. 15/681,256, filed on Aug. 18, 2017, now Pat. No. 10,729,384, which is a continuation-in-part of application No. 15/279,134, filed on Sep. 28, 2016, now Pat. No. 10,278,648, which is a continuation of application No. 15/195,037, filed on Jun. 28, 2016, now Pat. No. 10,349,898, which is a division of application No. 13/733,782, filed on Jan. 3, 2013, now Pat. No. 9,392,945.

(60) Provisional application No. 62/685,834, filed on Jun. 15, 2018, provisional application No. 61/703,132, filed on Sep. 19, 2012, provisional application No. 61/583,143, filed on Jan. 4, 2012.

(51) Int. Cl.

| | | |
|---|---|---|
| *A61B 5/0205* | (2006.01) | |
| *A61B 5/0295* | (2006.01) | |
| *A61B 5/1455* | (2006.01) | |
| *A61B 5/024* | (2006.01) | |
| *A61B 5/08* | (2006.01) | |

(52) U.S. Cl.
CPC ........ *A61B 5/0295* (2013.01); *A61B 5/14551* (2013.01); *A61B 5/14552* (2013.01); *A61B 5/6825* (2013.01); *A61B 5/6829* (2013.01); *A61B 5/684* (2013.01); *A61B 5/7221* (2013.01); *A61B 5/7278* (2013.01); *A61B 5/7282* (2013.01); *A61B 5/743* (2013.01); *A61B 5/024* (2013.01); *A61B 5/0816* (2013.01); *A61B 2503/04* (2013.01)

(58) Field of Classification Search
CPC ... A61B 5/0022; A61B 5/6829; A61B 5/7278; A61B 5/02028; A61B 5/7282; A61B 5/7221; A61B 5/7275; A61B 5/684; A61B 5/743; A61B 5/0295; A61B 5/6825; A61B 5/024; A61B 5/0816
See application file for complete search history.

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,050,613 A | 9/1991 | Newman et al. |
| 5,069,213 A | 12/1991 | Hink et al. |
| 5,078,714 A | 1/1992 | Katims |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,398,682 A | 3/1995 | Lynn |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,277 A | 8/1999 | Mortz |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,083,172 A | 7/2000 | Baker, Jr. et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,321,110 B1 | 11/2001 | Ito et al. |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |

(56) References Cited

U.S. PATENT DOCUMENTS

| | | |
|---|---|---|
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,829,378 B2 | 12/2004 | DiFilippo et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |

(56) References Cited

U.S. PATENT DOCUMENTS

| | | |
|---|---|---|
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,824 B1 | 5/2011 | Kayyali et al. |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |

(56) References Cited

U.S. PATENT DOCUMENTS

| | | |
|---|---|---|
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |

(56) References Cited

U.S. PATENT DOCUMENTS

| | | |
|---|---|---|
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |

(56) References Cited

U.S. PATENT DOCUMENTS

| | | |
|---|---|---|
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,588,518 B2 | 3/2020 | Kiani |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,729,384 B2 | 8/2020 | Al-Ali et al. |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,172,890 B2 | 11/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Ai-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |

(56) References Cited

U.S. PATENT DOCUMENTS

| | | |
|---|---|---|
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 11,872,156 B2 | 1/2024 | Telfort et al. |
| 11,879,960 B2 | 1/2024 | Ranasinghe et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0034293 A1 | 2/2004 | Kimball |
| 2004/0097797 A1 | 5/2004 | Porges et al. |
| 2004/0106163 A1 | 6/2004 | Workman, Jr. et al. |
| 2005/0055276 A1 | 3/2005 | Kiani et al. |
| 2005/0165316 A1 | 7/2005 | Lowery |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0276632 A1 | 11/2007 | Banet et al. |
| 2007/0282478 A1 | 12/2007 | Al-Ali et al. |
| 2008/0009754 A1 | 1/2008 | Chang |
| 2008/0064965 A1 | 3/2008 | Jay et al. |
| 2008/0071155 A1 | 3/2008 | Kiani |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2008/0221464 A1 | 9/2008 | Al-Ali |
| 2009/0036759 A1 | 2/2009 | Ault et al. |
| 2009/0062664 A1 | 3/2009 | Chang et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004035 A1 | 1/2010 | Ray et al. |
| 2010/0004518 A1 | 1/2010 | Vo et al. |
| 2010/0016690 A1 | 1/2010 | Watson et al. |
| 2010/0030040 A1 | 2/2010 | Poeze et al. |
| 2010/0079279 A1 | 4/2010 | Watson et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0001605 A1 | 1/2011 | Kiani et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0215560 A1* | 8/2012 | Ofek .................. G16H 70/20 705/3 |
| 2012/0226117 A1 | 9/2012 | Lamego et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0296183 A1 | 11/2012 | Kinsley et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0018241 A1 | 8/2013 | Bezzerides et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0073880 A1 | 3/2014 | Boucher et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |

(56) References Cited

U.S. PATENT DOCUMENTS

| | | |
|---|---|---|
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0324579 A1* | 11/2015 | Qian .................. G06F 21/45 726/6 |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224216 A1 | 8/2017 | Al-Ali |
| 2017/0224231 A1 | 8/2017 | Al-Ali |
| 2017/0224233 A1 | 8/2017 | Al-Ali |
| 2017/0224262 A1 | 8/2017 | Al-Ali |
| 2017/0228516 A1 | 8/2017 | Sampath et al. |
| 2017/0231537 A1 | 8/2017 | Al-Ali |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2018/0008146 A1 | 1/2018 | Al-Ali et al. |

(56) References Cited

U.S. PATENT DOCUMENTS

| | | |
|---|---|---|
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0192965 A1* | 7/2018 | Rose ............... A61B 5/0002 |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0274635 A1 | 9/2019 | Al-Ali et al. |
| 2019/0298270 A1 | 10/2019 | Al-Ali et al. |
| 2019/0320906 A1 | 10/2019 | Olsen |
| 2019/0374139 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |

(56) References Cited

U.S. PATENT DOCUMENTS

| | | |
|---|---|---|
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |

OTHER PUBLICATIONS

U.S. Appl. No. 16/442,268, Automated Condition Screening and Detection, filed Jun. 14, 2019.

U.S. Appl. No. 16/818,855, Congenital Heart Disease Monitor, filed Mar. 13, 2020.

Granelli et al., "Screening for duct-dependent congenital heart disease with pulse oximetry: A critical evaluation of strategies to maximize sensitivity", Acta Paediatrica, 2005; 94:1590-1596, http://ww.masimo.com/pdf/Granelli_Article.pdf., 1 page downloaded and printed from the World Wide Web.

Hoke et al., "Oxygen Saturation as a Screening Test for Critical Ongenital Heart Disease: A Preliminary Study", Pediatric Cardiology, vol. 23, 2002, pp. 403-409.

International Search Report and Written Opinion received in PCT Application No. PCT/US2013/020377 dated Apr. 17, 2013 in 13 pages.

International Preliminary Report on Patentability and Written Opinion received in PCT Application No. PCT/US2013/020377 dated Jul. 17, 2014 in 8 pages.

Kemper et al., "Strategies for Implementing Screening for Critical Congenital Heart Disease", Pediatrics, Nov. 2011, vol. 128, No. 5, pp. e1259-e1267.

Koppel et al., "Effective of Pulse Oximetry Screening for Congenital Heart Disease in Asymptomatic Newborns", Pediatrics, 2003, vol. 111, No. 3, 451-455.

"Newborn Screening for CCHD, Answers and Resources for Primary Care Pediatricians", American Academy of Pediatrics, http://www.aap.org/en-us/advocacy-and-policy/aap-health-initiatives/, printed on Jun. 6, 2017, in 8 pages.

"Tools and Technology to Start Your CCHD Screening Program", Masimo Corporation, 2010-2011, in 16 pages.

"User Interface Elements", http://www.usabilit.gov/how-to-and-tools/methods/user-interface-elements.html, printed on Jun. 19, 2017, in 7 pages.

U.S. Appl. No. 16/425,706, Automated CCHD Screening and Detection, filed Nov. 23, 2021.

U.S. Appl. No. 16/911,799, Automated Condition Screening and Detection, filed Nov. 16, 2021.

U.S. Appl. No. 16/818,855, Congenital Heart Disease Monitor, filed Mar. 21, 2023.

U.S. Appl. No. 16/911,799, Automated Condition Screening and Detection, filed Jun. 25, 2020.

U.S. Appl. No. 18/184,262, Congenital Heart Disease Monitor, filed Mar. 15, 2023.

* cited by examiner

Step 1: Pre-Ductal Instruction

Step 2: Pre-Ductal Instruction

Step 2: Sensor Error

Step 3: Post-Ductal Instruction

Step 4: Post-Ductal Measure

Step 4: Sensor Error

FIG. 14A

Step 5: CCHD Screen Results: Pass step 5: screening results

| first screen | 05-13-2012 | 05:42am |
| --- | --- | --- |
| pre-ductal ⓘ | 96% SpO$_2$ | 1.7PI |
| post-ductal ⓘ | 95% SpO$_2$ | 1.8PI |
| Δ SpO$_2$ difference ⓘ | 1% | |

(close)

negative screen: "pass" result
screen conplete

Step 5: CCHD Screen Results: Conditional Fail (1)

step 5: screening results

| first screen | 05-13-2012 | 05:42am |
| --- | --- | --- |
| pre-ductal ⓘ | 96% SpO$_2$ | 1.7PI |
| post-ductal ⓘ | 91% SpO$_2$ | 1.8PI |
| Δ SpO$_2$ difference ⓘ | 5% | |

(close)

positive screen: post-ductal SpO$_2$
less than 95%
perform second screen in one hour

Step 5: CCHD Screen Results: Conditional Fail (2)

step 5: screening results

| first screen | 05-13-2012 | 06:42am |
| --- | --- | --- |
| pre-ductal ⓘ | 96% SpO$_2$ | 1.7PI |
| post-ductal ⓘ | 91% SpO$_2$ | 1.8PI |
| Δ SpO$_2$ difference ⓘ | 5% | |

(close)

positive screen: post-ductal SpO$_2$
less than 95%
perform third screen in one hour

Step 5: CCHD Screen Results: Fail (3)

step 5: screening results

| first screen | 05-13-2012 | 07:42am |
| --- | --- | --- |
| pre-ductal ⓘ | 96% SpO$_2$ | 1.7PI |
| post-ductal ⓘ | 91% SpO$_2$ | 1.8PI |
| Δ SpO$_2$ difference ⓘ | 5% | |

(close)

positive screen: difference greater than 3%
rerer newborn for further medical evaluation

1460 →
1465 →

AUTOMATED CONDITION SCREENING AND DETECTION

INCORPORATION BY REFERENCE TO ANY RELATED APPLICATIONS

This application is a continuation of U.S. patent application Ser. No. 16/442,268, filed Jun. 14, 2019, and titled "AUTOMATED CONDITION SCREENING AND DETECTION", which application is a continuation-in-part of U.S. patent application Ser. No. 15/681,256, filed Aug. 18, 2017, and titled "AUTOMATED CONDITION SCREENING AND DETECTION", which application is a continuation-in-part of U.S. patent application Ser. No. 15/279,134, filed Sep. 28, 2016, and titled "AUTOMATED CCHD SCREENING AND DETECTION", which application is a continuation of U.S. patent application Ser. No. 15/195,037, filed Jun. 28, 2016, and titled "AUTOMATED CCHD SCREENING AND DETECTION", which application is a divisional of U.S. patent application Ser. No. 13/733,782, filed Jan. 3, 2013, and titled "AUTOMATED CCHD SCREENING AND DETECTION", which application claims a priority benefit under 35 U.S.C. § 119 to U.S. Provisional Patent Application No. 61/583,143, filed Jan. 4, 2012, and titled "SYSTEMS AND METHODS AUTOMATING CCHD SCREENING AND DETECTION", and U.S. Provisional Patent Application No. 61/703,132, filed Sep. 19, 2012, and titled "SYSTEMS AND METHODS AUTOMATING CCHD SCREENING AND DETECTION". Additionally, U.S. patent application Ser. No. 16/442,268, filed Jun. 14, 2019, and titled "AUTOMATED CONDITION SCREENING AND DETECTION", claims a priority benefit under 35 U.S.C. § 119 to U.S. Provisional Patent Application No. 62/685,834, filed Jun. 15, 2018, and titled "AUTOMATED CONDITION SCREENING AND DETECTION". The entire disclosure of each of the above items is hereby made part of this specification as if set forth fully herein and incorporated by reference for all purposes, for all that it contains.

Any and all applications, if any, for which a foreign or domestic priority claim is identified in the Application Data Sheet of the present application are hereby incorporated by reference under 37 CFR 1.57.

BACKGROUND

Pulse oximetry screening can identify some critical congenital heart defects ("CCHDs"), which also are known collectively in some instances as critical congenital heart disease. CCHDs are structural heart defects that often are associated with hypoxia among infants during the newborn period. Infants with CCHDs are at risk for significant morbidity or mortality. There are several defects that could be considered CCHDs. However, in the context of newborn pulse oximetry screening at the time of preparation of the present application, the Centers for Disease Control and Prevention ("CDC") for the U.S. government classify seven (7) defects as CCHD: hypoplastic left heart syndrome, pulmonary atresia (with intact septum), tetralogy of Fallot, total anomalous pulmonary venous return, transposition of the great arteries, tricuspid atresia, and truncus arteriosus. According to the CDC, these seven CCHDs represent about seventeen to about thirty one percent (17-31%) of all congenital heart disease.

Patent ductus arteriosus ("PDA") is common in infants with several or more of the above seven (7) defects. In the developing fetus, the ductus arteriosus ("DA") 102 shown in FIG. 1 is the vascular connection between the pulmonary artery 106 and the aortic arch 104 that allows most of the blood from the right ventricle 110 to bypass the fetus' fluid-filled compressed lungs. During fetal development, this shunt protects the right ventricle 110 from pumping against the high resistance in the lungs 108, which can lead to right ventricular failure if the DA 102 closes in-utero.

When the newborn takes its first breath, the lungs open and pulmonary vascular resistance decreases. In normal newborns, the DA is substantially closed within twelve to twenty four (12-24) hours after birth, and is completely sealed after three (3) weeks.

In the case of PDA, high pressure oxygenated blood from the aorta 104 leaks or flows back into the pulmonary artery 112 and back to the lungs 108 with normal deoxygenated venous blood. The additional fluid returning to the lungs increases lung pressure to the point that the infant may have greater difficulty inflating the lungs. This uses more calories than normal and often interferes with feeding in infancy. Moreover, an open (patent) DA 102 alters the flow in the descending aorta 118, which, as a result, changes the blood oxygen saturation in the feet.

Without screening, some newborns with CCHDs might be missed because the signs of CCHD might not be evident before an infant is discharged from the hospital after birth. Other heart defects might be considered secondary screening targets. Some of these heart defects can be just as severe as the primary screening targets and also require intervention soon after birth. These secondary targets include aortic arch atresia or hypoplasia, interrupted aortic arch, coarctation of the aorta, double-outlet right ventricle, Ebstein anomaly, pulmonary stenosis, atrioventricular septal defect, ventricular septal defect, and single ventricle defects (other than hypoplastic left heart syndrome and tricuspid atresia).

Current CDC recommendations focus on screening infants in the well-baby nursery and in intermediate care nurseries or other units in which discharge from the hospital is common during an infant's first week of life. At the time of preparation of the present application, the CDC promulgated a CCHD screening process 200 reproduced as FIG. 2, directed toward oxygen saturation measurements, or percentages measured using, for example, a standard pulse oximeter.

According to the CDC's CCHD screening process 200 of FIG. 2, a screen is considered positive (see box 228) if (1) any oxygen saturation measurement is less than ninety percent (<90%) (in the initial screen or in repeat screens) (see boxes 206, 214, and 222); (2) the oxygen saturation measurement is less than ninety five percent (<95%) in the right hand and foot on three measures (see boxes 208, 216, and 224), each separated by one (1) hour (see boxes 204, 212, 220); or (3) a greater than three percent (>3%) absolute difference exists in oxygen saturation measurements between the right hand and foot on three measures (see boxes 208, 216, and 224), each separated by one (1) hour. Any screening that is greater than or equal to ninety five percent (≥95%) in the right hand or foot with a less than or equal to three percent (≤3%) absolute difference in oxygen saturation measurements between the right hand and foot is considered a negative screen and screening would end (see boxes 210, 218, 226, and 230).

The CDC recommends any infant receiving a positive screen receive a diagnostic echocardiogram, which would involve an echocardiogram within the hospital or birthing center, transport to another institution for the procedure, or use of telemedicine for remote evaluation. This can be expensive, disruptive, and possibly harmful to the infant.

For example, at the time of preparation of the present application, an echocardiogram to verify an out-of-range (positive) screen could cost several hundred dollars.

Thus, false positives are to be avoided. The CDC believes that false positives are decreased if the infant is alert, and timing pulse oximetry screening around the time of newborn hearing screening improves efficiency.

Pulse oximetry screening may not detect all CCHDs, so it is possible for a baby with a negative screening result to still have a CCHD or other congenital heart defect.

SUMMARY OF CERTAIN EMBODIMENTS

In certain embodiments, a system for noninvasively measuring a physiological parameter of a patient to facilitate a diagnosis can include an electronic device having a display, a wireless transceiver, a memory device having processor-executable instruction stored thereon, and a hardware processor in communication with the display, wireless transceiver, and the memory. The hardware processor can be programmed to execute the processor-executable instructions stored in the memory so as to display, on the display, a request for at least one patient ID associated with a patient; receive an input including the at least one patient ID; validate the at least on patient ID using one or more validations rules; provide, on the display, instructions for obtaining a critical congenital heart defect (CCHD) screening of the patient; determine CCHD screening information; and transmit the CCHD screening information in association with the at least one patient ID to a gateway computing device.

The system of the preceding paragraph can be implemented together with any combination of the following features, among others: the hardware processor is programmed to execute the processor-executable instructions stored in the memory so as to further display, on the display, instructions to obtain a first measurement by positioning a first noninvasive sensor at a first measurement site on a patient; the hardware processor is programmed to execute the processor-executable instructions stored in the memory so as to further receive, from the noninvasive sensor, first signals responsive to a first physiological characteristic of the patient; the hardware processor is programmed to execute the processor-executable instructions stored in the memory so as to further calculate a first measured physiological parameter responsive to the first signals; the hardware processor is programmed to execute the processor-executable instructions stored in the memory so as to further display, on the display, instructions to obtain a second measurement by positioning a second noninvasive sensor at a second measurement site on the patient; the hardware processor is programmed to execute the processor-executable instructions stored in the memory so as to further receive, from the second noninvasive sensor, second signals responsive to a second physiological characteristic of the patient; the hardware processor is programmed to execute the processor-executable instructions stored in the memory so as to further calculate a second measured physiological parameter of the patient responsive to the second signals; the hardware processor is programmed to execute the processor-executable instructions stored in the memory so as to further display, on the display, the first and second measured physiological parameters; wherein the validation rules are configurable; wherein the hardware processor is programmed to execute the processor-executable instructions stored in the memory so as to further in response to determining that the at least one patient ID is not valid based on the validation rules, provide a notification to a user; wherein the hardware processor is programmed to execute the processor-executable instructions stored in the memory so as to further allow the user to bypass the notification; wherein the gateway computing device is configured to transmit the CCHD screening information in association with the at least one patient ID to a data aggregator/translator computing device; wherein the gateway computing device is further configured provide communications among a plurality of patient devices and the data aggregator/translator computing device; wherein the hardware processor is programmed to execute the processor-executable instructions stored in the memory so as to further in response to receiving, from the gateway computing device, a message indicating a need to re-screen a patient for CCHD, display a notification; wherein message is received via the data aggregator/translator computing device, and wherein at least one of the gateway computing device or the data aggregator/translator computing device determines the message is to be provided to the system; wherein the data aggregator/translator computing device is configured to deduplicate patient data received from the gateway computing device; wherein the data aggregator/translator computing device is configured to transmit the CCHD screening information in association with the at least one patient ID to an electronic medical record (EMR) system; wherein the data aggregator/translator computing device is further configured to aggregate patient data from a plurality of gateway computing devices.

In certain embodiments, a system for noninvasively measuring a physiological parameter of a patient to facilitate a diagnosis can include an electronic device having a display, a wireless transceiver, a memory device having processor-executable instruction stored thereon, and a hardware processor in communication with the display, wireless transceiver, and the memory. The hardware processor can be programmed to execute the processor-executable instructions stored in the memory so as to display, on the display, instructions to obtain a first measurement by positioning a first noninvasive sensor at a first measurement site on a patient; receive, from the noninvasive sensor, first signals responsive to a first physiological characteristic of the patient; calculate a first measured physiological parameter responsive to the first signals; display, on the display, instructions to obtain a second measurement by positioning a second noninvasive sensor at a second measurement site on the patient; receive, from the second noninvasive sensor, second signals responsive to a second physiological characteristic of the patient; calculate a second measured physiological parameter of the patient responsive to the second signals; display, on the display, the first and second measured physiological parameters; transmit, with the wireless transceiver, the first and second measured parameters over a network to a clinician; and initiate, with the wireless transceiver, a telemedicine session with the clinician over the network to obtain a diagnosis based on the first and second measured parameters.

The system of the preceding paragraph can be implemented together with any combination of the following features, among others: the first measured parameter can be oxygen saturation and the second measured parameter can be blood pressure; the wireless transceiver can be configured to receive an instruction to re-run one or both of the first and second measurements; the hardware processor can be further configured to output a selection of clinicians, receive a selection of one of the clinicians from the patient, and initiate a communication session with the clinician; wherein the telemedicine session comprises a video of the clinician;

wherein the hardware processor can be further configured to receive an indication of a prescription; wherein the hardware processor can be further configured to instruct the patient to take a temperature reading; wherein the hardware processor can be further configured to instruct the patient to perform the first measurement again due to low signal confidence in the first measurement.

In other embodiments, a system for noninvasively measuring a physiological parameter of a patient to facilitate a diagnosis can include an electronic device in communication with a noninvasive sensor coupled with a patient. The electronic device can be configured to drive light sources of the noninvasive sensor and to receive output signals from the noninvasive sensor. The electronic device can include a hardware processor that can process the output signals from the noninvasive sensor to measure a physiological parameter associated with the patient; determine, based on a level of the physiological parameter, that critical congenital heart defect (CCHD) screening is recommended; transmit a notification that the CCHD screening is recommended; and subsequent to said transmission of the notification, and in response to receipt of an indication that CCHD screening is to be performed: display, on a display of the electronic device, instructions to position the noninvasive sensor at a first measurement site on the patient; obtain, with the noninvasive sensor, first physiological data from the first measurement site; display, on the display of the electronic device, instructions to position the noninvasive sensor at a second measurement site on the patient; obtain, with the noninvasive sensor, second physiological data from the second measurement site; process the first physiological data and said second physiological data; and output a difference between said first physiological data and the second physiological data, the difference used to determine the existence of a CCHD.

The system of the preceding paragraph can be implemented together with any combination of the following features, among others: the hardware processor can be further configured to determine, based on the level of the physiological parameter, that critical congenital heart defect (CCHD) screening is recommended by determining that oxygen saturation is below a threshold level; the first physiological data can include a first window of physiological data, the second physiological data can include a second window of physiological data, and the first window and the second window can be non-overlapping in time. Further, the hardware processor can be further configured to process said first physiological data and said second physiological data by: calculating a plurality of first physiological parameter values corresponding to the first window; calculating a plurality of second physiological parameter values corresponding to the second window; determining first confidence values corresponding to the first physiological parameter values; determining second confidence values corresponding to the second physiological parameter values; selecting a first selected physiological parameter value from the first physiological parameter values, the first selected physiological parameter value having a highest value of the first confidence values; selecting a second selected physiological parameter value from the second physiological parameter values, the second selected physiological parameter value having a highest value of the second confidence values; and calculating the difference between the first selected physiological parameter value and the second selected physiological parameter value.

Moreover, the systems of the preceding paragraphs can be implemented together with any combination of the following features, among others: the hardware processor can be further configured to output an indication that the first and second selected physiological parameter values were selected to calculate the difference; the hardware processor can be further configured to output an indication that the first and second selected physiological parameter values were selected to calculate the difference due to the first and second selected physiological parameter values having the highest values of the first and second confidence values; the hardware processor can be further configured to display, on the display, a configuration option that enables a clinician to specify a recommended period of time between CCHD screenings; the hardware processor can be further configured to perform one or both of the following: display an indication recommending the CCHD screening, or transmit, over a network, an indication recommending the CCHD screening; the hardware processor can be further configured to display the first and second physiological parameter values, together with a third physiological parameter value, used in determining to recommend the CCHD screening; the hardware processor can be further configured to display, on the display, whether results of the CCHD screening were sent to an electronic medical record; and the hardware processor can be further configured to display, on the display, an option to send the results of the CCHD screening to the electronic medical record.

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the systems and/or computer systems to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

For purposes of summarizing the disclosure, certain aspects, advantages and novel features thereof have been described herein. Of course, it is to be understood that not necessarily all such aspects, advantages or features will be embodied in any particular embodiment of the invention.

BRIEF DESCRIPTION OF THE DRAWINGS

The following drawings and the associated descriptions are provided to illustrate embodiments of the present disclosure and do not limit the scope of the claims.

FIGS. 12A-C, 13A-C, and 14A-D illustrate example screen shots, including instructions for single sensor operation, of a pulse oximeter monitor configured for measuring CCHD, according to an embodiment of the present disclosure.

DETAILED DESCRIPTION

Overview

In one embodiment, automated critical congenital heart defect ("CCHD") screening systems and processes are described. A caregiver may be guided to use a single or dual sensor pulse oximeter to obtain pre- and post-ductal blood oxygenation measurements. A delta of the measurements indicates the possible existence or nonexistence of a CCHD. Errors in the measurements are reduced by a configurable measurement confidence threshold based on, for example, a perfusion index. Measurement data may be stored and retrieved from a remote data processing center for repeated screenings.

Figure 2:
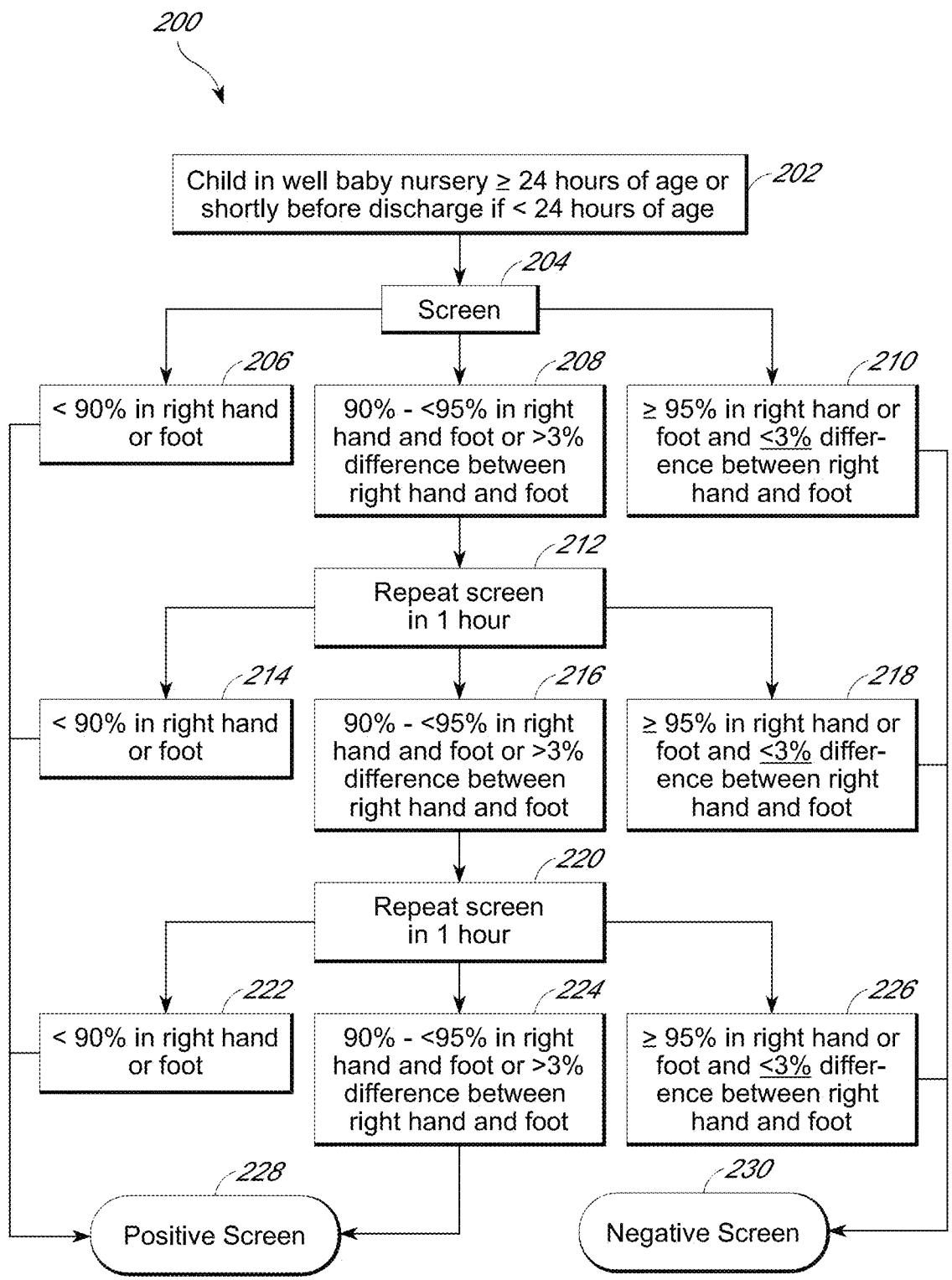
FIG. 2 illustrates an embodiment of a CCHD screening process provided by the CDC.

The CCHD screening process of FIG. 2 incorporates multiple measurement sites, such as, for example, a baseline site of the right hand and a secondary site of the feet or left hand. In some cases, a stereo pulse oximeter, such as the one disclosed in U.S. Pat. No. 6,334,065 (the '065 Patent), incorporated by reference herein, could use two (2) or more of its associated sensors, one for each of multiple sites to accomplish the measurements. In fact, the '065 Patent discusses the use of its sensor for multiple sites to determine indications of PDA, Persistent Pulmonary Hypertension in Neonates ("PPHN"), and Aortic Coarctation. However, very few if any institutions possess stereo pulse oximeters.

Rather, in most if not all circumstances, the CCHD screening process of FIG. 2 will be implemented on a single site pulse oximeter. The caregiver will apply the sensor to the first site, such as the baseline right hand, and take measurements. The caregiver will then remove the sensor from the first site, and transfer it to the second site, such as a foot, left hand, etc. and take measurements. As shown in FIG. 2, the CCHD screening process relies on the delta (or difference) between the two measurements.

Drawbacks may occur using the single sensor implementation. For example, there will be a time differential between the first baseline measurement and the second alternate site measurement when the caregiver changes sites. In infants, the parameters measureable with today's oximeters, including but not limited to oxygen saturation ("$SpO_2$"), vary within relatively short periods. This is exacerbated when infants are exited, crying, or otherwise agitated.

In the most straightforward scenario where the $SpO_2$ measurements are somewhat varying, the single sensor implementation of CCHD screening may determine, for example, an infant's $SpO_2$ during a valley or trough of varying $SpO_2$ values for the baseline measurement, and quite accidentally during a peak of varying $SpO_2$ values for the alternate measurement. Such time displaced measurements could appear anywhere on an infant's $SpO_2$ waveform. Thus, the differential between the baseline measurement and the alternate measurement, which is the key to determining positive or negative screenings under the CCHD screening process, could be subject to error. This is exacerbated as the CCHD screening process may require three (3) or more screenings before rendering a conclusion. Thus, a screening process may include measurements taken under different data conditions at each screen, and then again across the screens.

To overcome these and other drawbacks, the present disclosure includes systems and methods automating CCHD screening and detection. In an embodiment, a processor executes one or more processing modules to improve a likelihood that during a single sensor implementation of CCHD screening, the measurement values while time displaced, correspond to data conditions similar to one another. In addition, the processing module may determine the best sites for measurements.

In an embodiment, an oximeter or communicating monitor controls and tracks the implementation of the screening process, including instructions to caregivers on next steps. For example, a straightforward instruction may include "Attach Sensor to Right Hand," "Attach Sensor to Alternate Site," "Attach Sensor to Right Foot," "Attach Sensor to Left Foot," "Calm Patient," "Adjust Sensor Positioning," or the like. The oximeter may also include a quality indicator providing information on the confidence in the screening measurements. A quality measure may be included for each measurement, for the entire screen, or the like. For example, the display may indicate "Positive Screen, 72% Confidence." In an embodiment, a minimum confidence threshold may be used to instruct a caregiver to repeat the measurements and/or restart the screening process. Moreover, the oximeter may produce an audio/visual alarm indicating time for a repeat screen, may accept patient information including a patient identifier, and the like.

In other embodiments, the oximeter may communicate with a host digital network or system to store or upload measurement data associated with a unique identifier to a remote processing center. That network or system may include multiple networks or systems. However, the oximeter may access previously stored information, such as, for example, earlier screening data stored at the remote network, to complete or increment the CCHD screening process. In an embodiment, a first network may be an institutional network such as a hospital data system, a cellular or other data system, or the like, wirelessly communicating with the oximeter or monitor. The system or systems eventually allow communication to a remote data server or processing center that stores the measurement information in a manner that provides for retrieval and appropriate association with newly acquired data.

Embodiments of the present disclosure generally relates to systems and methods automating critical congenital heart defects ("CCHDs") screening and detection. In an embodiment, the CCHD screening process may be implemented on a single site pulse oximeter. A caregiver will apply the pulse oximeter sensor to the first site, such as the right hand, and take baseline measurements including, for example, blood oxygen saturation ("SpO$_2$"). The caregiver will then remove the pulse oximeter sensor from the first site, and transfer it to the second site, such as, for example, a foot or left hand, and take measurements. As shown in FIG. 2, and as described above, the CCHD screening process relies on the delta (or difference) between the two measurements. Then, a processor executes one or more processing modules to improve a likelihood that during a single sensor implementation of CCHD screening, the measurement values, while time displaced, correspond to data conditions similar to one another. In addition, the processing module may determine the best sites for measurements.

As used herein, the terms pulse oximeter, CCHD screening system, CCHD measurement device, and CCHD monitor may be used interchangeably.

Example Embodiments

Figure 1:
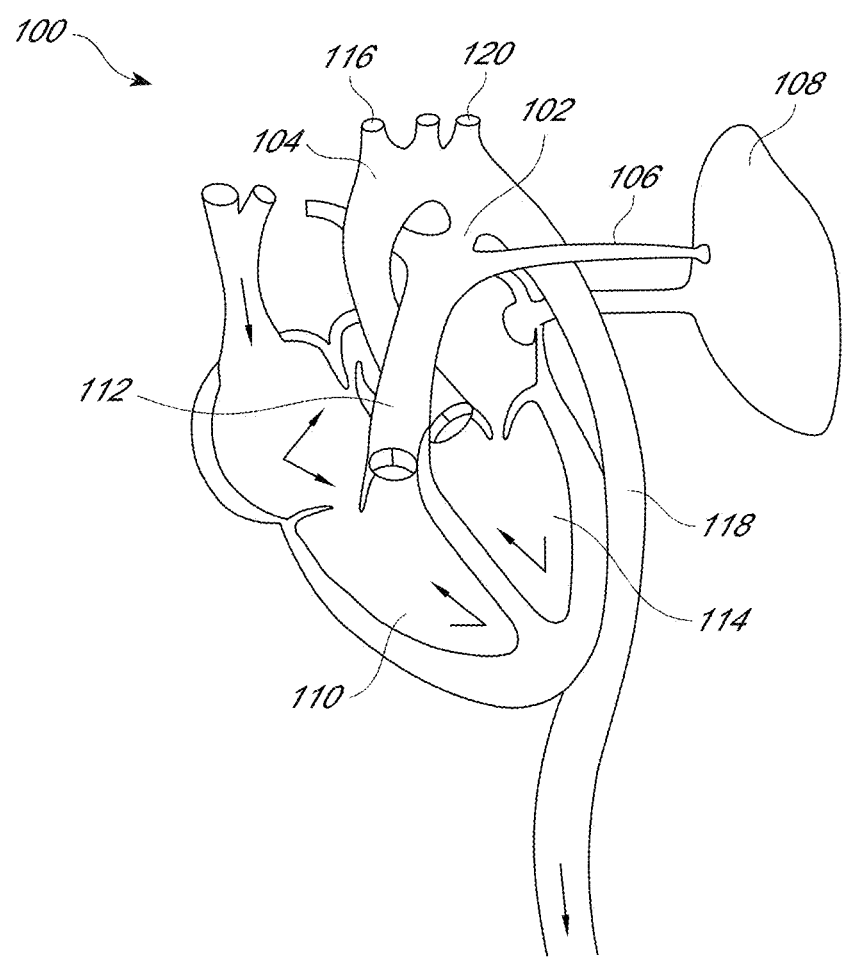
FIG. 1 illustrates a diagram of a portion of a circulatory system including a heart having a patent or open ductus arteriosus.

FIG. 1 illustrates an infant heart 100 having patent ductus arteriosus ("PDA"), and lungs 108. The infant heart 100 includes a ductus arteriosus 102, an aorta 104, a pulmonary artery 106, a right ventricle 110, a main pulmonary artery 112, a left ventricle 114, an innominate artery 116, a descending aorta 118, and a subclavian artery 120. The ductus arteriosus 102 frequently fails to close in premature infants, allowing left-to-right shunting, i.e. oxygenated "red" blood flows from the aorta 104 to the now unconstricted pulmonary artery 106 and recirculates through the lungs 108. A persistent patent results in pulmonary hyperperfusion and an enlarged right ventricle 110, which leads to a variety of abnormal respiratory, cardiac and genitourinary symptoms. Current PDA diagnosis involves physical examination, chest x-ray, blood gas analysis, echocardiogram, or a combination of the above. For example, large PDAs may be associated with a soft, long, low-frequency murmur detectable with a stethoscope. As another example, two-dimensional, color Doppler echocardiography may show a retrograde flow from the ductus arteriosus 102 into the main pulmonary artery 112. Once a problematic PDA is detected, closure can be effected medically with indomethacin or ibuprofen or surgically by ligation. Multiple doses of indomethacin are commonplace but can still result in patency, demanding ligation. A drawback to current diagnostic techniques is that clinical symptoms of a PDA can vary on an hourly basis, requiring extended and inherently intermittent testing.

In a single sensor implementation of noninvasive PDA determination or CCHD screen (as described below in referenced to FIGS. 3A-C), a sensor, such as a blood oxygenation sensor, may be placed on the right hand to determine a baseline of physiological data. For example, a pulse oximetry sensor at the right hand provides physiological data signals indicative of arterial oxygen saturation and a plethysmograph for blood circulating from the left ventricle 114 through the innominate artery 116, which supplies the right subclavian artery leading to the right arm. Because the innominate artery 116 is upstream from the PDA shunt at the ductus arteriosus 102, the oxygen saturation value and plethysmograph waveform obtained from the right hand are relatively unaffected by the shunt and serve as a baseline for comparison with readings from other tissue sites.

A sensor may then be placed on a foot to provide oxygen status for blood supplied from the descending aorta 118. The shunt at the ductus arteriosus 102 affects aortic flow. In particular, the shunt allows a transitory left-to-right flow during systole from the high pressure aorta 104 to the low pressure pulmonary artery 106 circulation. This left-to-right flow through the shunt at the ductus arteriosus 102 alters the flow in the descending aorta 118 and, as a result, affects the oxygen saturation value and plethysmograph waveform measured at the foot. The PDA condition, therefore, may be manifested as a normal plethysmograph with a characteristically narrow peak and well-defined dicrotic notch at the right-hand baseline site compared with a damped plethysmograph with a broadened peak and reduced or missing notch at the foot site. Further, the foot site waveform may be phase shifted from the baseline waveform. These plethysmograph differences are accompanied by comparable differences in arterial oxygen saturation values between the right-hand site and the foot site.

As an alternative, the sensor may be placed on the left hand to provide oxygen status for blood circulating from the left ventricle through the left subclavian artery 120 that supplies the left arm. Because the left subclavian artery 120 is nearer the shunt at the ductus arteriosus 102 than the further upstream innominate artery 116, it may experience some alteration in flow due to the shunt at the ductus arteriosus 102. The PDA condition, therefore, may also be manifested as an altered plethysmograph waveform at a left hand site as compared with the right hand baseline site, although likely to a lesser degree than with a foot site. Thus, the PDA condition, and thus a CCHD condition, can be detected and its treatment monitored from a delta in saturation (i.e., difference in $SpO_2$) values and plethysmograph morphology and phase comparisons between a right hand baseline sensor site and one or more other sites, such as the left hand or foot. One of ordinary skill will recognize that multiple site comparisons using an oximeter may also be used to detect other cardiac abnormalities that cause mixing of oxygenated and deoxygenated blood, such as a ventricular hole or a patent foramen. Further, abnormal mixing of oxygenated and deoxygenated blood may also be manifested in physiological data measurements other than oxygen saturation provided by an advanced patient monitor or pulse oximeter.

Figure 3A:
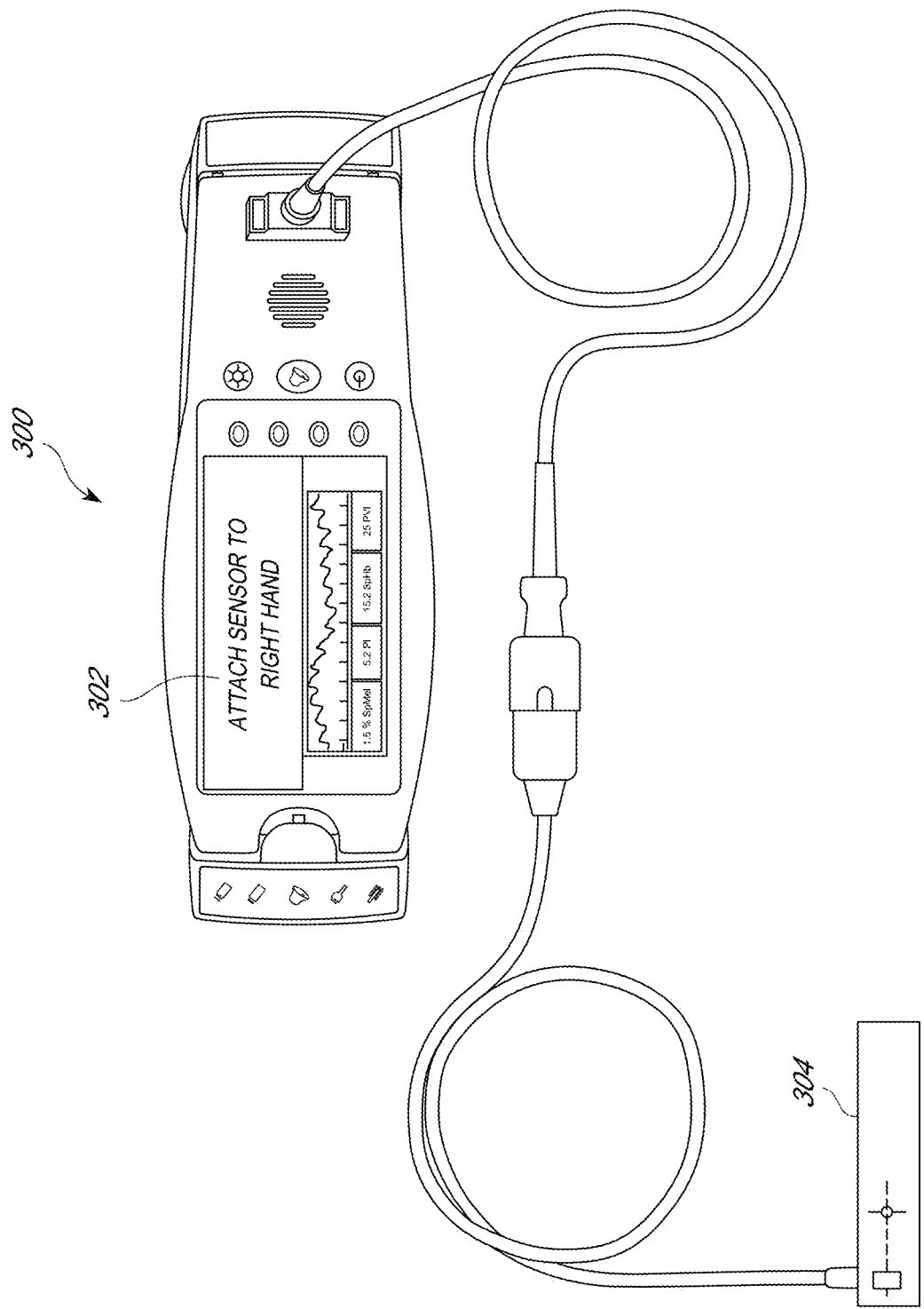
FIG. 3A illustrates a simplified view of a pulse oximeter configured to perform a CCHD screening process, according to an embodiment of the disclosure.

FIG. 3A illustrates a simplified view of a pulse oximeter configured to perform a CCHD screening process with a single sensor (as described above), according to an embodiment of the disclosure. FIG. 3A includes a pulse oximeter 300, a display 302, and a sensor 304. In an embodiment, the sensor 304 may be noninvasively attached to the patient's finger. The sensor 304 may measure various blood analytes noninvasively using multi-stream spectroscopy. In an embodiment, the multi-stream spectroscopy may employ visible, infrared and near infrared wavelengths. The sensor 304 may be capable of noninvasively measuring blood analytes or percentages thereof (e.g., saturation) based on various combinations of features and components.

The sensor 304 may include photocommunicative components, such as an emitter, a detector, and other components. The emitter may include a plurality of sets of optical sources that, in an embodiment, are arranged together as a point source. The various optical sources may emit a sequence of optical radiation pulses at different wavelengths towards a measurement site, such as a patient's finger. Detectors may then detect optical radiation from the measurement site. The optical sources and optical radiation detectors may operate at any appropriate wavelength, including infrared, near infrared, visible light, and ultraviolet. In addition, the optical sources and optical radiation detectors may operate at any appropriate wavelength, and such modifications to the embodiments desirable to operate at any such wavelength will be apparent to those skilled in the art. In some embodiments, the sensor 304 may be any of a disposable, reusable, and/or resposable sensor. Generally, for CCHD measurements, a sensor configured for use with an infant is desirable. In some embodiments, this may include a finger, toe, or ear sensor. In an embodiment, the sensor 304 may also be a wrist-type sensor configured to surround the wrist or ankle of an infant.

The sensor 304 is coupled to the pulse oximeter 300 that processes and/or displays the sensor 304's output, on, for example, display 302. The sensor 304 may additionally be coupled to one or more monitors that process and/or display the sensor 304's output. As described below in reference to FIG. 3B, the pulse oximeter 300 may include various components, such as a sensor front end, a signal processor, and/or a display, among other things.

The sensor 304 may be integrated with a monitor (such as the pulse oximeter 300), for example, into a handheld unit including the sensor 304, a display and user controls. In other embodiments, the sensor 304 may communicate with one or more processing devices. The communication may be through wire(s), cable(s), flex circuit(s), wireless technologies, or other suitable analog or digital communication methodologies and devices to perform those methodologies. Many of the foregoing arrangements allow the sensor 304 to be attached to the measurement site while the device (such as the pulse oximeter 300) is attached elsewhere on a patient, such as the patient's arm, or placed at a location near the patient, such as a bed, shelf or table. The sensor 304 and/or pulse oximeter 300 may also provide outputs to a storage device or network interface.

Figure 3B:
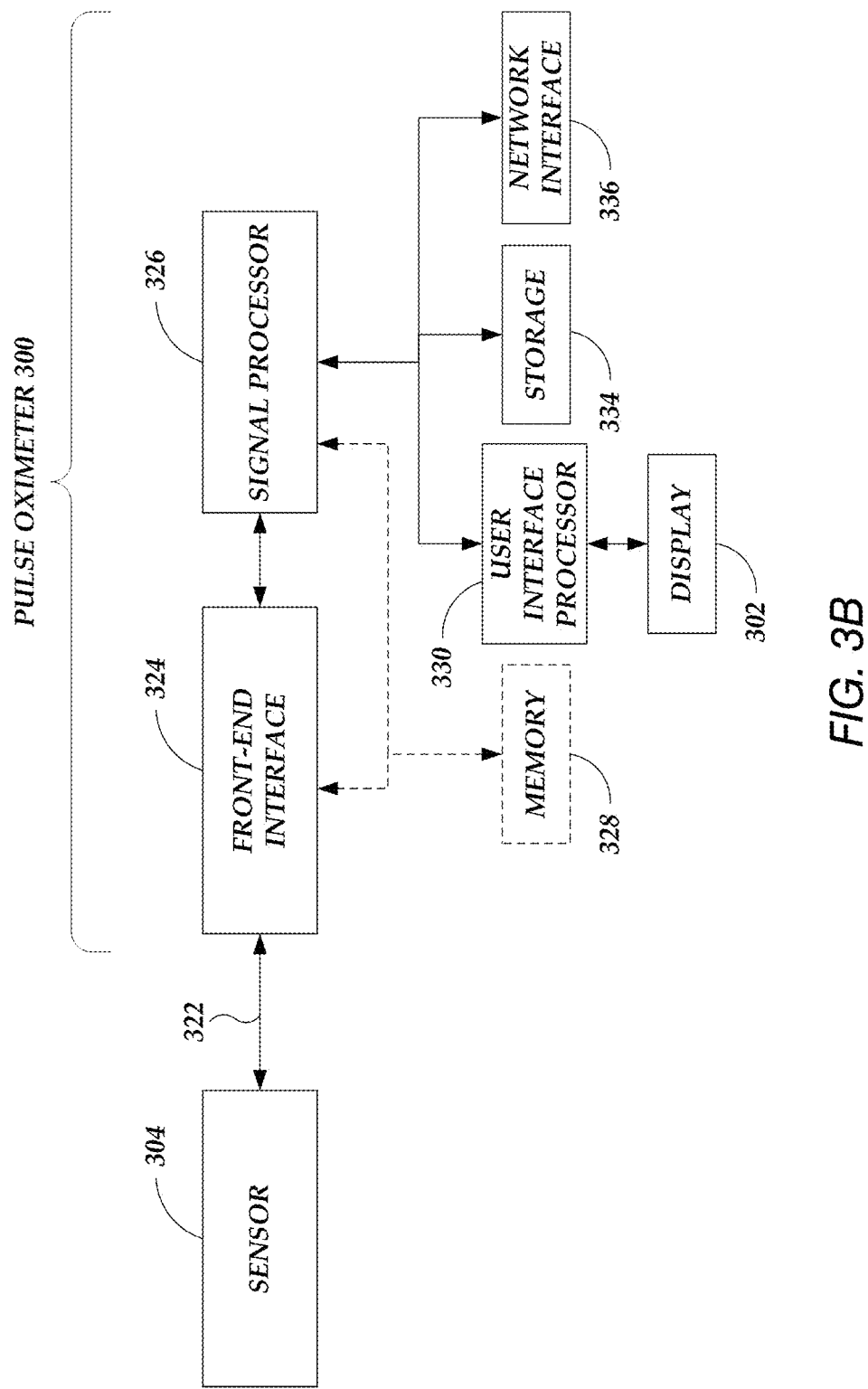
FIG. 3B illustrates a simplified block diagram of a pulse oximeter configured to perform a CCHD screening process, according to an embodiment of the disclosure.

FIG. 3B illustrates a simplified block diagram of a pulse oximeter configured to perform a CCHD screening process, as described above with reference to FIG. 3A. FIG. 3B includes the pulse oximeter 300, the sensor 304, and a communications link 322. The pulse oximeter 300 includes a front-end interface 324, a signal processor 326, a user interface processor 330, the display 302, a storage 334, a network interface 336, and an optional memory 328. In an embodiment, the signal processor 326 includes processing logic that determines measurements, for example, $SpO_2$ and/or PI. The signal processor 326 may be implemented using one or more microprocessors or subprocessors (e.g., cores), digital signal processors, application specific integrated circuits (ASICs), field programmable gate arrays (FPGAs), combinations of the same, and the like.

The signal processor 326 may provide various signals through the front-end interface 324 and the communications link 322 that control the operation of the sensor 304. For example, the signal processor 326 may provide an emitter control signal to the sensor 304. Additionally, measurement data may be transmitted from the sensor 304 to the signal processor 326. As also shown, the optional memory 328 may be included in the front-end interface 324 and/or in the signal processor 326. This optional memory 328 may serve as a buffer or storage location for the front-end interface 324 and/or the signal processor 326, among other uses.

The user interface processor 330 may provide an output, for example, on the display 302, for presentation to a user of the pulse oximeter 300. The user interface processor 330 and/or the display 302 may be implemented as a touchscreen display, an LCD display, an organic LED display, or the like. In addition, the user interface processor 330 and/or display 302 may include a flip screen, a screen that can be moved from one side to another on the pulse oximeter 300, or may include an ability to reorient its display indicia responsive to user input or device orientation. In alternative embodiments, the pulse oximeter 300 may be provided without the display 302 and may simply provide an output signal to a separate display or system.

The storage 334 and the network interface 336 represent other optional output connections that can be included in the pulse oximeter 300. The storage 334 may include any computer-readable medium, such as a memory device, hard disk storage, EEPROM, flash drive, or the like. Various software and/or firmware applications can be stored in the storage 334, which may be executed by the signal processor 326 and/or another processor of the pulse oximeter 300. The network interface 336 may be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the pulse oximeter 300 to communicate and share data with other devices (such as, for example, a remote data processing center as described below in reference to FIG. 5). The pulse oximeter 300 may also include various other components not shown, such as a microprocessor, graphics processor, and/or controller to output a user interface, to control data communications, to compute data trending, and/or to perform other operations.

Although not shown in the depicted embodiment, the pulse oximeter 300 may include various other components or may be configured in different ways. For example, the sensor 304 may measure additional advanced parameters. As described below, the pulse oximeter 300 may prompt the user to take specific actions through the display 302 to, for example, accomplish the CCHD screening process.

Figure 3C:
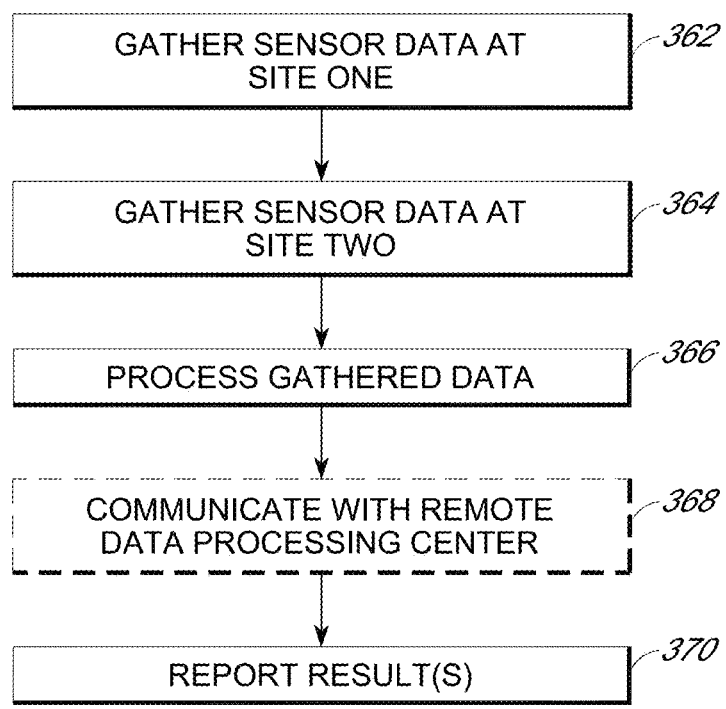
FIG. 3C illustrates an example CCHD screening process according to an embodiment of the present disclosure.

FIG. 3C illustrates an example CCHD screening process according to an embodiment of the present disclosure. This CCHD screening process may be accomplished with, for example, the pulse oximeter 300 of FIGS. 3A and 3B. At box 362, sensor data is gathered at a first site. For example, at this point the user/caregiver may be instructed to attach the pulse oximeter sensor (for example, the sensor 304) to the patient's right hand for a pre-ductal measurement. At box 364, sensor data is gathered at a second site. For example, at this point the user/caregiver may be instructed to attach the pulse oximeter sensor (for example, the sensor 304) to the patient's foot or left hand for a post-ductal measurement. In each of boxes 362 and 364, the measurement data may be transmitted from the sensor 304, through the communications link 322 and front-end interface 324, to the signal processor 326.

At box 366, the gathered pre- and post-ductal measurement data is processed by, for example, the signal processor 326. The gathered data is processed to provide both screening results (for example, the pre- and post-ductal $SpO_2$ measurements and the delta between the two), but also to reduce errors in the measurements. As stated above, drawbacks arise when data from each time-displaced measurement (baseline and alternate, pre- and post-ductal) is not carefully selected. For example, normal infant $SpO_2$ values may drift up and down more than two percent (2%). If a baby holds its breath during onset of crying, values may drift more than twenty percent (20%) in a very short time. If by chance the baseline was taken at a coincidental peak in normal variation, and the alternate was taken during crying or even at a valley or trough of normal variation, such error may impact a CCHD screening process, which, as shown in FIG. 2, may change the result based on a three percent (3%) differential between baseline and alternate.

As described above, FIG. 2 depicts the Centers for Disease Control and Prevention's ("CDC's") recommended CCHD screening process 200. A screen is considered positive (see box 228) if (1) any oxygen saturation measurement is less than ninety percent (<90%) (in the initial screen or in repeat screens) (see boxes 206, 214, and 222); (2) the oxygen saturation measurement is less than ninety five percent (<95%) in the right hand and foot on three measures (see boxes 208, 216, and 224), each separated by one (1) hour (see boxes 204, 212, 220); or (3) a greater than three percent (>3%) absolute difference exists in oxygen saturation measurements between the right hand and foot on three measures (see boxes 208, 216, and 224), each separated by one (1) hour. Any screening that is greater than or equal to ninety five percent (≥95%) in the right hand or foot with a less than or equal to three percent (≤3%) absolute difference in oxygen saturation measurements between the right hand and foot is considered a negative screen and screening would end (see boxes 210, 218, 226, and 230).

Figure 16:
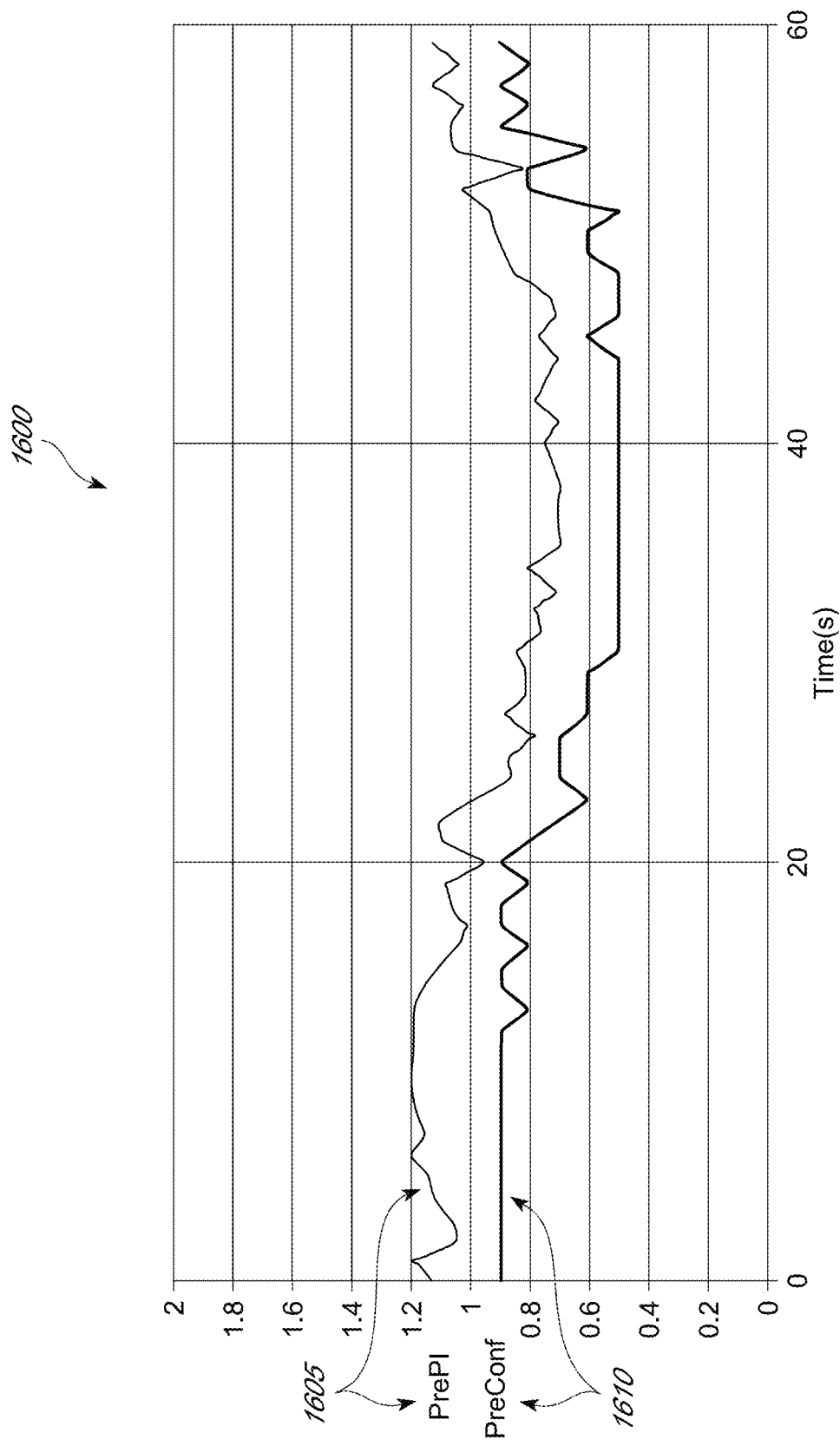
FIG. 16 illustrates an example plot of pre-ductal perfusion index and confidence measurement in a CCHD screen process, according to an embodiment of the present disclosure.

Referring back to FIG. 3C and box 366, in an embodiment, a process or processes executing on one or more signal processors (such as signal processor 326) seek to reduce errors introduced by, for example, the time differential in measurements in the single sensor implementation of CCHD screening processes. In an embodiment, confidence thresholds may indicate when signal quality is sufficiently high to use measurement data. Confidence information may also be used to weight data as it is combined for comparisons. Confidence information may be assigned to windows of data and may be used to reduce an impact of a particular window on a measurement value or adjust the value itself. Such confidence information may be advantageously incorporated into a visual queue, such as a number or a graphic, indicating a confidence in the measurement or screening itself. An embodiment of a confidence measurement is displayed in FIG. 16. FIG. 16 shows an example plot 1600 of a pre-ductal PI graph 1605 and a pre-ductal confidence graph 1610, each versus time (in seconds). The pre-ductal PI graph 1605 will be described below. Pre-ductal confidence is indicated by pre-ductal confidence graph 1610, which varies over time based on, for example, signal quality from the sensor 304 and/or PI measurements as shown in the pre-ductal PI graph 1605. In an embodiment, a sufficiently low confidence level (and/or threshold) results in a measurement error, and no result is reported to the user/caregiver. For example, a confidence threshold may be (on a scale of 0 to 1) 0.5, 0.6, 0.7, 0.8, 0.85, 0.9, 0.95, 0.96, 0.97, 0.98, 0.99, and/or 1, among other possibilities.

Referring back to box 366 in FIG. 3C, additional processing may be accomplished to ensure the measured data is reliable, and/or the user/caregiver may be notified of possible problems with the gathered data. Alternatively, the gathered data may be processed after it is gathered. For example, the sensor data at site one may be gathered and processed, followed by the gathering and processing of the sensor data of site two.

In an embodiment, indications of motion may advantageously cause an audio/visual message to be presented to a caregiver to calm the patient before measurements can be used. In an embodiment, a minimum wait time may ensure that actual stabilization of the data occurs, such as for example, about ten (10) to twenty (20) seconds or more may need to pass after an indication of cessation of motion in the patient.

Figure 15:
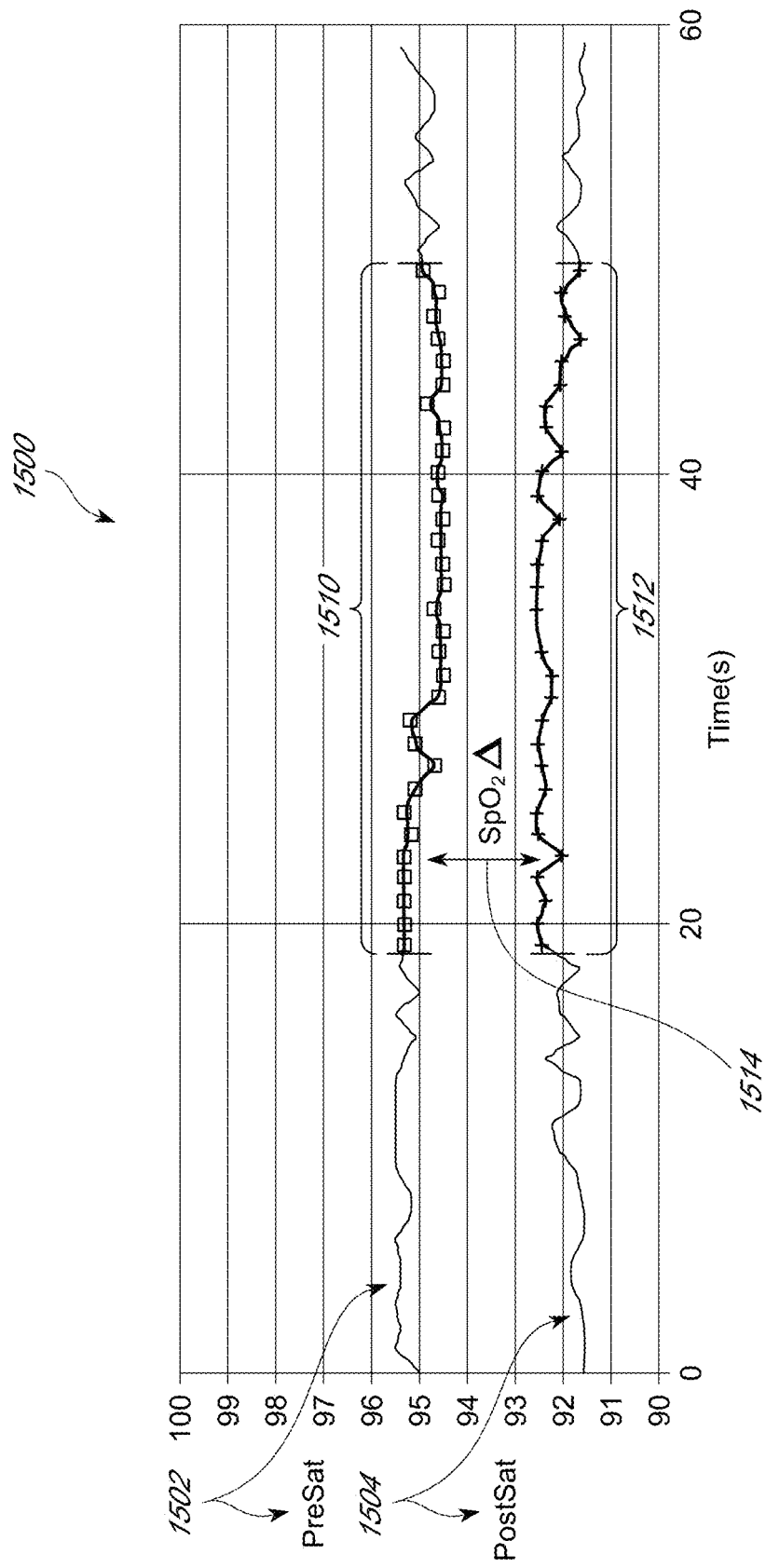
FIG. 15 illustrates an example plot of pre- and post-ductal $SpO_2$ measurements in a CCHD screen process, according to an embodiment of the present disclosure.

In an embodiment, the features of the plethsmographic data or of the oxygen saturation data values can be analyzed to determine when to use measurement data. In the case of the plethsmographic data, determination of how well the waveform fits a model may guide confidence measurements or indicate signal noise. With saturation data, troughs and peaks, and their respective severities may be determined so that measurements for each site are chosen during similar or the same waveform feature, such as, for example, using measurements that correspond to peaks for each site. In an embodiment, the natural high and low cycles of oxygen saturation are used to correlate the measurements. For example, typical pre- and post-ductal $SpO_2$ measurements are illustrated in FIG. 15. FIG. 15 shows an example plot 1500, including a pre-ductal $SpO_2$ graph 1502 and a post-ductal $SpO_2$ graph 1504, each versus time (in seconds). The $SpO_2$ measurements vary cyclically over time. Thus, in order to compare measurements from two different sites taken at different times, the natural cycles of variance in the $SpO_2$ are used to correlate the measurement data. In the example of FIG. 15, a 60 second window of data is taken of both the pre- and post-ductal measurement. The data is time adjusted so that the natural cycles of the $SpO_2$ measurements occur at roughly the same time. A window or timeframe, for example, a 30 second window of time, is analyzed, indicated as 1510 and 1512, respectively, in FIG. 15. This window or timeframe is then used to determine the $SpO_2$ delta 1514. As a result of correlating the pre- and post-ductal $SpO_2$ measurements using the natural cycles, a more accurate delta can be determined.

In another embodiment, instead of correlating pre- and post-ductal measurements using natural cycles, the system can select a measurement from each window of data that has the highest signal confidence and compare those two measurements. The system can display which pre- and post-ductal measurements were selected from the window of data. For example, the system can display a graph or trend of pre-ductal measurements and a graph or trend of post-ductal measurements, along with some indicator on each graph or trend (such as a dot, X, square, or the like) showing which value was selected. By showing the clinician this graph or trend information, the system can provide the clinician with more data with which to make an informed diagnosis of CCHD. With this additional information about measurements in the windows, which measurements were selected, and confidence of the measurements (which may be shown for some or all measurements in the window), a clinician may be more informed and even decide to change the diagnosis recommended by the system.

Referring back to box 366 in FIG. 3C, in an embodiment, additional processing may be performed and/or intermediate data may be accessed to assist in determining which measurements to select for screening deltas. For example, often sophisticated filters are used to smooth saturation measurements. In an embodiment, pre-filtered results may provide more accurate or immediate information on measurement selection. Similarly, ratio or other information may be used in addition to or in place of focusing on oxygen saturation values.

In an embodiment, phases in the respiration cycle may be accounted for to select measurement data. For example, measurement values may correspond to only data during, for example, the inspiration phase, or the like. In an embodiment, respiration or pulse rates may qualify or disqualify measurement data, based on, for example, rate stability or the like.

Other parameter information may also be used. For example, perfusion index ("PI") information may provide indicators on when to select measurement data. In an embodiment, PI may vary for reasons unrelated to CCHD and therefore can be used in certain implementations, such as ranges that qualify or disqualify measurement data or the like. For example, the perfusion index may indicate that signal quality is sufficiently high to use measurement data. A PI measurement is also illustrated in FIG. 16 as pre-ductal PI graph 1605. Although both confidence and PI have been illustrated with respect to a pre-ductal measurement in FIG. 16, it is to be understood that a similar PI and confidence measure may also be determined for a post-ductal measurement.

In box 368 of FIG. 3C, the pulse oximeter 300 may optionally communicate with a remote data processing center, through, for example, the network interface 336. As described below in reference to FIG. 5, current measurement data may be transmitted to the remote data processing center, and/or previous measurement data may be accessed from the remote data processing center, among other things. Thus, the results of multiple measurements may be stored, retrieved, and/or compared as part of the CCHD screening process. Alternatively, measurement data may be stored at the pulse oximeter 300. In an embodiment, the data processing of box 366 takes place at the remote data processing center.

In box 370, the results of the CCHD screening are reported to the caregiver/patient/user. This may be accomplished, for example, by displaying the results on the display 302 as a number, color, and/or other symbol, and/or aurally in the form of, for example, an alarm.

An artisan will recognize from the disclosure herein a wide variety of indicators or combinations of indicators for determining when to select measurement data for use in CCHD screening processes. For example, segments or whole windows of data for the various parameters and indicators discussed in the foregoing may be combined to provide additional insight into measurement selection. Moreover, any or combinations of the foregoing may be used to adjust a particular measurement instead of seeking a different measurement.

Figure 4:
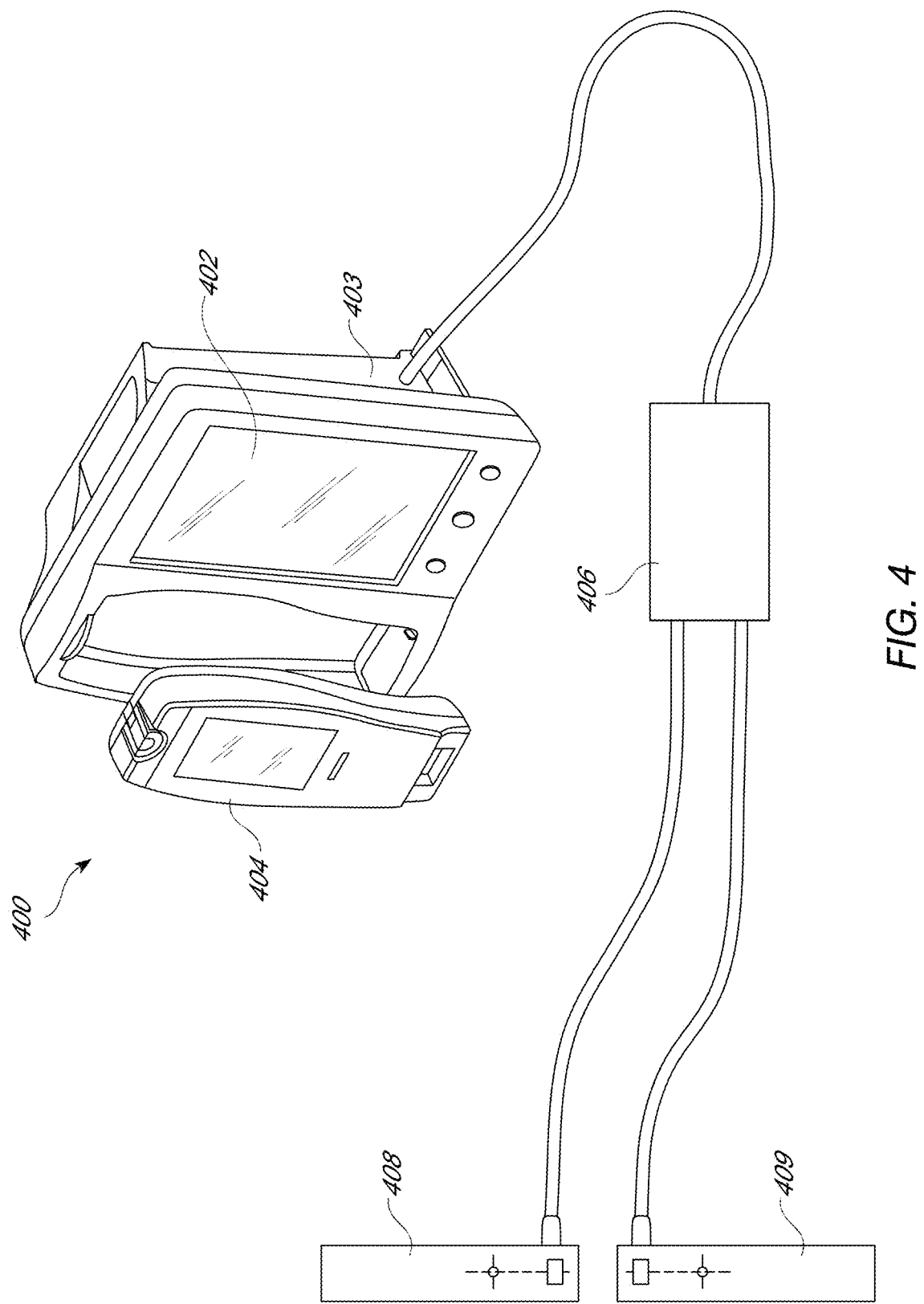
FIG. 4 illustrates a simplified perspective view and block diagram of a pulse oximeter configured to perform a CCHD screen process including dual sensors, according to an embodiment of present disclosure.

FIG. 4 illustrates an embodiment of the CCHD screening system incorporating dual (or stereo) sensors. FIG. 4 includes a pulse oximeter 400, a signal processing device 406, a first sensor 408, and a second sensor 409. Further, the pulse oximeter 400 includes a display 402, a communication port 403, and a portable oximeter 404. Such a pulse oximeter is commercially available from Masimo Corporation of Irvine, CA. Other CCHD systems may employ more than two sensors. In an embodiment, the pulse oximeter 400 includes a USB or other communication port 403 that connects to the signal processing device 406. In this embodiment, each of the dual sensors (first sensor 408 and second sensor 409) connects to the signal processing device 406. Either of the first sensor 408 or the second sensor 409, or both the first sensor 408 and the second sensor 409, may comprise any combination of disposable, reusable, and/or resposable sensors. As described above, the first sensor 408 and/or the second sensor 409 may be configured for use with an infant. Additionally, the two sensors are not required to be of the same type, but may be any combination of suitable sensors. For example, in some embodiments, the first sensor 408 and/or the second sensor 409 may include finger, toe, or ear sensors, or any combination of finger, toe, or ear sensors. In another example, the first sensor 408 and/or the second sensor 409 may be a wrist-type sensor configured to surround the wrist or ankle of an infant. The signal processing device 406 provides stereo processing of sensor signals, such as those disclosed in the '065 Patent. In an embodiment, such processing may include separate oximeter calculators logically similar to having two independent oximeters, one for each sensor. The pulse oximeter 400 may include components similar to those of the pulse oximeter 300 of FIG. 3B. Specifically, the pulse oximeter 400 may include a signal processor, among other things. Processing of sensor data may take place in the pulse oximeter 400 and/or the signal processing device 406.

In this stereo embodiment of two (2) or more sensors, while there may not necessarily be time differentials between measurements, the data from each sensor may be of varying quality. Thus, many of the same procedures disclosed in the foregoing will apply. For example, at a particular time, the data from the baseline sensor may be clean with a high confidence while the data from the alternate sensor may have low quality from motion artifact, such as, for example, an infant kicking but not moving their right hand. Thus, the signal processing device 406 may use the foregoing processes to select measurement values from each sensor at different times. In such cases, determining which measurements should be used involves determinations similar to those used in the single sensor implementation. Alternatively, the signal processing device 406 may wait and select a time when both sensors produce usable measurement data, similar data conditions, or the like.

In an embodiment, the signal processing device 406 determines measurements for each of first sensor 408 and second sensor 409, and forwards measurement values to the pulse oximeter 400. The monitor 400 advantageously includes CCHD screening modules that guide a caregiver through the screening process. In other embodiments, the signal processing device 406 executes the screening and sends flags or messages to the display 402 and/or the portable oximeter 404 directing the display 402 and/or the portable oximeter 404 to display caregiver instructions and/or output results.

Although disclosed as the processing device 406 separate from the pulse oximeter 400, an artisan will recognize from the disclosure herein that the processing of the signal processing device 406 may be incorporated into the pulse oximeter 400 and/or the portable oximeter 404.

Figure 5:
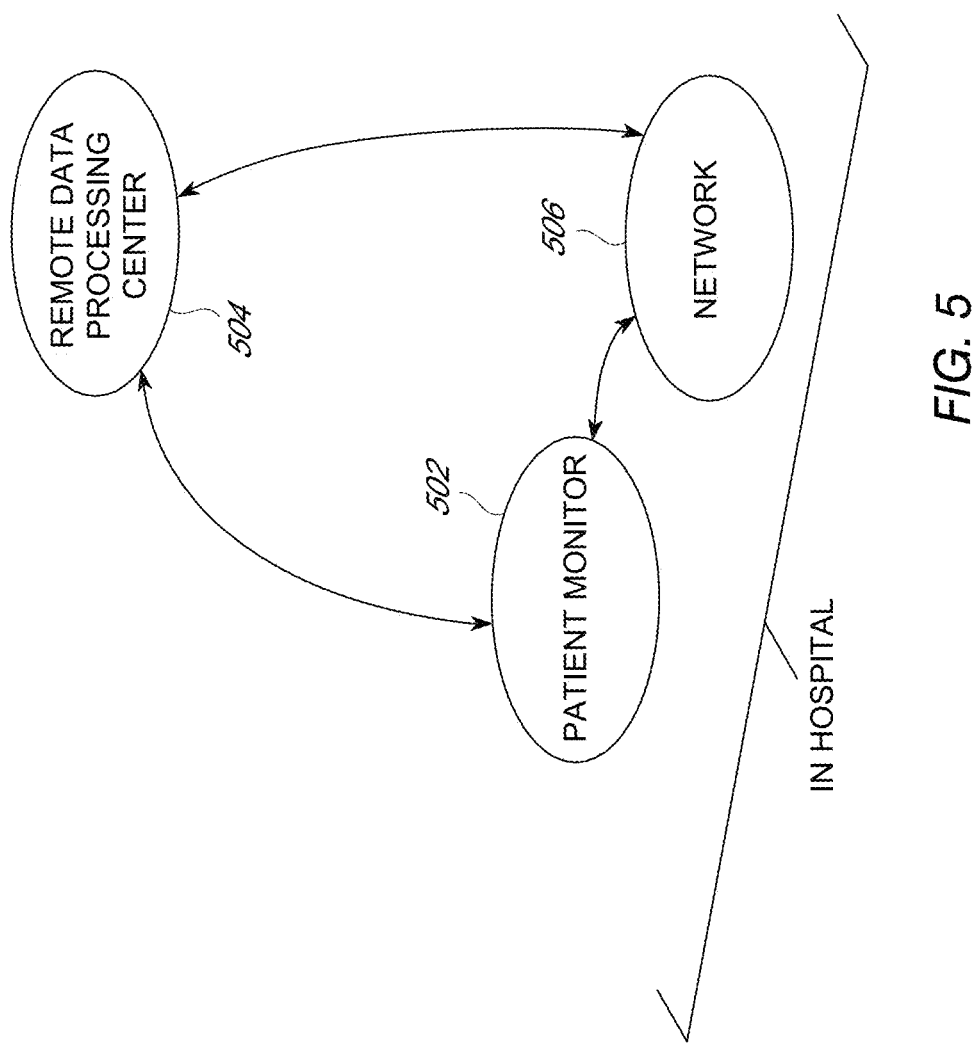
FIG. 5 illustrates a data diagram of a data sharing system, according to an embodiment of present disclosure.

FIG. 5 illustrates a data diagram of a data sharing system, according to an embodiment of present disclosure. FIG. 5 includes a patient monitor 502, a remote data processing center 504, and a network 506. In an embodiment, the patient monitor 502 may include, for example, either the pulse oximeter 300 of FIG. 3A or the pulse oximeter 400 of FIG. 4. In an embodiment, the patient monitor 502 and the network 506 may communicate with one another, and may be located in a hospital, while both the patient monitor 502 and the network 506 may advantageously communicate with the remote data processing center 504. The network 506 may include, for example, Masimo's Patient SafetyNet System, a hospital patient data system, and/or any other wired or wirelessly connected system. An artisan will recognize that communications among any of the patient monitor 502, the remote data processing center 504, and the network 506 may be through any appropriate wired and/or wireless data transmission, and may use any suitable communications protocol. For example, communication may be serial or parallel, through Universal Serial Bus (USB) (wired or wireless), Ethernet, Bluetooth, Near Field Communications (NFC), radio frequency (RF), infrared, and/or WiFi (such as any 802.1x interface), among others as is known in the art.

In an embodiment, the remote data processing center 504 may store, for example, Patient ID's, device information (such as, for example, patient monitor 502 device information), sensor information, measurement data, screening data, and/or screening determinations for comparisons with later screening events. For example, the CCHD screening process of FIG. 2 includes multiple repeat screens. In this example, previous screening data for a particular patient, among other things, may be requested by the patient monitor 502, when for example, a new screening is performed. Thus, the data from the two screening may be compared or used in some other way. Such communication may advantageously be wirelessly directed from the patient monitor 502 to the remote data processing center 504, or through one or more intermediary networks (such as the network 506). For example, the patient monitor 502 may include wireless communication to a hospital or other network which eventually communicates with the remote data processing center 504.

In an embodiment, the pulse oximeter 300 may communicate with network 506 (or other host digital network or system) to store or upload measurement data associated with a unique identifier (e.g., a patient ID) to remote data processing center 504. The network 506 may include multiple networks or systems. The pulse oximeter 300 may access previously stored information, such as, for example, earlier screening data stored at the remote data processing center 504 of a remote network, to complete or increment the CCHD screening process. In an embodiment, a first network may be an institutional network such as a hospital data system, a cellular or other data system, or the like, wirelessly communicating with the pulse oximeter 300 or monitor. The system or systems eventually allow communication to a remote data processing center 504 or other processing center that stores the measurement information in a manner that provides for retrieval and appropriate association with newly acquired data.

As will be described in detail below, FIGS. 6-9, 10A-B, 11A-B, 12A-C, 13A-C, and 14A-D illustrate example screen shots and/or displays of a pulse oximeter monitor (such as the pulse oximeter 300 of FIG. 3A or the pulse oximeter 400 of FIG. 4) and/or other CCHD measurement device configured for measuring CCHD, according to embodiments of the present disclosure.

Figure 6:
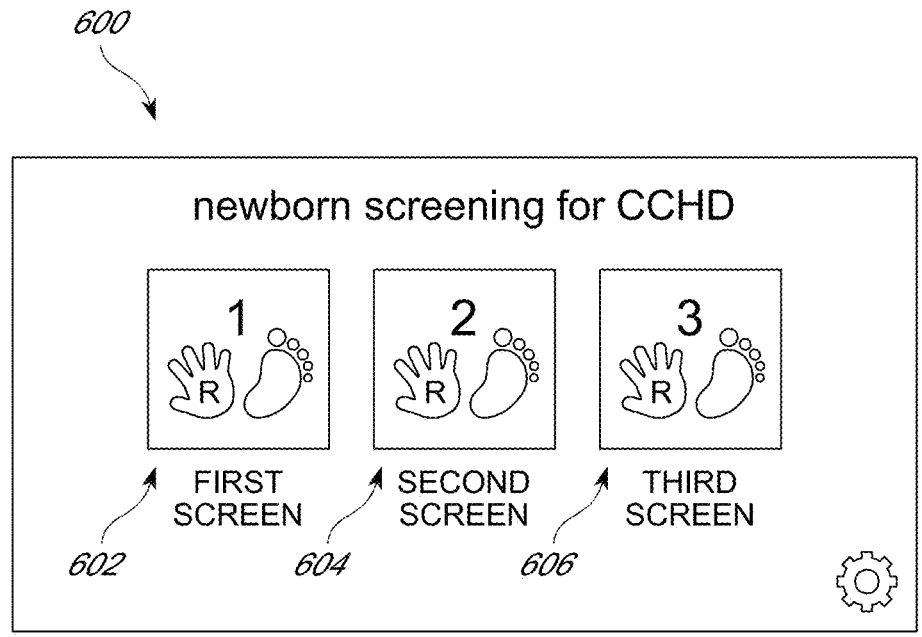
FIG. 6 illustrates an example screen shot of a pulse oximeter monitor configured for measuring CCHD, according to an embodiment of the present disclosure.

FIG. 6 illustrates a screen shot 600 of a pulse oximeter monitor configured for measuring CCHD. The screen shot 600 includes a first screen 602, second screen 604, and third screen 606 for measuring CCHD. These three screens correlate to the three separate measurement recommendations for measuring CCHD, as described in reference to FIG. 2. A touch screen can be provided in the pulse oximeter monitor so that a caregiver need only touch each measurement (for example, first screen 602, second screen 604, and third screen 606) in succession to begin the three different measurement processes.

Figure 7:
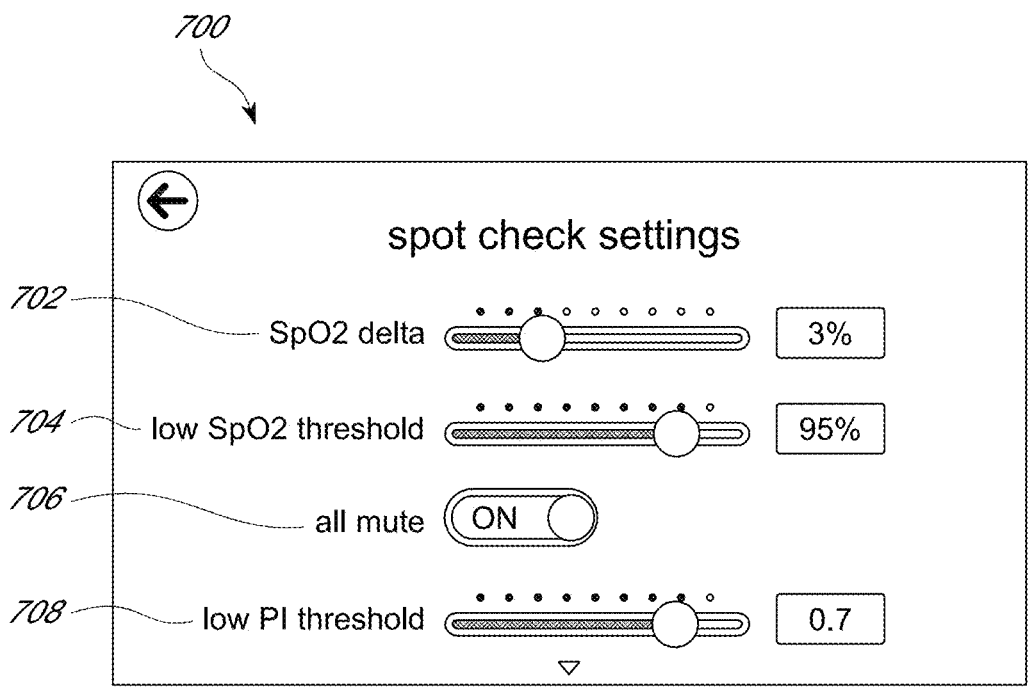
FIG. 7 illustrates an example screen shot, including spot check settings, of a pulse oximeter monitor configured for measuring CCHD, according to an embodiment of the present disclosure.

FIG. 7 illustrates various spot check settings that are available on the pulse oximeter monitor and/or CCHD measurement device of the present disclosure. A $SpO_2$ delta 702 allows a caregiver to dictate a specific difference in $SpO_2$ between measurement sites that will indicate a CCHD problem. The value can range between 1 and 10 with a default value of 3. The low $SpO_2$ threshold 704 indicates a minimal passing $SpO_2$ value for a test result. The value can range between 85-100 with a default value of 95. The all mute 706 mutes all noise from the pulse oximeter monitor and/or CCHD measurement device. The low PI threshold 708 indicates a minimum PI measurement value that may still indicate a valid test result. This value can range between 0.1 and 1 with a default value of 0.7.

Figure 8:
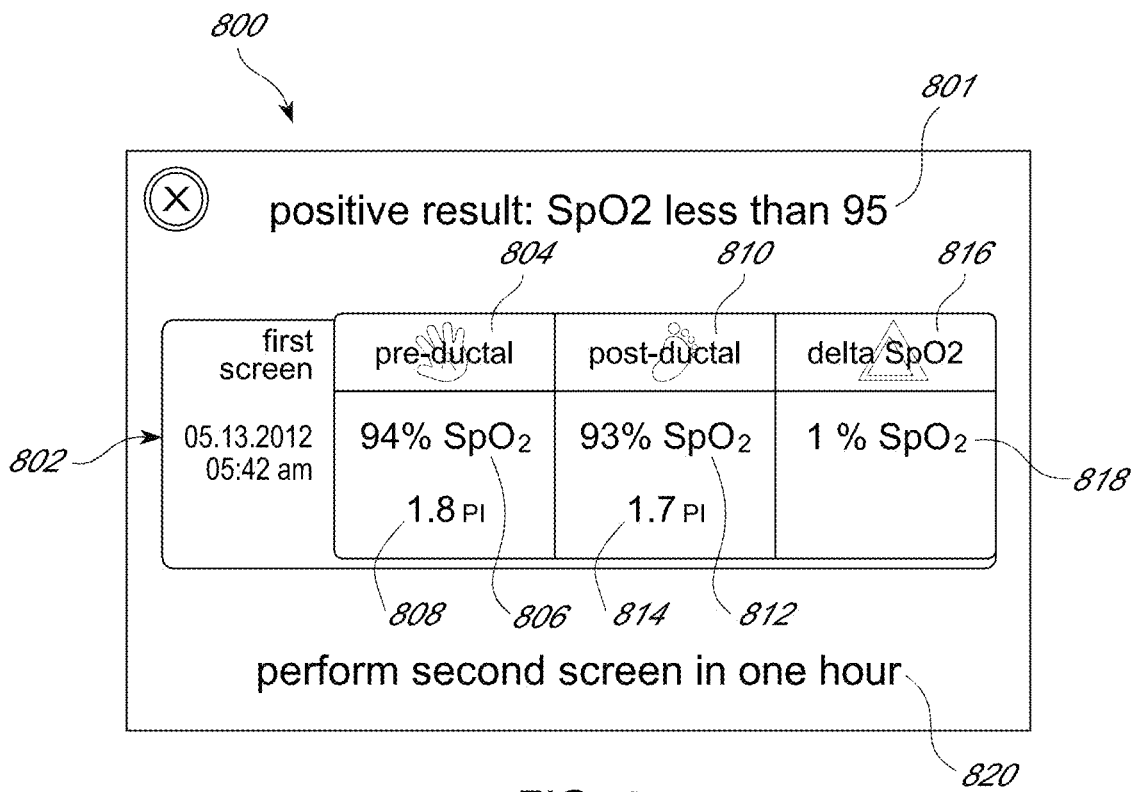
FIGS. 8-9 illustrate example screen shots, including test results, of a pulse oximeter monitor configured for measuring CCHD, according to an embodiment of the present disclosure.

FIG. 8 illustrates a display of a first test results page 800. The first test results page 800 includes a first test results indication 801. In the embodiment of first test results page 800, a positive result was obtained, but it was at a saturation value of less than 95%. The first test results page 800 also includes the time of the test 802, the pre-ductal results 804 and post-ductal results 810, including the respective $SpO_2$ values 806, 812 and PI values 808 and 814, as well as the delta $SpO_2$ 816 illustrating the delta $SpO_2$ value 818. The first test results page 800 also includes a next step indication 820. For example, in the embodiment of FIG. 8, the next step may indicate that a second screen test is to be performed in an hour. Alternatively, the next step may indicate that no further testing is required (in the event of, for example, a negative screen).

Figure 9:
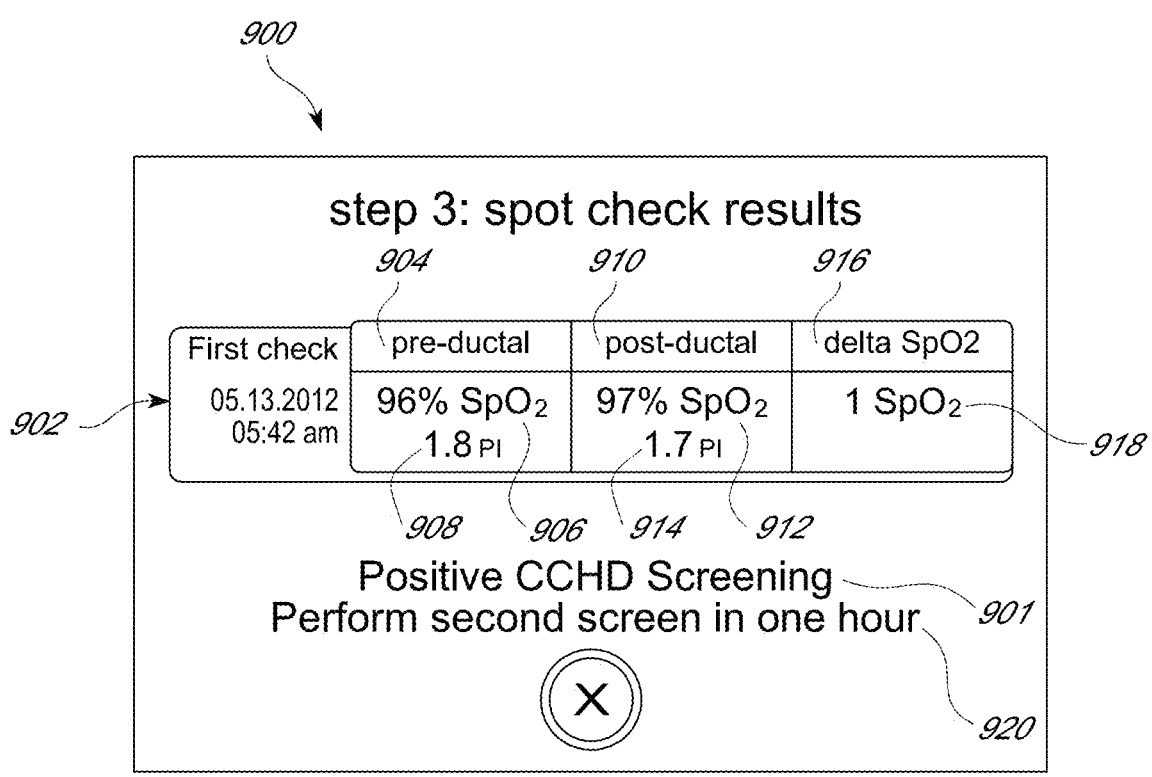

FIG. 9 illustrates another example of a first test results page 900. The test results page has similar features corresponding to that of FIG. 8 shown in an alternative format. The first test results page 900 includes a first test results indication 901. In the embodiment of first test results page 900, a positive result was obtained. The first test results page 900 also includes the time of the test 902, the pre-ductal results 904 and post-ductal results 910, including the respective $SpO_2$ values 906, 912 and PI values 908 and 914, as well as the delta $SpO_2$ 916 illustrating the delta $SpO_2$ value 918. The first test results page 900 also includes a next step indication 920.

Figure 10A:
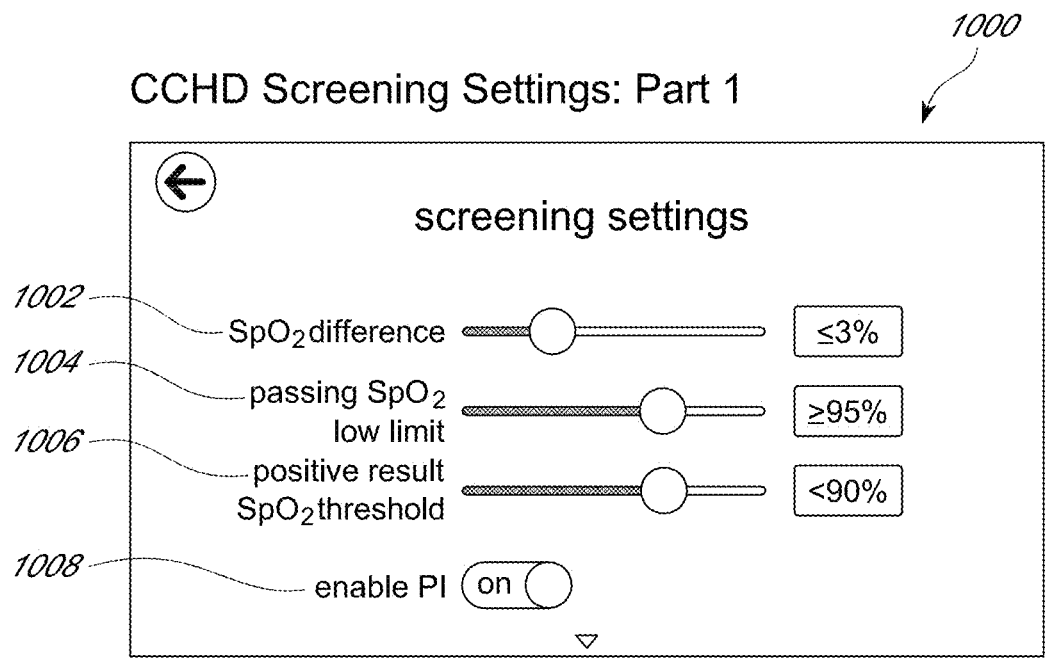
FIGS. 10A-B illustrate example screen shots, including alternative screening settings, of a pulse oximeter monitor configured for measuring CCHD, according to an embodiment of the present disclosure.
Figure 10B:
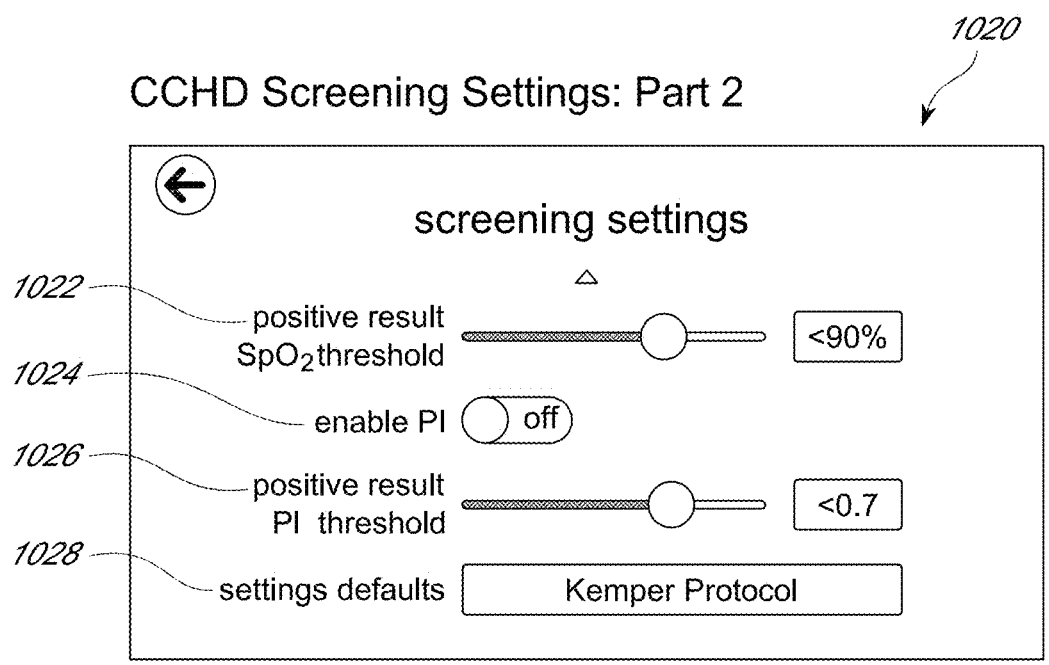

FIGS. 10A and 10B illustrate additional alternative embodiments of settings available for the CCHD monitor of the present disclosure. Referring to FIG. 10A, screen 1000 includes settings which indicate the difference in $SpO_2$ readings ($SpO_2$ difference 1002) between sites to indicate a CCHD problem. The screen settings also include passing $SpO_2$ low limit 1004, positive result $SpO_2$ threshold 1006, and enable PI 1008. Referring to FIG. 10B, additional settings on screen 1020 include positive result $SpO_2$ threshold 1022, enable PI 1024, positive result PI threshold 1026, and settings defaults 1028. The settings defaults can include different protocols for measuring CCHD including the Kemper Protocol.

Figure 11A:
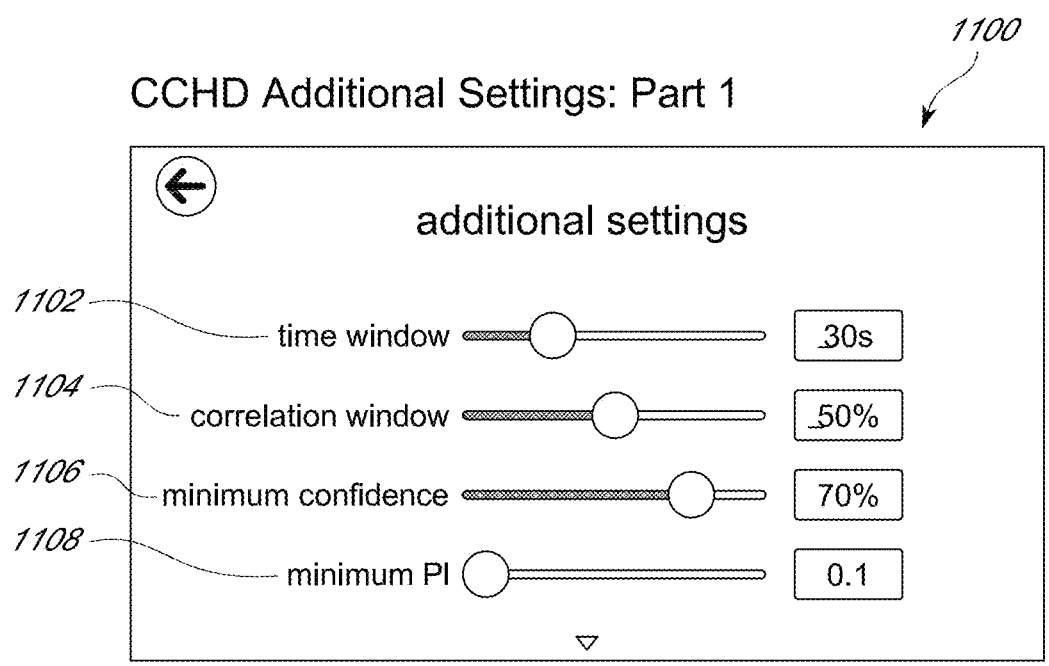
FIGS. 11A-B illustrate example screen shots, including additional settings, of a pulse oximeter monitor configured for measuring CCHD, according to an embodiment of the present disclosure.
Figure 11B:
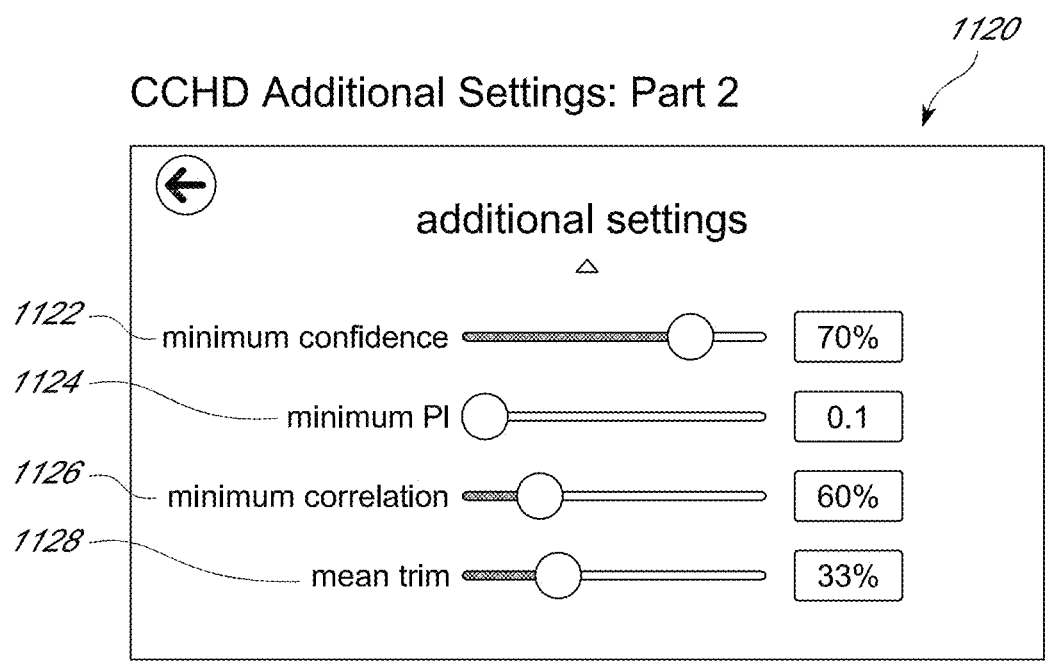

FIG. 11A illustrates additional advanced settings in screen 1100, including a time window 1102, a correlation window 1104, a minimum confidence 1106, and minimum PI 1108. In FIG. 11B other settings are illustrated in screen 1120, including minimum confidence 1122, minimum PI 1124, minimum correlation 1126, and mean trim 1128. In addition to the settings shown, in one embodiment, another option is provided for clinicians to adjust the amount of time between successive CCHD screenings. Although one hour between screenings is common, for instance, a hospital may instead have a policy that successive screenings occur every two hours. An option to adjust screening times in the system's settings can permit hospitals to implement their own policies with the CCHD system described herein. Based on the adjusted setting, the system can schedule or remind clinicians to screen a patient at the desired time.

Figure 12A:
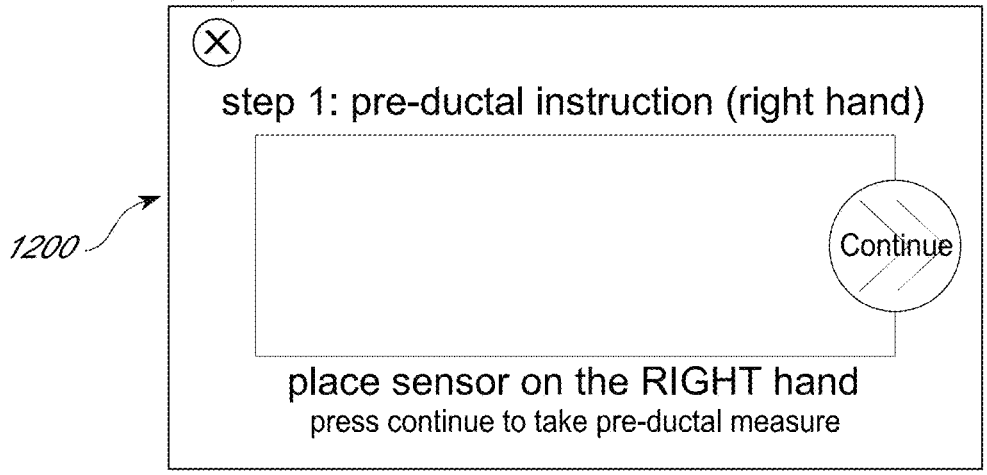
Figure 12B:
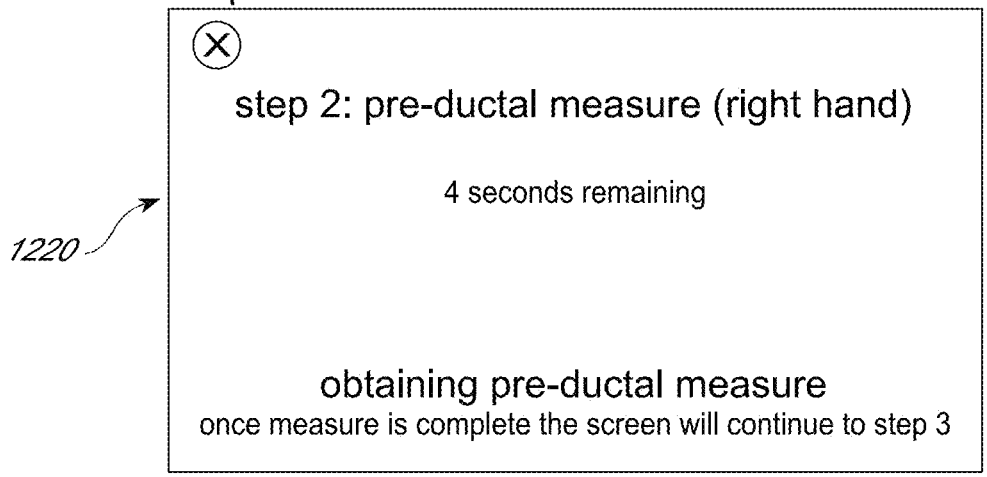
Figure 12C:
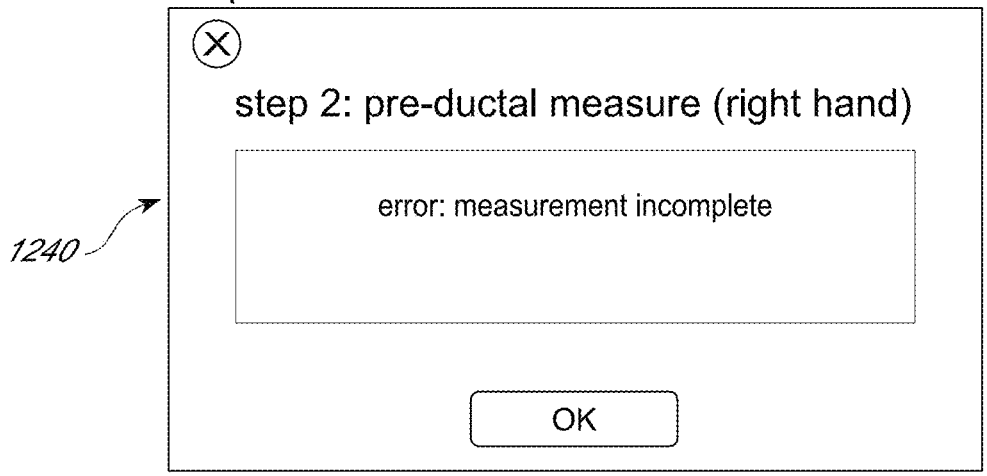

Once all of the settings are configured, the CCHD screening device of the present disclosure provides step by step instructions for performing a CCHD test protocol. FIGS. 12A-C, 13A-C, and 14A-D illustrate instructions provided for the single sensor CCHD monitor of the present disclosure. FIGS. 12A-C illustrate an embodiment of various protocol step-by-step instructions. For the pre-ductal measurement, instruction screen 1200 instructs a caregiver to place the sensor on the right hand and press a button on the screen to move to the next instruction screen 1220. Instruction screen 1220 indicates that a measurement is taking place. If an error occurs in the measurement, an error screen 1240 is displayed. In an embodiment, the CCHD screening system (including, for example, pulse oximeter 300 or pulse oximeter 400) controls and tracks the implementation of the screening process, including instructions to caregivers on next steps, as described. Additional examples of instruction may include "Attach Sensor to Right Hand," "Attach Sensor to Alternate Site," "Attach Sensor to Right Foot," "Attach Sensor to Left Foot," "Calm Patient," "Adjust Sensor Positioning," or the like.

Figure 13A:
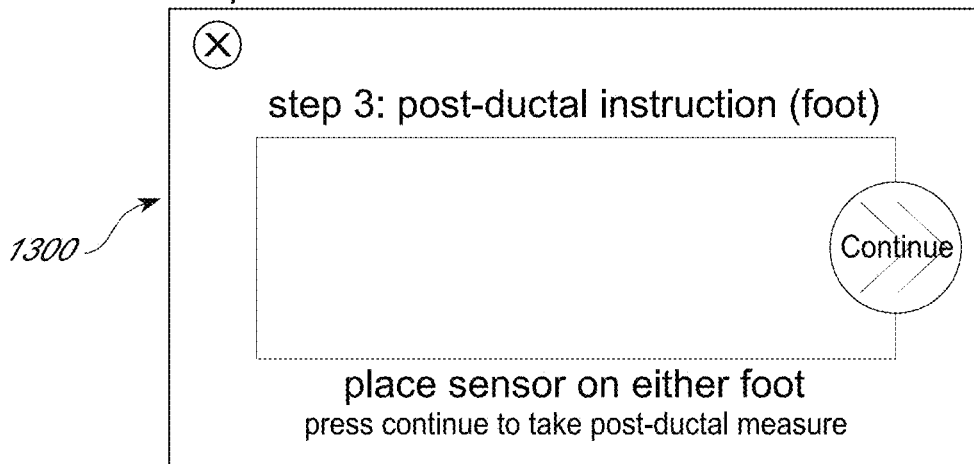
Figure 13B:
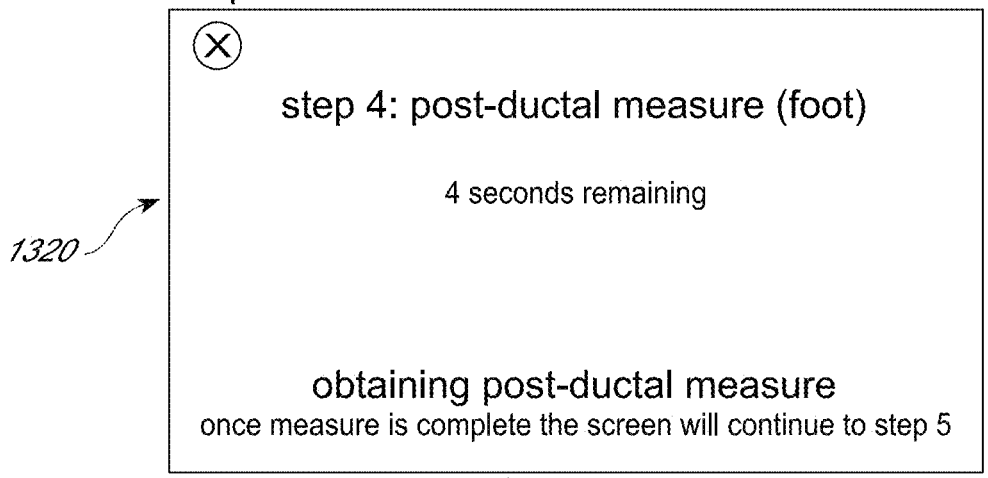
Figure 13C:
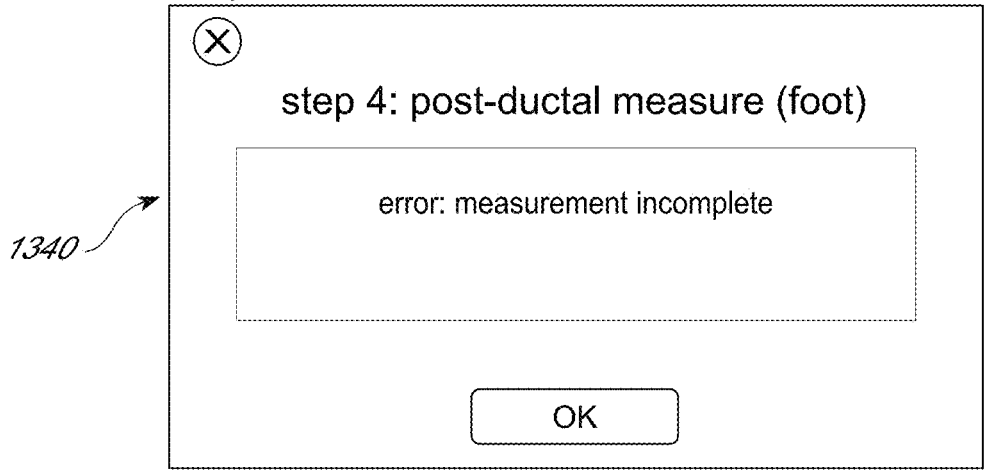

Once the pre-ductal measurement is obtained, the instructions move on to the instruction screens of FIGS. 13A-C. Instruction screen 1300, labeled as step 3, instructs the caregiver to place the sensor on the either foot of the patient and press a button to continue to instruction screen 1320. In instruction screen 1320, labeled as step 4, the post-ductal measurement is obtained. If an error occurs in the post-ductal measurement, an error screen 1340 is presented to the user.

The instructions continue with FIGS. 14A-D. Once the post-ductal measurement is obtained, results screen 1400, labeled as step 5, is displayed. The results screen 1400 provides the pre- and post-ductal screening results, as well as the difference in $SpO_2$. The results screen 1400 illustrates an embodiment in which a passing test was obtained and instructions that the test was passed are provided on the screen at 1405. Alternatively, if a potential problem was found, as illustrated in results screen 1420 of FIG. 14B, then an instruction is provided at 1425 instructing the care giver to perform a second test in one hour. If a second screening indicates a failing test, as illustrated in results screen 1440 of FIG. 14C, then an instruction is provided to perform a third screen testing in one hour at 1445. If the results of the third test also indicate a problem, for example in screen 1460 of FIG. 14D, then an instruction is provided to refer the newborn for further medical evaluation at 1465. As described above, the CCHD screening system may include a quality indicator providing information on the confidence in the screening measurements. A quality measure may be included for each measurement, for the entire screen, or the like. For example, the display may indicate "Positive Screen, 72% Confidence." In an embodiment, a minimum confidence threshold may be used to instruct a caregiver to repeat the measurements and/or restart the screening process. Moreover, the oximeter may produce an audio/visual alarm indicating time for a repeat screen, may accept patient information including a patient identifier, and the like.

Although the foregoing has been described in terms of certain preferred embodiments, other embodiments will be apparent to those of ordinary skill in the art from the disclosure herein. For example, other CCHD screening methodologies may take advantage of the processes for matching measurements disclosed herein. Moreover, data conditions from one screen may influence when measurements are chosen for subsequent screens. For example, if choosing according to peaks in the $SpO_2$ values was implemented to match measurement conditions in one screen, the same may be used or implemented in subsequent screens. Accordingly, the present disclosure is not intended to be limited by the reaction of the preferred embodiments, but is to be defined by reference to the appended claims.

In addition to the foregoing, all publications, patents, and patent applications mentioned in this specification are herein incorporated by reference to the same extent as if each individual publication, patent, or patent application was specifically and individually indicated to be incorporated by reference.

Moreover, the oximeters discussed in the foregoing may include many or all of the features of basic pulse oximeters that determine measurements for blood oxygen saturation ("$SpO_2$"), pulse rate ("PR") and plethysmographic information, to read-through-motion oximeters, to co-oximeters that determine measurements of many constituents of circulating blood. For example, Masimo Corporation of Irvine California ("Masimo") manufactures pulse oximetry systems including Masimo SET® low noise optical sensors and read through motion pulse oximetry monitors for measuring $SpO_2$, PR, perfusion index ("PI") and others. Masimo sensors include any of LNOP®, LNCS®, SofTouch™ and Blue™ adhesive or reusable sensors. Masimo oximetry monitors include any of Rad-8®, Rad-5®, Rad-5v® or SatShare® monitors.

Also, many innovations improving the measurement of blood constituents are described in at least U.S. Pat. Nos. 6,770,028; 6,658,276; 6,157,850; 6,002,952; 5,769,785 and 5,758,644, and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, and are incorporated by reference herein.

Masimo also manufactures more advanced co-oximeters including Masimo Rainbow® SET, which provides measurements in addition to $SpO_2$ such as total hemoglobin (SpHb™), oxygen content (SpCO™), methemoglobin (SpMet®), carboxyhemoglobin (SpCO®) and PVI®. Advanced blood parameter sensors include Masimo Rainbow® adhesive, ReSposable™ and reusable sensors. Masimo's advanced blood parameter monitors include Masimo Radical7™, Rad87™, and Rad57™ monitors as well as Pronto and Pronto-7 spot check monitors.

Innovations relating to these more advanced blood parameter measurement systems are described in at least U.S. Pat. Nos. 7,647,083; 7,729,733; U.S. Pat. Pub. Nos. 2006/0211925; and 2006/0238358, incorporated by reference herein.

Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

Thus, by employing the embodiments of the CCHD screening processes and systems disclosed herein, CCHD, particularly PDA, may be more accurately detected and diagnosed. Specifically, false positives may be reduced, variances in $SpO_2$ may be detected and filtered, caregivers may be more properly directed, and/or measurement confidence may be evaluated, among other advantages.

Telemedicine and Remote Diagnostic Embodiments

CCHD screening, as well as other forms of patient monitoring, can be performed remotely using telemedicine technologies. In addition to having its ordinary meaning, the term "telemedicine," as used herein, can refer to the remote diagnosis and/or treatment of patients using telecommunications technology. In one form, telemedicine can include a doctor communicating with a patient via video, with both the patient and the doctor able to see video and hear audio of the other, although one way video feeds (or two-way audio without video feeds) are used in some implementations. Telemedicine can facilitate more efficient and coordinated care, making homestay a possibility for a variety of patients. Remote monitoring and surveillance, along with virtual consultations, can reduce hospital admissions and length of stay, cutting costs while reinforcing continued routine care and self-management. However, limited integrated communication capabilities, lack of device interoperability, and poor network connectivity have hindered the rapid adoption of telemedicine solutions.

Embodiments of noninvasive point-of-care monitoring devices described herein are capable of gathering patient data from a variety of third-party devices connected via Bluetooth and transmitting patient data to remote locations and to electronic medical records (EMRs). Some point-of-care devices described herein can also offer built-in cameras, facilitating one- and two-way patient-clinician communication.

Some point-of-care devices described herein can have the ability to serve as a connectivity hub for multiple third-party and proprietary devices, aggregating the data from each peripheral device via Bluetooth. In addition, the point-of-care devices can facilitate the transmission of patient data to clinicians and live video conferencing, allowing a single device to serve as an all-inclusive, integrated solution.

Embodiments of such a device, which may be used to implement any of the features described herein, are disclosed in U.S. Pub. No. 2015/0097701, filed Oct. 10, 2014, titled "System for Displaying Medical Monitoring Data," U.S. patent application Ser. No. 14/512,237, the disclosure of which is hereby incorporated by reference in its entirety.

Any of the devices described herein can include a built-in camera, which can enable live, high-resolution (or lower resolution) video and audio feeds directly from the device to a central monitoring station (e.g., nurse's station) or to clinicians' devices (such as phones, tablets, laptops, computers, TVs, etc.), allowing clinicians to provide on-demand care and support. Real-time, two-way communication can allow care providers to manage individualized care plans, make efficient, informed assessments, and provide cost-effective, high-quality care at patients' convenience. One-way, surveillance monitoring can enable care providers to observe patient movements and listen to breathing for virtual assessment without disturbing the patient.

Although telemedicine may be used in hospital or other clinical settings, it can also be beneficial to use telemedicine in patients' homes (or wherever patients may be). A patient at home or mobile can use an electronic device, such as a phone, tablet, laptop, or desktop to communicate with a clinician. The patient may be provided monitoring equipment that interfaces with the patient's electronic device, such as noninvasive sensors (e.g., a blood pressure cuff). Outside of a hospital or clinical setting, however, patients may struggle to use patient monitoring equipment properly. Similarly, patients may struggle to interpret the measurements obtained from patient monitoring equipment. A patient may take a blood pressure measurement at home, for instance, but may be unaware whether the measurement is within normal range or whether it represents a potentially serious condition.

Certain embodiments of this disclosure describe a telemedicine system that can address some or all of the above concerns, among possibly others. The telemedicine system can advantageously guide patients through automated data collection and can facilitate live video chats with patient-selected health practitioners to discuss appropriate treatment and medications. The telemedicine system can act as a self-service point-of-care solution for patients outside of a traditional clinical setting. With the integrated capability to connect with their local clinician as needed, the telemedicine system can empower patients to proactively monitor their health status.

The telemedicine system can guide patients step-by-step to perform personal vital signs measurements. These measurements can be spot-check or continuous measurements, including, for example, one or more of oxygen saturation ($SpO_2$), pulse rate, perfusion index, and respiration rate from a pulse oximetry sensor, as well as optionally temperature or blood pressure. Other physiological parameters can also be measured using these or other sensors, such as heart rate from an ECG sensor, respiration rate from an acoustic sensor, or a hemoglobin measurement (such as SpHb, total hemoglobin; SpMet, methemoglobin; or SpCO, carboxyhemoglobin, all available from Masimo Corporation of Irvine, CA) from an optical sensor. Any subset of these or other measurements may be taken. The telemedicine system can summarize the patient's measurements, optionally indicating which measurements are outside of normal range (such as abnormally high temperature). After reviewing results, the patient may be prompted to select a local or remote clinician to consult in a telemedicine session.

If the patient would like to consult with a clinician, the telemedicine system can provide a list of care providers in the vicinity (or remote) that are available for live audio and/or video conferencing. The selected care provider may receive a copy of the patient's vital signs spot-check results and may provide a real-time, virtual consultation with the patient using the integrated audio and/or video feed. At the conclusion of the virtual consultation, the patient's prescription can be sent directly to the desired pharmacy and a copy of the results may be sent to the patient (e.g., via email).

Figure 17:
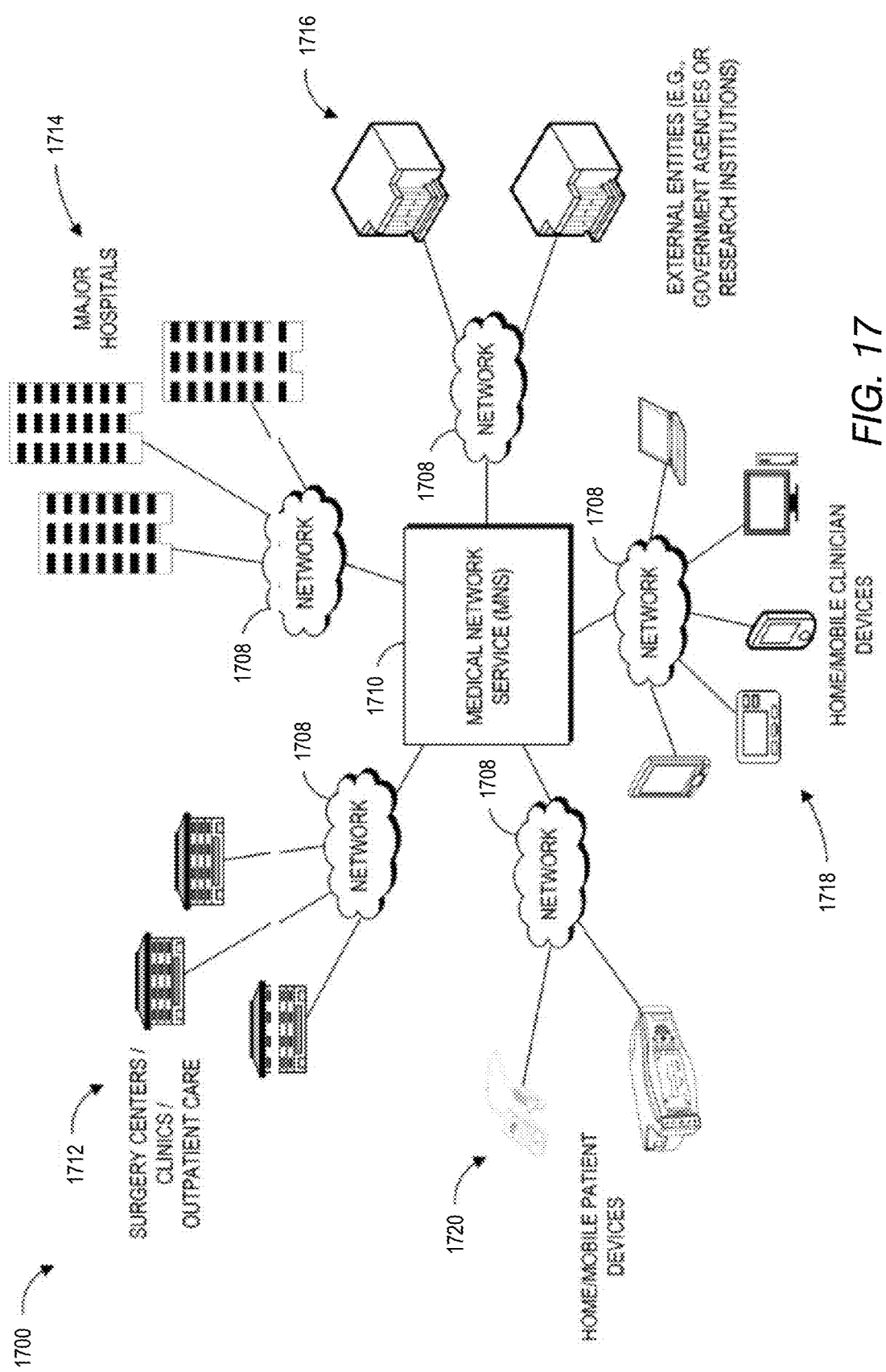
FIG. 17 illustrates an example diagnostic computing environment including a medical network service.

Features of the telemedicine system are described in detail below with respect to FIGS. 19 through 27. However, prior to describing these features in detail, a computing environment is described with respect to FIGS. 17 and 18, in which the telemedicine system can optionally be implemented. Turning to FIG. 17B, in a computing environment 1700, various computing devices and patient monitoring devices can obtain network services from a medical network service (MNS) 1710. Various institutions 1712, 1714, 1716 and devices 1718, 1720 are shown in the computing environment 1700. These institutions include surgery centers/clinics/outpatient care centers (collectively referred to herein as small clinics 1712), major hospitals 1714, external entities such as government agencies 1716. The example devices 1718, 1720 shown include home/mobile clinician devices 1718, and home/mobile patient devices 1720. The various institutions 1712, 1714, and 1716 may each include internal networks of devices having computing devices and patient monitoring devices that communicate over networks 1708 with the MNS 1710. The MNS 1710 can provide the users of the institutions 1712, 1714, and 1716 with access to a variety of features that are typically included in an internal IT network installation at a hospital, some examples of which include electronic medical records or EMR, paging systems, wellness index computational services, and the like. In addition, the MNS 1710 can provide patients and clinicians with access to a telemedicine system (described below with respect to FIG. 18).

The MNS 1710 can communicate with the home/mobile clinician devices 1718 over a network 1708 and the home mobile patient devices 1720 of a network 1708. The example networks 1708 shown can be local area networks (LAN), wide area networks (WAN), the Internet, an intranet, combinations of the same or the like. Any type of clinician computing device 1718 can communicate with the MNS 1710 including, for example, laptops, desktops, servers, work stations, tablets, wireless handheld devices such as cell phones, smart phones, personal digital assistants and wireless pagers, augmented reality devices, virtual reality devices, combinations of the same or the like. Likewise, the MNS 1710 can communicate with any type of patient monitoring device 1720 including bedside devices, body worn devices, telemetry devices, and the like. Any of these patient devices 1712 can output parameter data, trend data and/or alarms which can be provided to the MNS 1710 over the network 1708 and then re-routed by the MNS 1710 to institutions 1712, 1714, or computers thereof, and mobile clinician devices 1718.

In certain embodiments, by providing network services to the various entities shown, the MNS 1710 can provide greater reliability, security and therefore patient safety compared to existing networks in hospitals and other clinical facilities. The MNS 1710 may be implemented in one or more computing devices, such as servers, which may be geographically located, for example, in a data center, or which may be geographically disbursed, for example, in multiple data centers. The MNS 1710 can include enterprise-class networking capabilities of any state of the art or currently available data center today including, for example, load balancing features, failover features, intelligent network problem detection and resolution features, and the like.

Thus for example, one benefit that the MNS 1710 can provide in contrast with existing hospital networks is that if a switch or other network device were to fail at an existing hospital network, that network would then go down and deprive patients of necessary care. In contrast, in the MNS 1710, if a component such as a switch goes down, the MNS 1710 may be able to reroute network traffic through other switches and other components and continue or resume critical patient care services for the various institutions and devices shown.

Further, the MNS 1710 can be configured such that service level agreements (SLAs) can be provided to institutions so that guarantees of service can be met by the MNS 1710. An example SLA guarantee can be that alarms processed by the MNS 1710 can be provided to clinician devices in the institutions 1712, 1714 within a specified period of time, such as a few seconds or the like. The MNS 1710 may also provide uptime guarantees through SLAs or the like.

Moreover, by providing network services from the cloud, in certain embodiments, the MNS 1710 can provide synergistic effects that are greater than the benefits of simply moving the networking services out of the hospital and into a centralized data center. One example of a synergistic benefit of the MNS 1710 in certain embodiments is that patient profiles from different institutions or clinical facilities can be maintained by the MNS 1710 as a single patient profile. Thus, if a patient is in a first facility and has a profile that specifies alarm settings that are unique to that patient's health conditions, the MNS 1710 can store these alarm settings in the patient's profile in the cloud. If this patient subsequently is admitted to a different facility, the MNS 1710 can provide this second facility with access to the patient's profile, including the alarm settings that were previously set in the first facility. Patient profiles can enable clinicians to avoid having to re-establish useful alarm settings and/or other monitoring settings for the patient. Furthermore, the MNS 1710 can enable these patient profiles to be updated and customized at the second facility.

In addition to these features, in certain embodiments any of the data collected by the MNS 1710 can be anonymized and provided to the external entities 1716 including, for example, government agencies or research institutions for demographic and healthcare research purposes, additional examples of which are described below with respect to FIG. 18.

Figure 18:
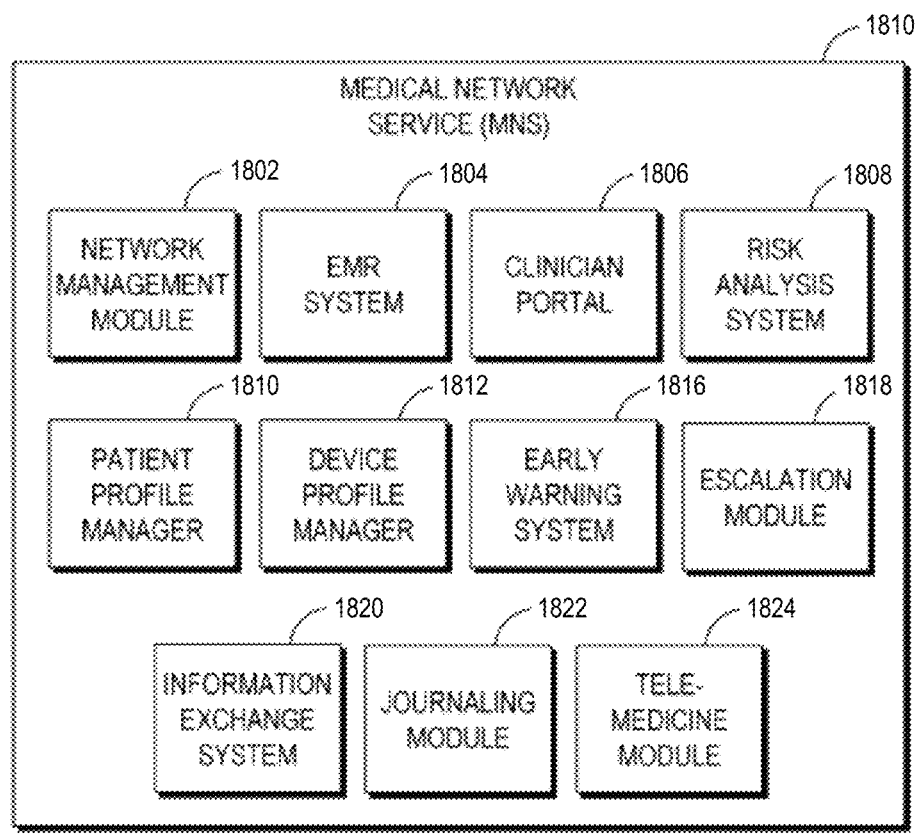
FIG. 18 illustrates an example implementation of the medical network service of FIG. 17.

Turning to FIG. 18, a more detailed embodiment of a medical network service (MNS) is shown, the MNS 1810. The MNS 1810 can have all of the features of the MNS 1710 described above. In the depicted embodiment, the MNS has several subsystems or modules that can be implemented in hardware and/or software, including telemedicine features (discussed below). The example modules or components shown group functionality of embodiments of the MNS 1810 together under logical descriptions. It should be understood, however, that the various modules and systems shown in the MNS 1810 or portions thereof could be implemented together in a single system. In addition, not all of the systems or modules shown need be implemented on the same computing device but could instead be implemented in separate computing devices. Any of the systems or modules shown could also be omitted in some embodiments.

The MNS 1810 includes, for example, a network management module 1802. The network management module 1802 can manage network communications with other networks, including networks in hospitals and other facilities as well as communications with mobile patient devices and clinician devices. For example, the network management module 1802 can communicate with devices in hospitals and outside of hospitals, or inside of facilities and outside of facilities. The network management module 1802 can provide the networking services described above with respect to FIG. 17, such as load balancing, failover, and the like. In addition, if a patient is monitored in a facility that communicates with the network management module 1802, and then the patient is discharged from the facility, the network management module 1802 can maintain connectivity with a body-worn or other mobile medical device associated with the patient, for example, over cellular or Wi-Fi links. Additional example features of the network management module 1802 are described below with respect to FIG. 6.

The MNS 1810 also includes an EMR system 1804 that can generally store patient data from any facility, including data collected from patient monitoring devices in patients' homes or while patients are mobile outside of their homes or out of facilities. For example, the EMR system 1804 can include such information as parameter values, trend values, alarm histories, patient demographic data, patient condition data including diagnoses, patient medical histories, and patient medications, among a variety of other patient data. The data in the EMR 1804 can advantageously be used by other components of the MNS 1810 as described below to improve patient care.

A clinician portal 1806 of the MNS 1810 can provide a user interface or user interfaces that can be accessed by clinicians via their clinician devices to monitor the health status of their patients for whom they are responsible. The clinician portal 1806 may, for example, be implemented in one or more web pages, mobile applications, or other network applications and may provide information about the wellness or relative wellness of each patient.

In one embodiment, a wellness score or index is computed for some patients by a risk analysis system 1808 of the MNS 1810, and the clinician portal 1806 can depict these wellness indices among other parameter data, trend data and alarms for patients. In one embodiment, the clinician portal 1806 facilities triaging patients by providing functionality for patients to be ordered or ranked based on their wellness scores or indices as computed by the risk analysis system 1808. Example features for computing wellness indices or risk assessments are described in U.S. Pub. No. 2014/0077956, filed Sep. 18, 2013, titled "Intelligent Medical Network Edge Router," U.S. patent application Ser. No. 14/030,360, the disclosure of which is hereby incorporated by reference in its entirety. For example, the risk analysis system 1808 can take into two or more parameters, such as any combination of the following parameters: oxygen saturation (e.g., $SpO_2$), respiratory rate, pulse rate, heart rate, total hemoglobin level, methemoglobin, carboxyemoglobin, blood pressure, ECG output, encephalography output, or the like. The risk analysis system 1808 can combine data from such parameters and reduce this data to a single value or data representation of the combination of those parameters. The single value may be, for example, an index or score that is on a scale of 0 to 10, where 10 may represent a most healthy state, while 0 may represent a least healthy state. Thus, such scores could be used to rank the relative health state or acuity of patient sicknesses and such numerical rankings can be output for presentation to clinicians in the clinician portal 1806, thereby enabling clinicians to quickly triage patients.

In certain embodiments, the risk analysis system 1808 also leverages aspects of the cloud-based infrastructure of the MNS 1810 to improve the wellness index calculation. For example, the risk analysis system 1808 may be able to access patient profile data from the MNS 1810 that comes from previous hospital visits or other clinical facility visits from a single facility or multiple facilities to compute historical wellness indices or to compute a current wellness index. The risk analysis system 1808 can also personalize the wellness index based on patient attributes stored in the EMR system 1804. For example, the risk analysis system 1808 can personalize which parameters are weighted more heavily in the combination of parameters that are output as a wellness index based on previous patient conditions listed in EMR system 1804. In currently available systems, different institutions typically do not share their EMR data, and EMRs therefore cannot be used to correlate patient data from multiple institutions together and thereby improve risk analysis and wellness indices. However, such advantages can be made possible in certain embodiments by the centralized cloud nature of the MNS 1810.

The MNS 1810 also includes a patient profile manager 1811. The patient profile manager 1811 can manage patient profiles, which can include information about patient demographics, patient alarm settings, including alarm settings from previous visits to potentially multiple different facilities, patient conditions and so forth, and example features of which are described in greater detail below with respect to FIG. 3. The MNS 1810 further includes a device profile manager 1812 that can manage and store device profiles for medical devices that interact with the MNS 1810 as well as optionally other computing devices. The profiles may have information about rules that can be used to track the usage of these devices as well as a variety of other features.

The MNS 1810 also includes an early warning system 1816. The early warning system 1816 can issue early warning alarms based on parameter measurements, indices such as the wellness index or other indices. The early warning system 1816 can look for patterns in patients to facilitate detecting never events, including events that should occur never or rarely, like a patient dying in bed without any intervention, particularly when a patient is home and would not ordinarily be under the care of a hospital or have access to a system like the risk analysis system 1808 or the early warning system 1816.

An escalation module 1818 of the MNS 1810 can provide functionality for escalating alarms from a first or primary care provider to a second or subsequent care provider in case the primary care provider is unavailable. However, the escalation module 1818 may also provide additional functionality such as obtaining information from a remote primary care provider and providing this information to a secondary local care provider who is local to the patient and can therefore intervene using the information provided by the first care provider.

An information exchange system 1820 of the MNS 1810 can facilitate communicating information about patients to government or research institutions 1718 described above with respect to FIG. 17. One scenario where patient information may be submitted (anonymously) to government or research institutions is where a disease outbreak has occurred. For example, information may be provided that indicates several patients in a hospital have come down with the flu. The information exchange system 1820 can report this occurrence to an external entity such as the CDC or the Center for Disease Control, or state or local government agency or national government agency or worldwide agency to alert such agencies other institutions of the potentiality of a disease outbreak. If multiple institutions are using the services of the MNS 1810, then such information about patient conditions can be correlated and provided to these institutions as described above. More generally, the information exchange system 1820 can provide data about changing patient conditions continuously or periodically to government or research organizations to enable such organizations to rapidly respond to changes in regional health issues.

Further, the data provided by the information exchange system 1820 can be valuable to government agencies or research institutions to determine the effects of local conditions on health conditions. It may be discovered, for instance, that patients that go to a specific facility or set of facilities in a region are afflicted with disease related to nearby coal mining which can be ascertained by research institution or a government agency that has responsibility over such activities. Accordingly, the information exchange system 1820 can provide value data that can provide reports that can be used by external entities to improve patient care.

A journaling module 1822 of the MNS 1810 can capture clinician interactions with medical devices that are in the institutions and/or that are in patients' homes or that are body worn in mobile situations. The interactions can include any type of button press, alarm setting change, RFID tag interaction, or the like and can be recorded for the purposes of determining clinician response times to alarms or other measures of the quality of a clinician's care. The journaling module 1822 can further leverage the centralized monitoring capabilities of the MNS 1810 to compare the quality of care as journaled or otherwise calculated amongst different institutions as an apples-to-apples comparison because some or all of the data from these institutions can be provided to the centralized MNS 1810.

Further, the journal module 1822 can facilitate comparing the quality of care between different units in a hospital or other facility including different floors or groups of clinicians or shifts, or the like. The journal module 1822 can also facilitate comparing similar groups amongst different facilities, such as an ICU group in two different facilities, and can thereby enable an organization to identify gaps or deficiencies of care in different facilities that can be corrected. This information can be provided in real time or near-real time so that adverse patient care outcomes can be quickly addressed, in contrast to the past where information about quality of care is often analyzed well after an adverse care event has occurred (or even after a patient has been discharged). Further embodiments of journaling and detecting clinician interactions with devices (including via RFID tags) are described in greater detail in U.S. Pub. No. 2014/0077956, filed Sep. 18, 2013, titled "Intelligent Medical Network Edge Router," U.S. patent application Ser. No. 14/030,360, the disclosure of which is hereby incorporated by reference in its entirety.

A telemedicine module 1824 of the MNS 1810—an embodiment of the telemedicine system described above—can facilitate telecommunications between clinicians and patients, including telepresence communications where clinicians can diagnosis, treat, or otherwise attend to the needs of patients remotely using audio visual systems or the like. For instance, the telemedicine module 1824 can facilitate audio and/or video communications between patients and clinicians. For example, using telemedicine software in a patient device, a patient can connect to the telemedicine module 1824 to communicate with a clinician using similar telemedicine software on the clinician's device. The telemedicine module 1824 may implement any audio and/or video protocols, including voice over IP (VoIP) protocols, to facilitate telemedicine communications between patients and clinicians. Yet in other embodiments, the telemedicine module can be implemented apart from the other features of the MNS. For example, telemedicine functionality described herein can be implemented through a server dedicated to telemedicine functionality, rather than the full panoply of functionality available through the MNS. Or, patient devices may perform point-to-point connections directly with clinician devices (and vice versa) using available networking protocols.

Figure 19:
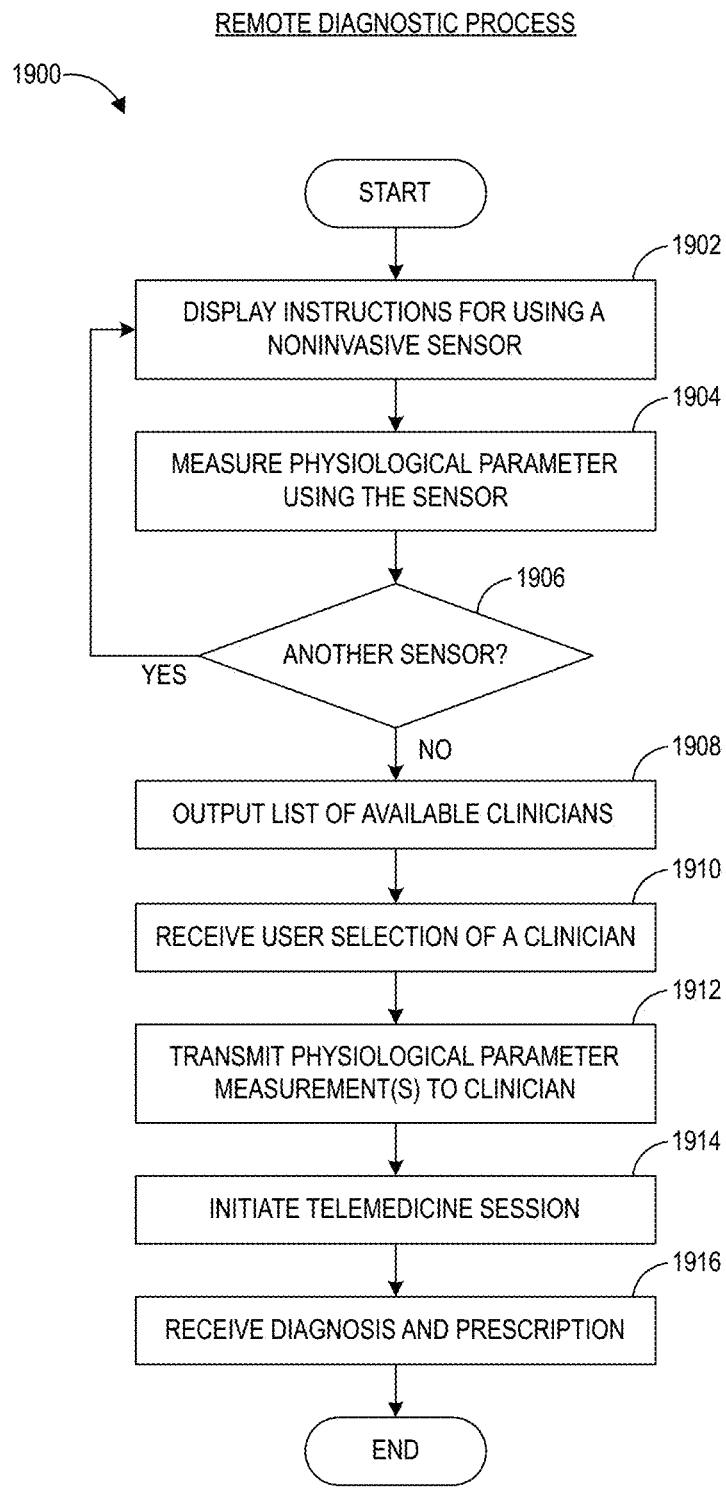
FIG. 19 illustrates an example telemedicine process that may be implemented in the diagnostic computing environment of FIG. 17 or in another diagnostic environment.

FIG. 19 depicts an embodiment of a telemedicine process 1900. The telemedicine process 1900 can enable a patient living at home or otherwise outside of a hospital to obtain a consultation from a remote clinician and can enable that patient to provide the remote clinician with physiological data to enable the remote clinician to make an informed decision about the patient's health condition.

The telemedicine process 1900 may be implemented at least in part by the telemedicine system or telemedicine module 1824, described above. Further, in an embodiment, the telemedicine process 1900 may be implemented using any of the patient monitors described herein. For example, the telemedicine process 1900 could be implemented by the pulse oximeter 300 of FIGS. 3A and 3B, the monitor 400 of FIG. 4, the monitor 502 of FIG. 5, or by the home/mobile patient device 1720 of FIG. 17.

In one embodiment, the device or devices implementing the telemedicine process 1900 need not be a dedicated patient monitor but instead can be an electronic device capable of executing software on a hardware processor that performs monitoring functions. Thus, for example, a phone, tablet, laptop, desktop computer, television, augmented reality device, virtual reality device, or the like can implement the remote diagnostic process 1900. For example, telemedicine software stored as program instructions in a memory of any such device can perform the telemedicine process 1900. This telemedicine software (not shown) can communicate with similar telemedicine software in a clinician device and optionally may do so through the telemedicine module 1824 of the MNS 1710/1810.

Referring again to FIG. 19, at block 1902, the telemedicine process 1900 displays instructions for using a non-invasive sensor. The instructions may be displayed in the form of a graphical user interface on a patient device which, as discussed above, may be a dedicated patient monitor or any electronic device. The instructions for using the non-invasive sensor can specify any of the following: how to open the sensor out of its packaging, how to place the sensor on the patient's body, how long to keep the sensor there, how to take a measurement, and so forth. Once the sensor is attached, the patient may indicate such in the user interface to inform the telemedicine module that the sensor is ready to take a measurement.

At block 1904, the telemedicine process 1900 measures the physiological parameter using the sensor. For example, software stored in the patient monitor or electronic device can access physiological signals output by the sensor and can process those physiological signals to calculate the physiological parameter or a plurality of physiological parameters. For example, the pulse oximeter 300 of FIG. 3 can receive optical signals from the sensor 304, which is an example of a sensor that can be used in the process 1900. The pulse oximeter 300 may include a signal processor 326 as well as other circuitry that can facilitate processing the signals received to calculate parameters of the patient.

Some examples of physiological parameters that may be calculated include oxygen saturation, pulse rate, perfusion index, pleth variability index (PVI), respiration rate, electrocardiogram parameters (ECG), electroencephalography parameters (EEG), blood pressure, temperature, as well as any other parameters described elsewhere herein. This list is not inclusive, as other physiological parameters may be measured and other types of non-invasive sensors may be used. Furthermore, in some embodiments, invasive or minimally invasive sensors may be used such as a finger-prick glucose sensor.

At block 1906, the process 1900 determines whether to obtain a reading from another sensor, and if so, loops back to block 1902. Otherwise, the process 1900 continues on to block 1908. For instance, if the process 1900 first displays instructions for using an optical sensor and then determines that a blood pressure measurement should be taken, the process 1900 loops back from block 1906 to block 1902. There, the process 1900 outputs instructions for using the blood pressure sensor and may then obtain the measurement from the blood pressure sensor in block 1904. The process 1900 may similarly loop back through blocks 1902 and 1904 to obtain temperature measurements and/or other measurements. In some embodiments, a single measurement is obtained, or a single non-invasive sensor is used from which multiple measurements may be obtained.

Although not shown, the process 1900 may also output the parameters calculated based on the measurements received or physiological signals received for display on the patient device or electronic device. Some examples of displays corresponding to the process 1900 are described below with respect to FIGS. 20 through 27. In other embodiments, the process 1900 sends the parameters directly to a clinician without showing them to a patient (instead, the process 1900 may output an indication such as "measurement done" or the like).

At block 1908, the process 1900 outputs a list of available clinicians. The list can include a list of local or remote doctors or clinicians. While in one sense, all clinicians may be remote to the patient in the sense that the patient device communicates with the clinicians over the network, local clinicians can be geographically closer to the patient than remote clinicians. The list of available clinicians may be generated based on publicly available information or information obtained from an insurance carrier of the patient such that the list of clinicians may include clinicians that are in a plan provided by the patient's insurer. Or alternatively, the list can include any clinicians who have signed up or otherwise opted to participate in a telemedicine program. The list may also include solely clinicians available to consult that moment, rather than all clinicians. The list may further include wait times for consulting with a particular clinician.

At block 1910, the process 1900 receives a user selection of a clinician from the list, and at block 1912, transmits the physiological parameter measurement or measurements to the clinician over a network (which may include the Internet). The transmission of the physiological parameter measurement or measurements to the clinician may be in the form of a message split into a plurality of packets sent over a network that implements any of the currently available network protocols today, such as the TCP/IP protocol. The parameters may be transmitted from the patient device through the MNS 1710/1810 described above and then provided to the clinician device. Alternatively, the parameter measurements may be provided directly from the patient device to the clinician device over the network.

At block 1914, the process 1900 initiates a telemedicine session with a clinician via audio and/or video. This can be a one-way or a two-way video session where the clinician and the patient see video of each other using currently available video communications protocols. The patient device may access video from the clinician and vice versa by way of accessing the telemedicine module 1824 described above. In this session, the clinician may have access to the physiological parameters measured previously. The clinician may use his or her professional skills to analyze the measured parameters. The clinician can talk with the patient about the measured parameters and about symptoms the patient is having in order to arrive at a diagnosis and optionally provide a prescription for the patient.

As described above, the telemedicine software installed on the clinician's device can enable the clinician to communicate with telemedicine software installed on the patient's device. The telemedicine software may be a dedicated application, such as a mobile application, or may be a web application accessible by a browser (or may be a combination dedicated and web application). During the initiation of the telemedicine session at block 1910, the telemedicine software on the patient's device may communicate a request to initiate a telemedicine session to the telemedicine software on the clinician's device. At the clinician's device, the telemedicine software may receive this communication and notify the clinician (e.g., audibly and/or visually) that the patient wishes to communicate with the clinician.

The telemedicine software may provide the clinician with the option (e.g., via a user interface) to accept or decline to communicate with the patient. In the event that the clinician uses the telemedicine software to decline the telemedicine session, the software may provide the clinician with an option to refer the patient to another clinician. If the clinician declines, for example, by selecting a user interface control from a user interface that provides the ability to do so, a decline message may be sent back from the clinician device to the patient device. If a decline message is received at the patient device, the telemedicine software at the patient device may output the decline message via a user interface.

However, in the depicted embodiment, at block 1916, the clinician provides a diagnosis and prescription, which are received at the patient device. The diagnosis may be received in the form of a message, and the prescription may be received in the form of a message. In addition, in some embodiments the prescription is sent directly from the clinician device to a pharmacy, where it may be filled and picked up or mail ordered to the patient. This prescription message, or any of the messages described herein, may also be communicated through the MNS 1710/1810.

Figure 23A:
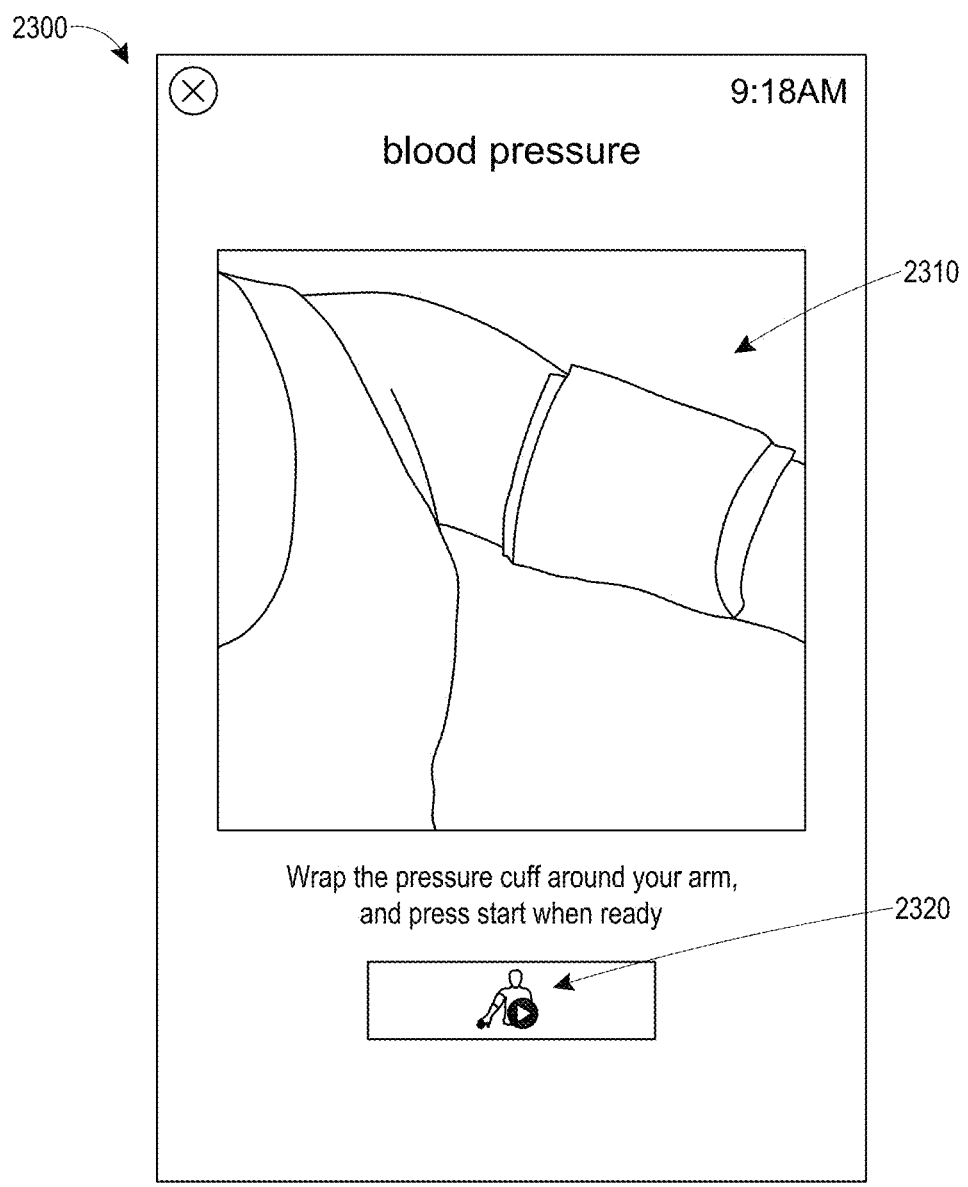
Figure 23B:
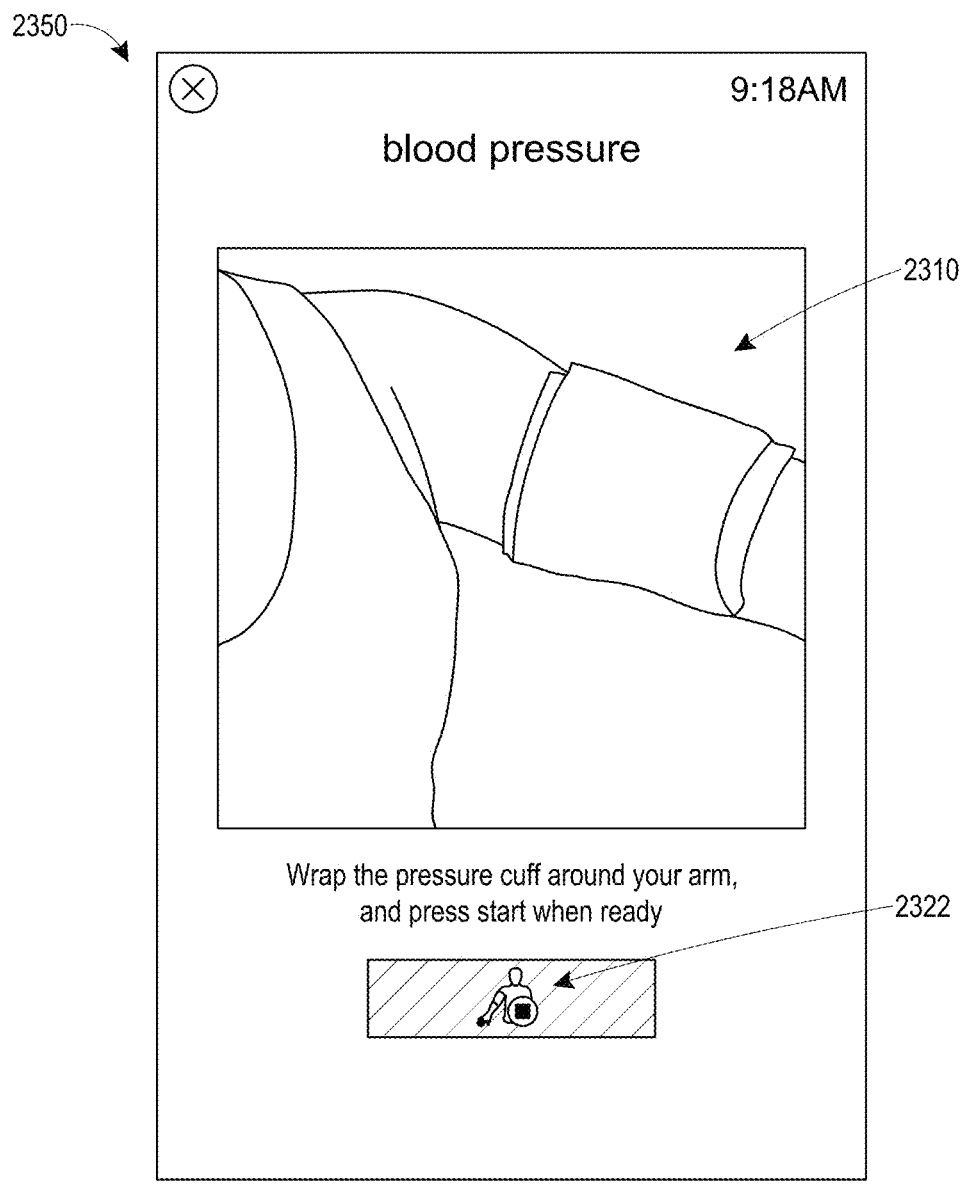
Figure 24:
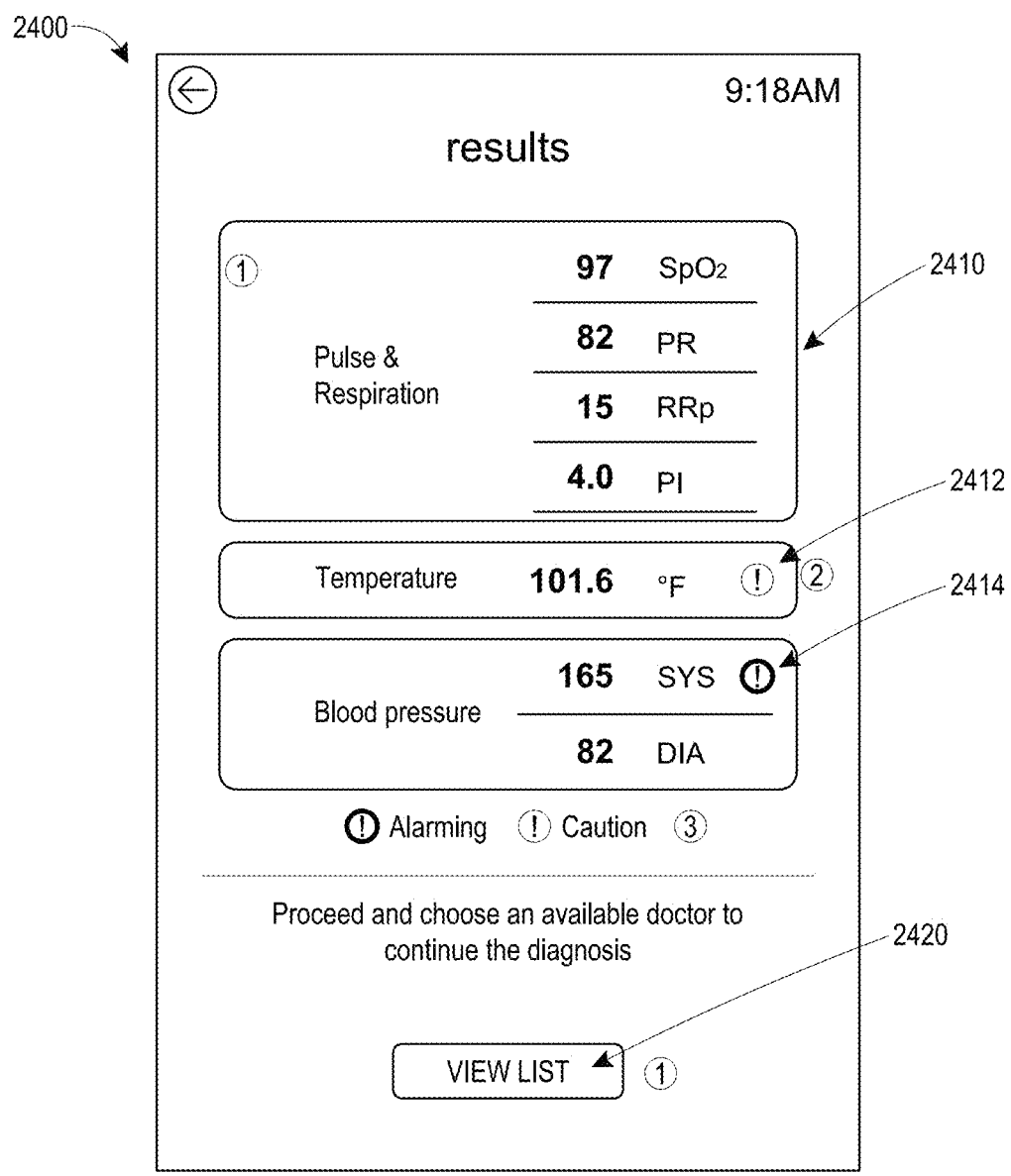
Figure 25:
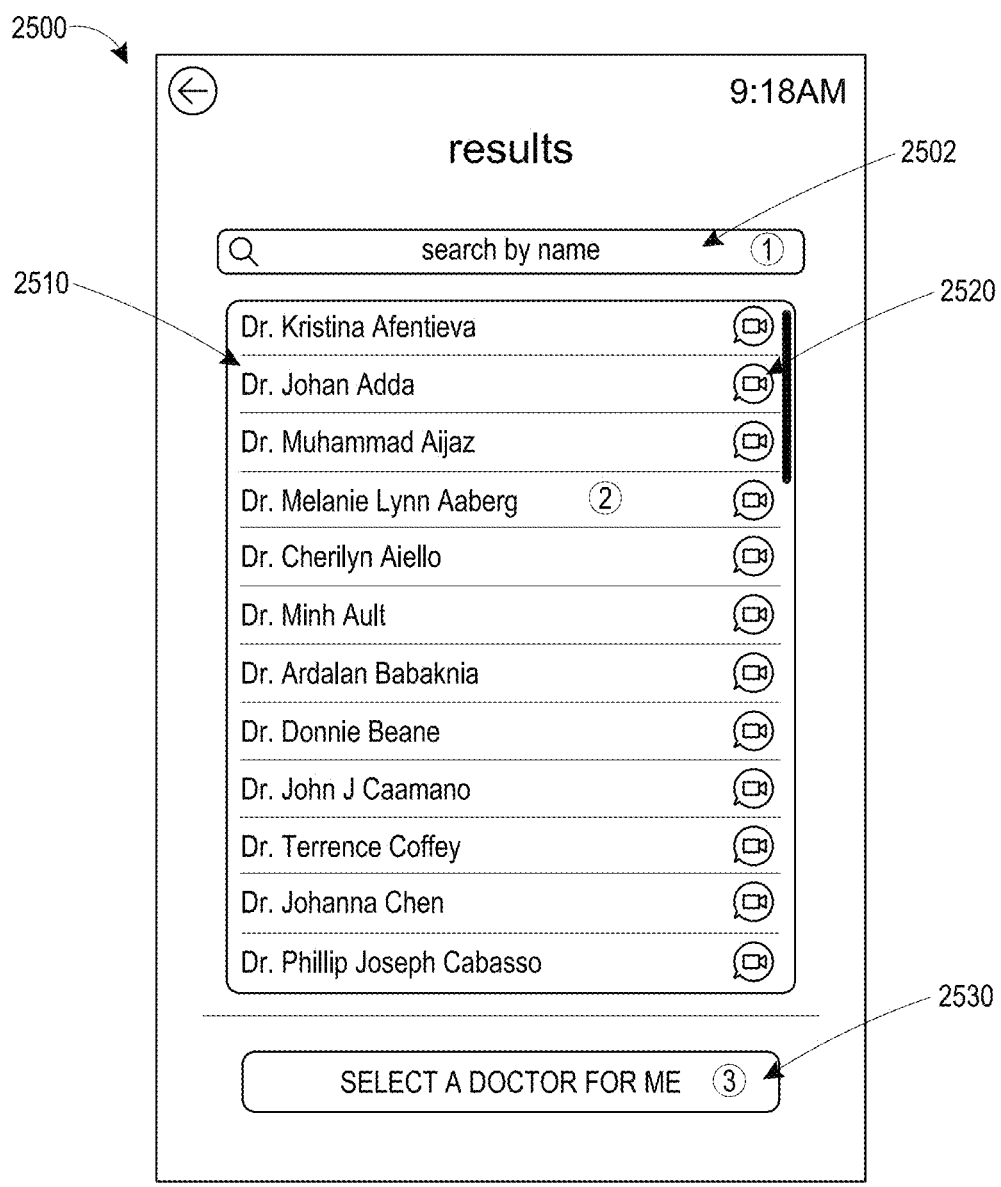

Turning to FIGS. 20-27, example user interfaces 2000-2700 are shown that may be output on the patient device described above with respect to FIG. 19. These figures depict many example features described above with respect to FIG. 19. For example, FIGS. 20, 21, 22, 23, and 24 provide various instructions to patients for obtaining measurements from non-invasive sensors. FIG. 25 depicts an optional user interface for selecting a doctor with whom to have a telemedicine session. FIG. 26 depicts a user interface of that telemedicine session. FIG. 27 depicts the result of the example telemedicine session, which is that a prescription has been sent to the user's pharmacy.

Each of the user interfaces shown includes one or more user interface controls that can be selected by a user, for example, using a browser or other application software (such as a mobile application). Thus, each of the user interfaces shown may be output for presentation by electronic hardware as graphical user interfaces, which may optionally include a browser or any other application software installed thereon that outputs the user interfaces. The user interface controls shown are merely illustrative examples and can be varied in other embodiments. For instance, any of the user interface controls shown may be substituted with other types of user interface controls that provide the same or similar functionality. Some examples of user interface controls that may be used include buttons, dropdown boxes, select boxes, text boxes or text fields, checkboxes, radio buttons, toggles, breadcrumbs (e.g., identifying a page or interface that is displayed), sliders, search fields, pagination controls, tags, icons, tooltips, progress bars, notifications, message boxes, image carousels, modal windows (such as pop-ups), date and/or time pickers, accordions (e.g., a vertically stacked list with show/hide functionality), and the like. Additional user interface controls not listed here may be used. Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input (e.g., finger or pen), game controller, or keyboard input, among other user interface input options. Although each of these user interfaces are shown implemented in a mobile device, the user interfaces or similar user interfaces can be output by any computing device, examples of which are described above.

In the depicted embodiment, each of the user interfaces shown is in the form of a tablet or phone display but may be implemented as different sized screens if used with a different type of patient device such as a dedicated patient monitor. The size may or may not be changed if used with a dedicated patient monitor. Each of the screens shown is a touchscreen in the depicted embodiment and therefore receives input from user touch, performing actions corresponding to those inputs. Touchscreens are optional, and other forms of input may be used in addition to or instead of a touchscreen.

Figure 20:
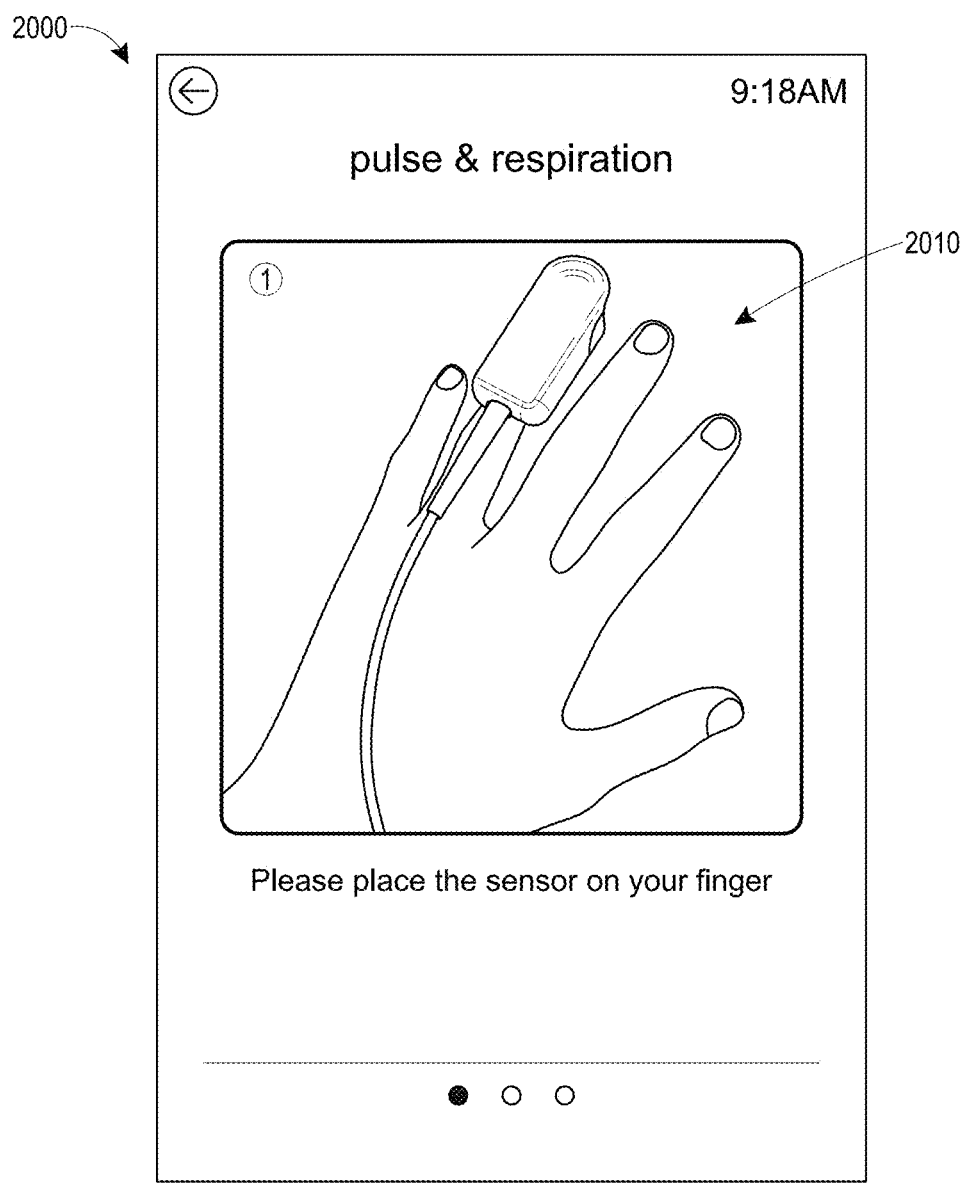
FIGS. 20 through 27C illustrate example user interfaces for instructing a patient to use patient monitoring equipment and for initiating a telemedicine session between the patient and a clinician.

Turning specifically to FIG. 20, an example user interface 2000 depicts instructions for a patient to place an optical sensor on the patient's finger to obtain measurements for pulse rate and respiration rate, among possibly other parameters. On the interface 2000, an image 2010 is shown of an optical sensor placed on an example hand. In this depiction, the optical sensor has a wire coming out of the sensor or cable coming out of the sensor that, although not shown, would connect to the patient device. Although not shown, the user interface may include instructions for connecting the sensor to the patient device in some implementations. For example, by swiping to the right on the user interface 2000 such instructions may be shown to the user.

The patient device may automatically detect when the sensor has been connected to the patient and connected to the monitor. In another embodiment, the user interface 2000 can include a user interface control (such as a button) that a user can select (e.g., press) to indicate that the user has placed the sensor in the indicated location, thereby informing the patient device to begin monitoring using that sensor. Once the user interface control is selected, the patient device may begin monitoring the output of the sensor and calculating one or more physiological parameters based on the sensor output.

Figure 21:
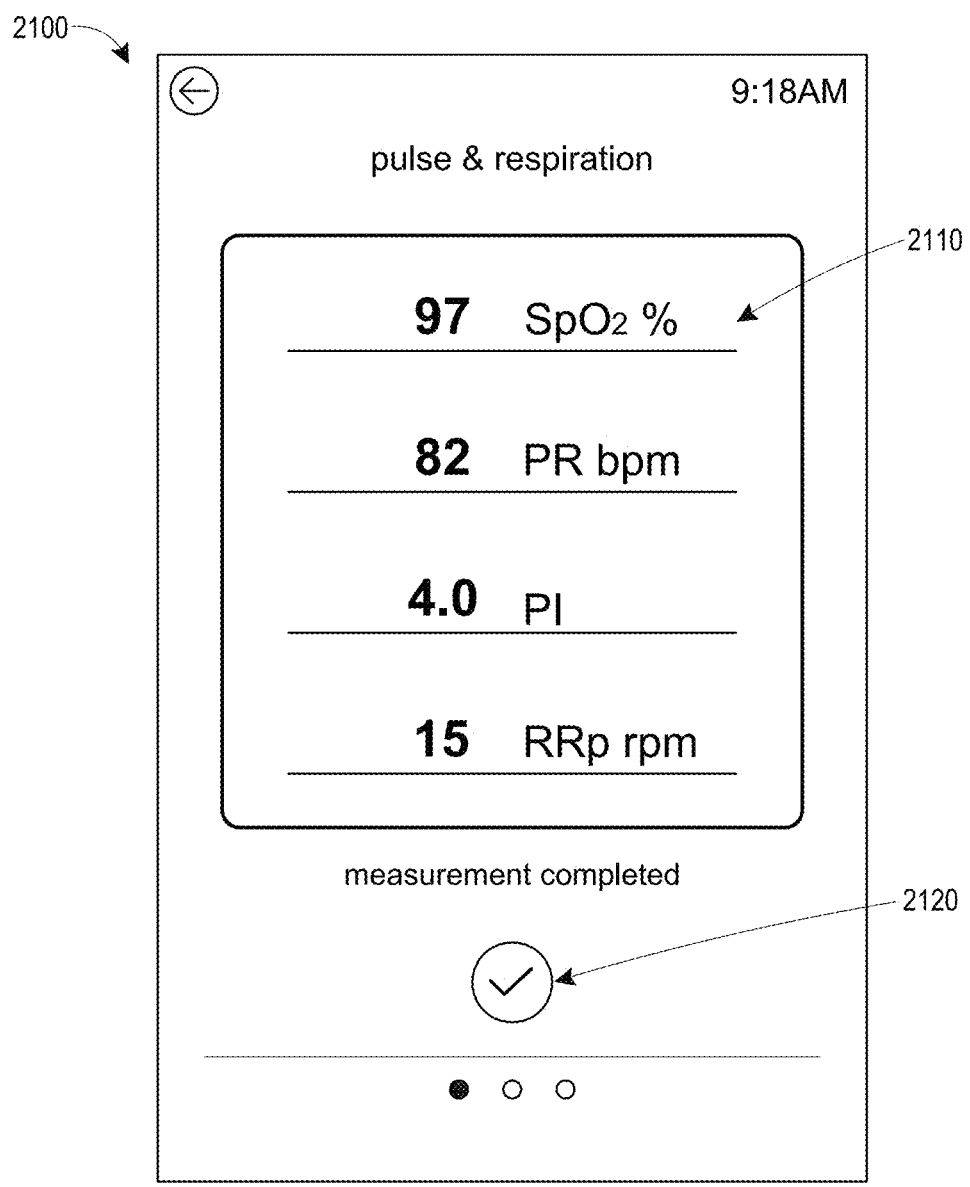

Turning to FIG. 21, a display is shown of user interface 2100 that includes example measurements 2110 of physiological parameters that were obtained using the non-invasive optical sensor shown in FIG. 20. Four measurements 2110 of physiological parameters are shown. These parameters including $SpO_2$, or oxygen saturation, PR or pulse rate, PI or perfusion index, and $RR_p$ or respiratory rate as determined from the photoplethysmograph (derived from optical sensor output). An indication that the measurement has been completed is also shown. In this embodiment, the measurement is a spot-check measurement. In other embodiments, the device may perform continuous measurements. An example user interface control 2120 in the form of a button is shown, which a user can select to move on to the next step. The next steps may include initiating a telemedicine session with a clinician to discuss the measured parameters, or prior to doing so, the next steps can include measuring additional parameters. This latter embodiment is shown in the following figures.

Figure 22:
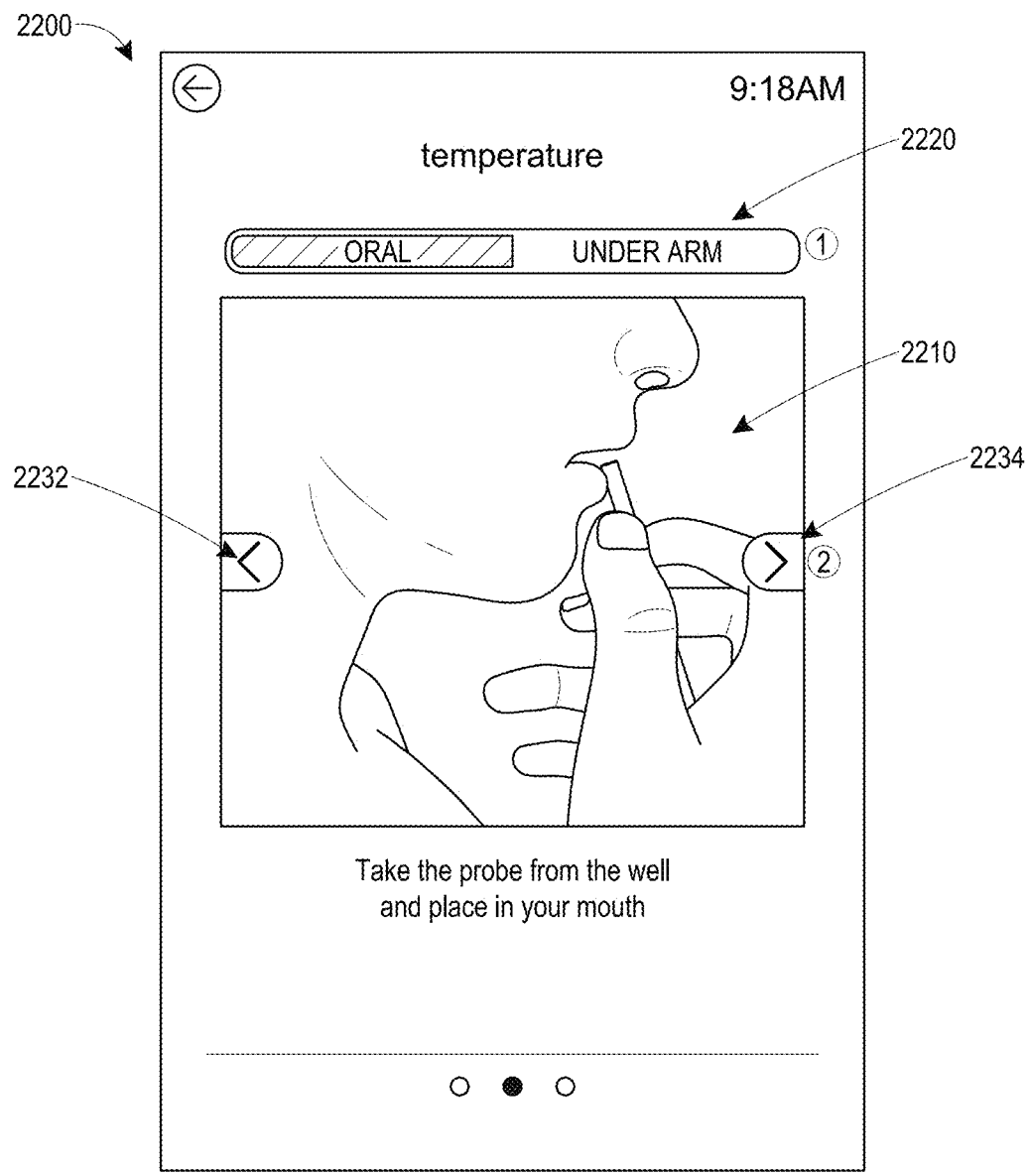

Upon selection of the user interface control 2120, a user interface such as the user interface 2200 of FIG. 22 may be output to the user. This user interface 2200 includes instructions for using a temperature sensor. A user interface control 2220 provides buttons that allow a user to select an oral or under-arm administration of a temperature sensor. Selection of one or the other of these two controls 2220 may cause the user interface 2200 to output different instructions for the use of the temperature sensor, whether oral or under the arm. The interface 2200 includes an image 2210 of a patient placing a temperature probe in the patient's mouth. Swipe indicators 2232 and 2234 show how the user can move backwards or forwards from one display to another, with different instructions on different displays.

The temperature sensor used may be one that is specifically provided for use with the patient monitor or may be a generic temperature sensor in other embodiments. The sensor may be wireless or wired and may communicate temperature measurements directly to the patient device. In another embodiment, the patient device outputs another user interface (not shown) that includes a text box that the patient can use to input the temperature reading into manually.

Turning to FIG. 23A, another user interface 2300 is shown that includes an image 2310 with instructions to attach a blood pressure cuff to a patient and text indicating that the patient should wrap the pressure cuff around the arm and press the start button 2320 when ready. Pressing this button 2320 shown can cause the cuff to inflate and can cause a pressure sensor embedded in the cuff to take a blood pressure measurement. The telemedicine software in the patient device can receive the blood pressure measurement through a wired or wireless connection with the cuff. FIG. 23B depicts a similar user interface 2350, which depicts a version of the user interface 2300 after the button 2320 has been depressed. The user interface 2350 depicts a similar button 2322, which when depressed, stops the cuff inflation and causes the cuff to deflate. This button 2322 can act as a safety feature should a patient experience pain when inflating the cuff. If the patient does not select the button 2322, the cuff may inflate and deflate normally, once the measurement is completed.

Turning to FIG. 24, a user interface 2400 is shown depicting results 2410 of the various measurements taken, including pulse and respiration results, temperature results, and blood pressure results. Example indicators 2412 and 2414 are shown, indicating the estimated severity of different measurements. The indicator 2412 is a caution indicator that indicates that a measurement—in this case temperature—is out of normal healthy range. The indicator 2414 is an alarming indicator which indicates cause for greater concern than the caution indicator because the measured value—in this case blood pressure—is farther out of range than would be the case for the caution indicator. These indicators can help a patient quickly determine which of the measured parameters are in poor condition and can help a clinician quickly identify areas for concern. In some embodiments, the caution and alarming indicators are omitted. Further, in addition to showing a list of several measurements in a single display, in some embodiments, individual measurements are displayed to a user after each measurement is taken (such as displaying a temperature measurement after taking a temperature measurement, pulse rate after taking a pulse rate measurement, and so on). These individual measurements may be displayed instead of or in addition to displaying the set of several measurements such as is shown in FIG. 24.

A user interface control 2420 in the form of a button provides the patient with the opportunity to view a list of clinicians. Selecting this control can cause a user interface 2500 shown in FIG. 25 or the like to be displayed. The user interface 2500 includes a list 2510 of available clinicians along with icons 2520 that the patient can select to request a telemedicine session with a clinician. A text box 2502 enables a user to search for a clinician by name, and a button 2530 can be selected to cause the telemedicine software to choose a clinician automatically for the patient. Selection of this button 2530 in one embodiment selects a clinician who is currently available and/or is in closer local proximity to the patient relative to at least some other clinicians.

Figure 26A:
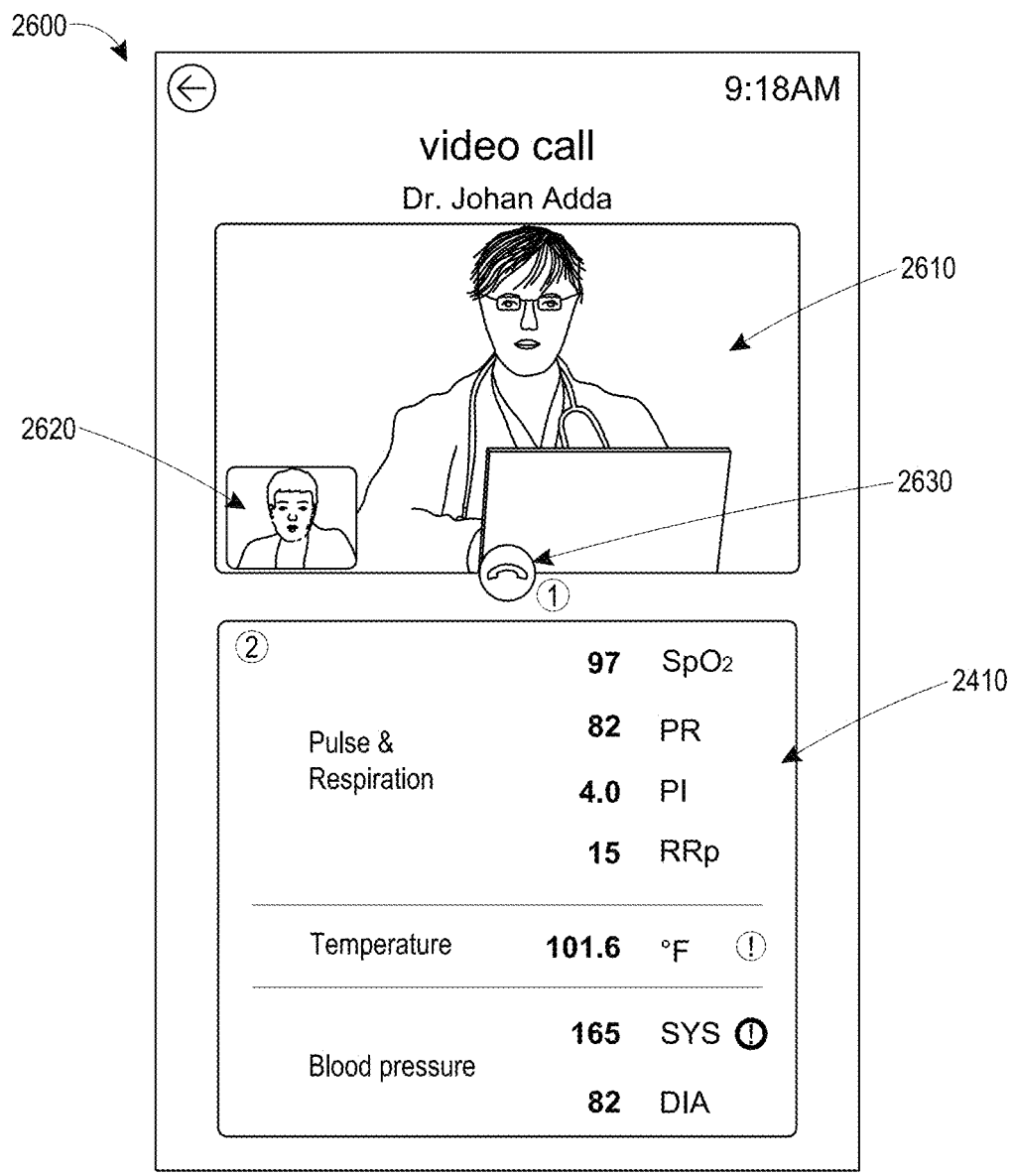

FIG. 26A shows an example user interface 2600 where, after a selection of a clinician in FIG. 25, a patient is now having a telemedicine session with the selected clinician. The interface 2600 includes a video display 2610 of the clinician with an (optional) inset video display 2620 of the patient. These videos may be obtained from cameras available in the patient device and the clinician device or from a separate camera. A button 2630 provides an option for the patient to hang up or end the video call. In the lower half of the user interface 2600, physiological parameter measurements 2410 obtained in the previous figures are displayed for viewing by the patient and clinician.

The clinician may have a substantially similar display as that shown or a different display than the patient. For instance, the clinician's display may include a larger view of the patient and an inset view of the clinician. The clinician's user interface may also provide the clinician with access to an electronic medical record of the patient to view historical data obtained from the patient.

Figure 26B:
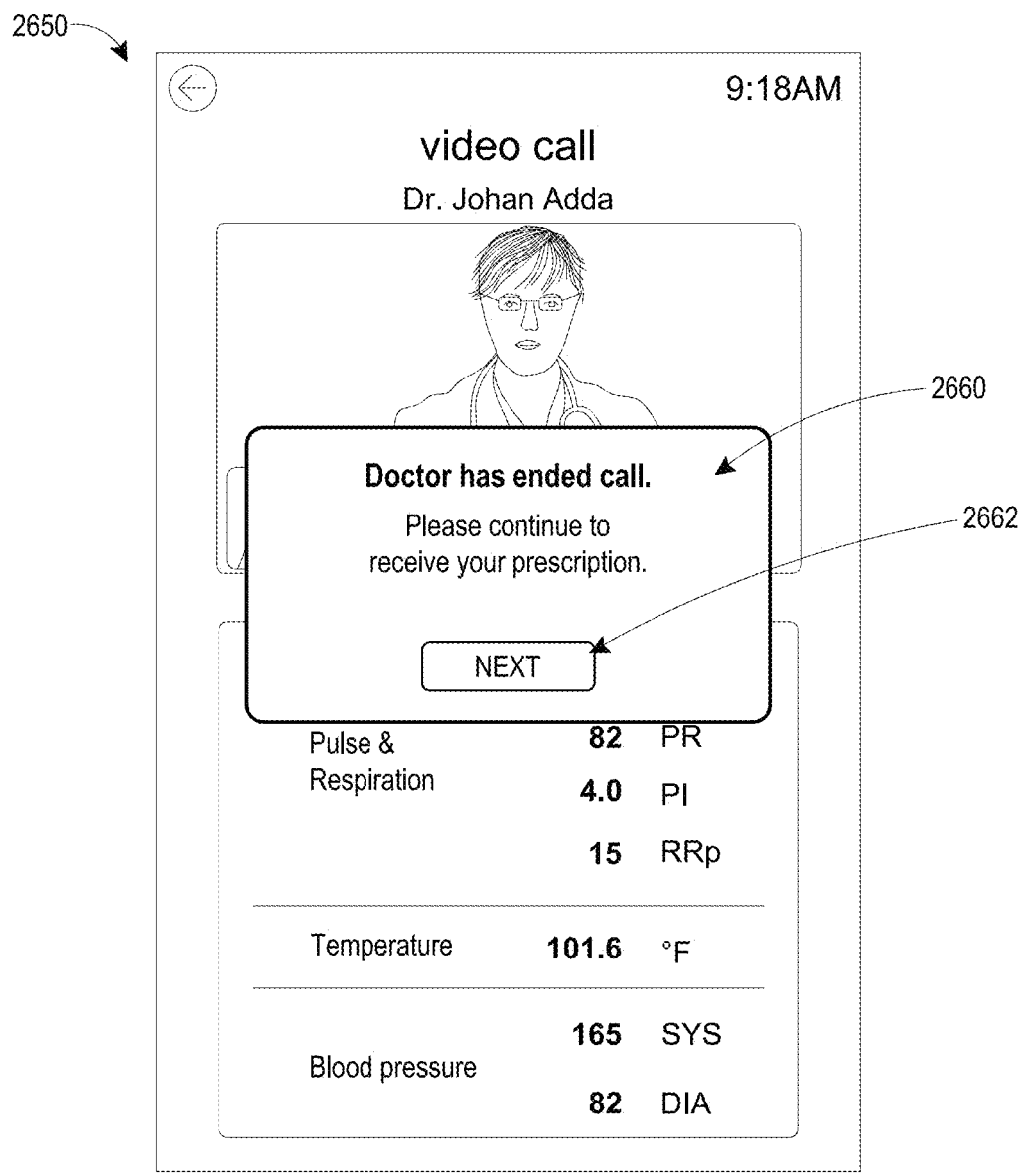
Figure 26C:
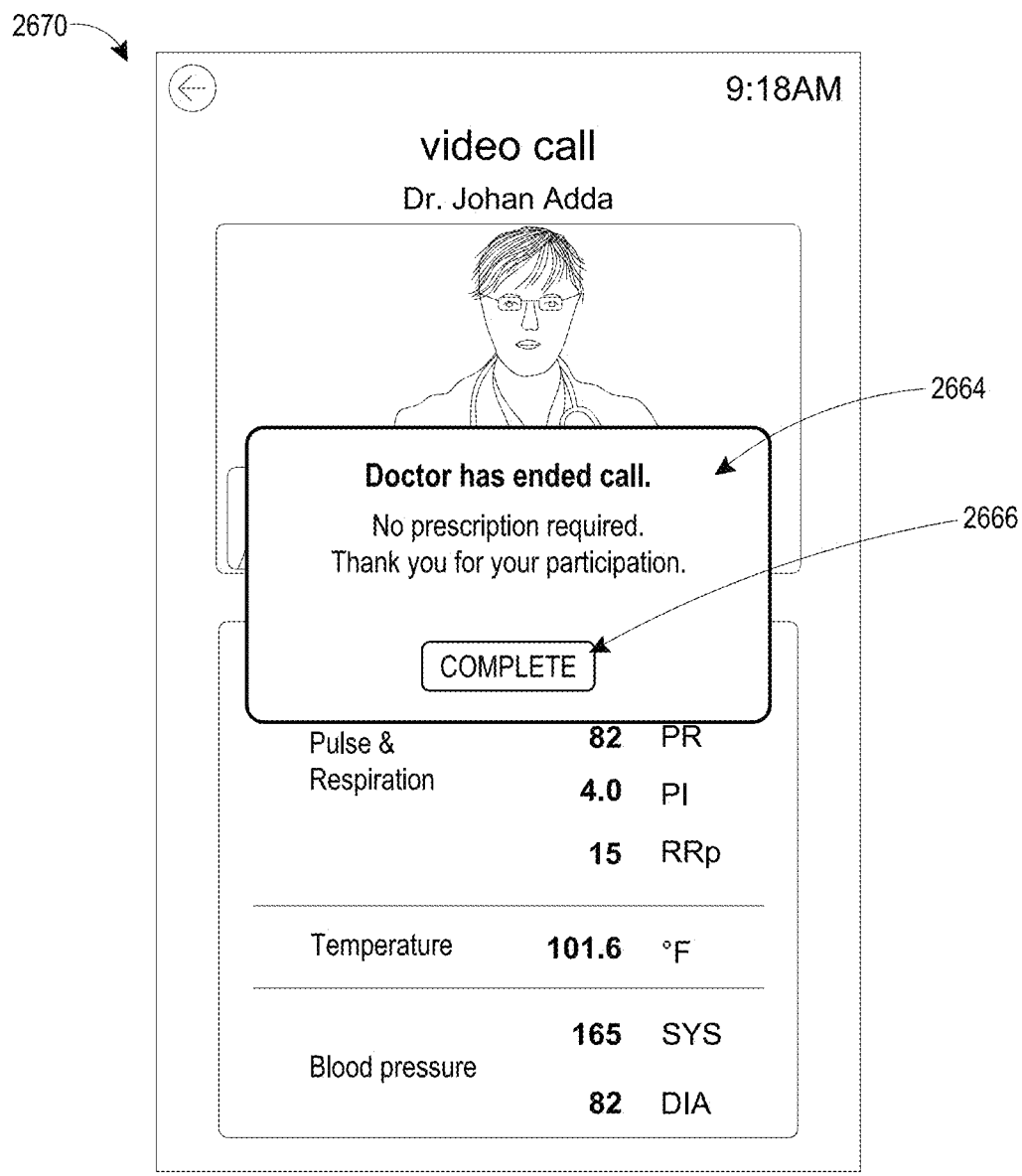

FIG. 26B shows an example user interface 2650 with a message 2660 indicating that the doctor has ended the call and that a "next" button 2662 should be selected to receive a prescription. User selection of this button 2662 can cause the telemedicine system to place an order for a prescription (specified by the doctor) at the patient's current pharmacy (details of which may be stored with the telemedicine system) or at another pharmacy (see, e.g., FIG. 27B). FIG. 26C shows another example user interface 2670 that, like the interface 2650, indicates that a doctor has ended the call with the patient with a message 2664. In this example, the message 2664 indicates that no prescription was necessary. Accordingly, a "complete" button 2666 may be selected by a user to complete the telemedicine session without a prescription order.

Figure 27A:
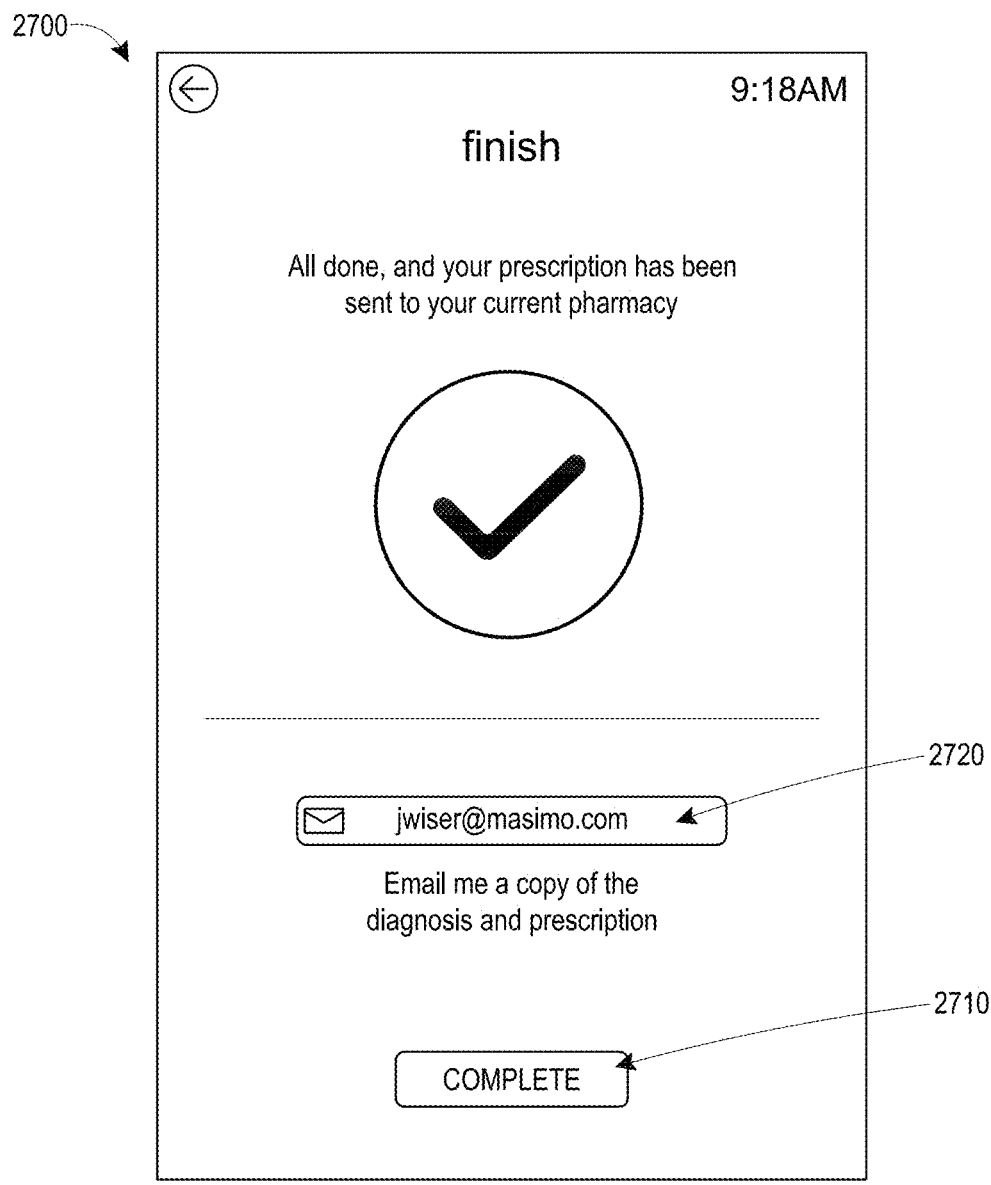
Figure 27B:
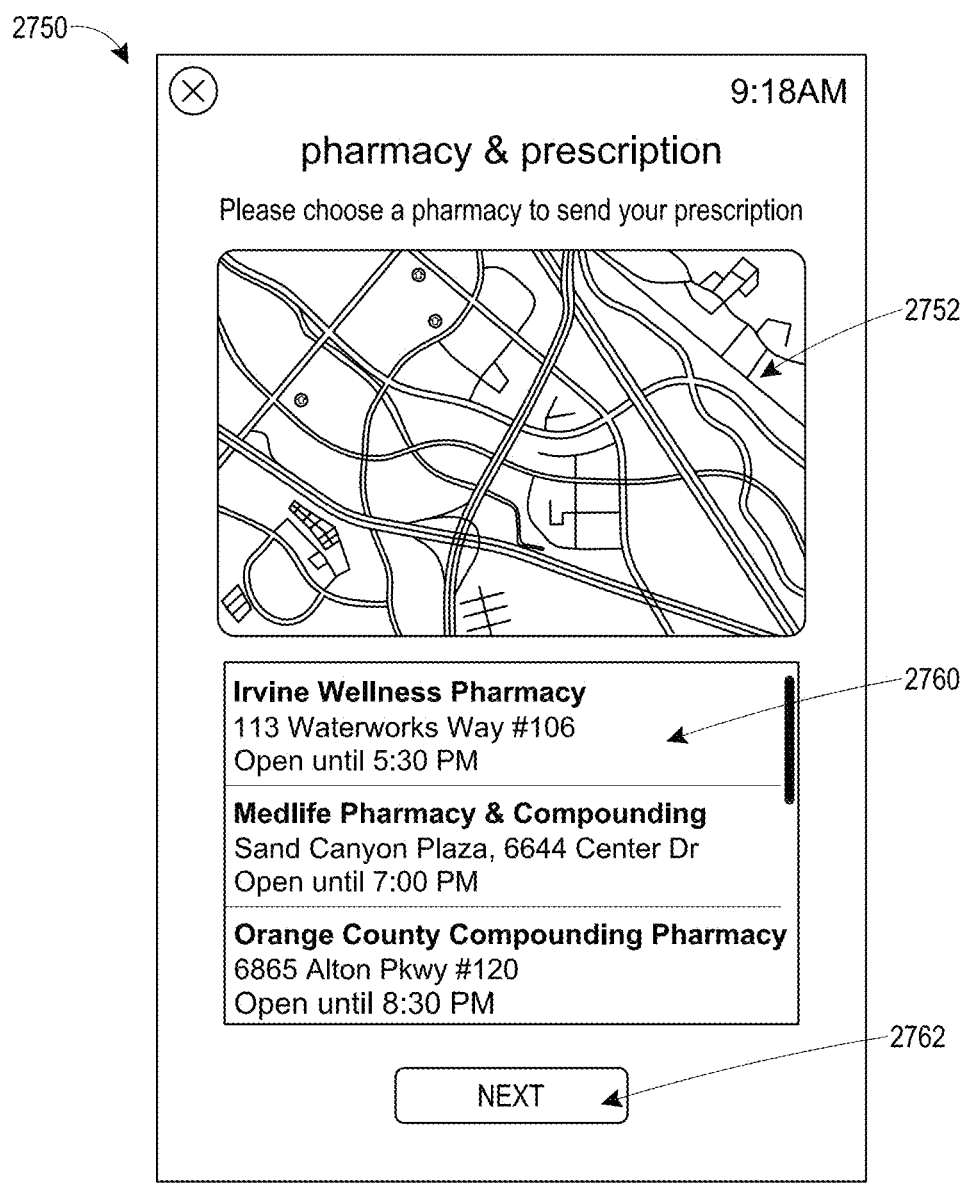
Figure 27C:
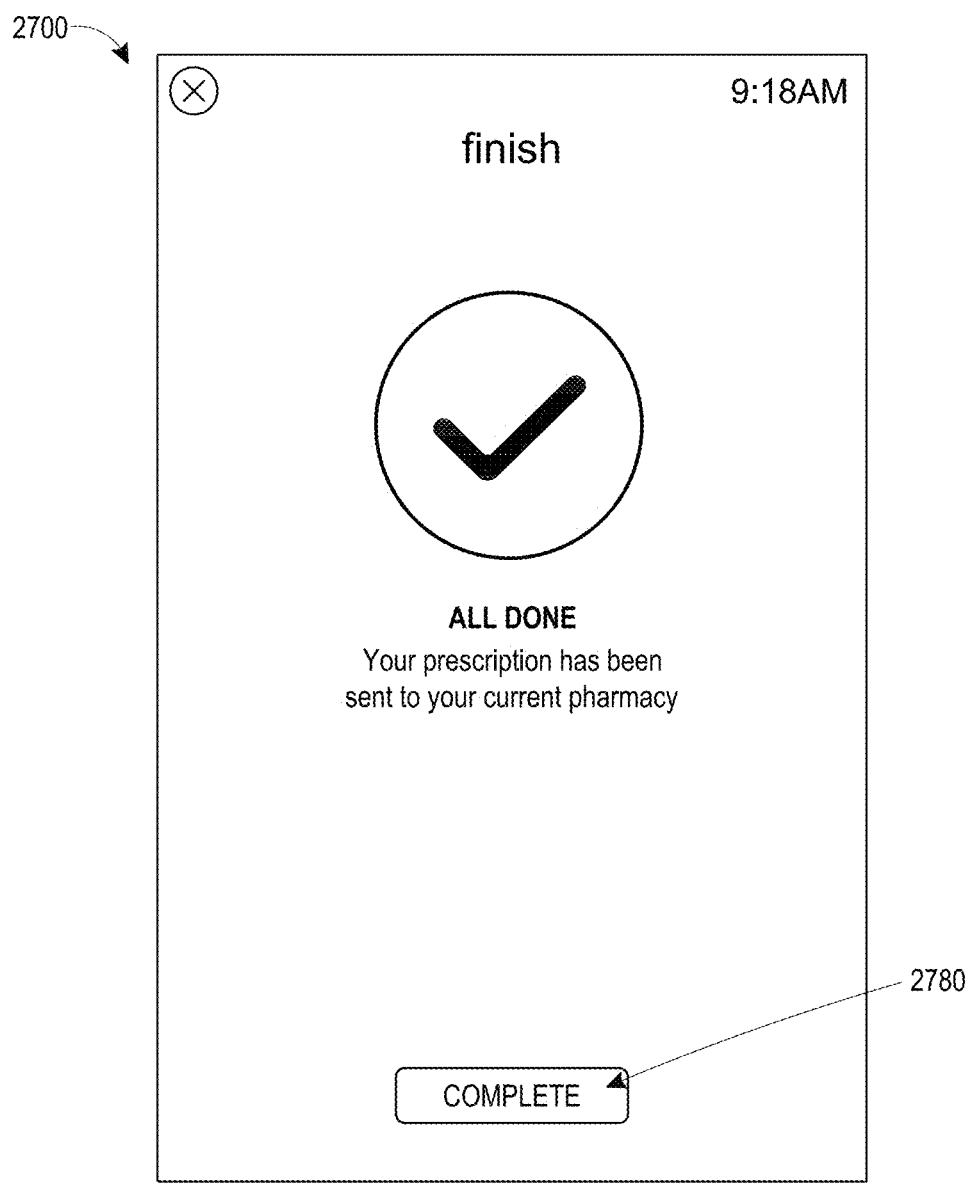

Turning to FIG. 27A, a finished user interface 2700 is shown that explains that the telemedicine session of FIG. 26 has completed. Further, the user interface 2700 explains that a prescription has been sent to the patient's current pharmacy. A user interface control 2710 in the form of a button enables the patient to complete the process. A user interface control 2720 can be selected by the patient to email a copy of the diagnosis and prescription to the patient. FIGS. 27B and 27C depict alternate embodiments of user interfaces 2750, 2770 that can be used to order a prescription and complete the telemedicine process, respectively. In FIG. 27B, a map 2752 is shown along with a list 2760 of pharmacies associated with the map 2752. A user may select one of the pharmacies from the list 2760 or from the map 2752 to have the doctor's prescription sent to that pharmacy. In one embodiment, not shown, the user interface 2750 can provide the user with functionality to search for nearby pharmacies, a specific pharmacy, or pharmacies near a certain address. Selecting a "next" button 2762 after selecting the pharmacy causes, in one embodiment, the user interface 2770 of FIG. 27C to be shown. The user interface 2770 informs the user that the prescription has been sent to the user's selected pharmacy and provides a button 2780 that, when selected, completes the telemedicine process.

In still other embodiments, the telemedicine system described may be implemented in a kiosk at or near a pharmacy. In such an embodiment, instead of the prescription being sent to the user's current pharmacy or a pharmacy of his or her choosing, the telemedicine system can send the prescription to the pharmacy at or near the kiosk. Of course, the kiosk may give the user the option to send the prescription to another pharmacy in other embodiments. For instance, the telemedicine system may output a user interface that includes a button (or the like) that says "send prescription here," as well as optionally another button (or the like) that says "choose pharmacy."

In certain embodiments, the telemedicine software at the clinician device can alert the clinician that one or more of the measurements should be re-run. As discussed above, the signal quality of some measurements may be low in certain circumstances. The telemedicine software at the patient device can convey signal quality data to the clinician device, or can convey an indication that the signal quality is low and thus, a measurement should be re-taken. The clinician can ask the patient to re-run one or more measurements to obtain better data. In another embodiment, the telemedicine software at the patient device can automatically analyze signal quality data and alert the patient to re-take one or more measurements.

Additional Telemedicine Embodiments

As described above, the telemedicine software installed in the patient device can provide a user with instructions for using a noninvasive sensor or sensors. In some embodiments, these instructions may be in the form of video, rather than (or in addition to) in the form of images and text as described above. The telemedicine software may include storage videos describing various aspects of how to use one or more noninvasive sensors. The storage videos can include videos instructing a user had to set up a sensor, how to take a reading with the sensor, and what to do if a sensor error occurs. Such error handling videos may be automatically activated if monitoring software in the patient device detects an error condition with the sensor.

For example, if a sensor probe is misaligned on the patient or falls off of the patient, the patient monitoring software in the patient device can detect this probe misalignment or probe off condition. Any suitable algorithm for detecting probe misalignment or probe off conditions may be used, as are currently available in the art. The patient monitoring software can notify the telemedicine software of this error condition. In response, the telemedicine software can output a message on the display of the patient device. The message may be a text message, an image, or a video instructing the patient how to address the error, such as how to properly position the sensor.

Images or videos used by the telemedicine software may be stored in different versions to match the age, gender, and/or ethnicity of the patient to promote patient comfort with the telemedicine software. For example, male, female, child, adult, senior, and different ethnic varieties of videos or images may be included. Likewise, text of the software output to the user may be presented in any number of different languages, which may be user-selectable.

As a result of the text, images, or video output by the telemedicine software, the telemedicine software can give the user sufficient information to take the necessary steps at home or away from the hospital to obtain accurate measurements to send to a doctor for review.

The information sent from the telemedicine software in the patient device may be provided to the doctor either live or off-line. In other words, the live telemedicine session described above is optional, and in another embodiment, the measurements obtained from the telemedicine module may be sent over a network to a clinician, who may review the measurements at a separate time and message the patient regarding the clinician's diagnosis instead of doing a live video session. In one embodiment that employs this off-line feature, the telemedicine software may also output one or more text input fields (such as text boxes) they give the patient the ability to describe symptoms that are bothering the patient so as to enable the clinician to make a better-informed diagnosis. Just as in the live telemedicine session embodiments described above, the clinician can transmit, from the clinician device, a prescription to the patient's pharmacy and/or directly to the patient.

Moreover, in one embodiment, the telemedicine software on the patient device can include audio or video recording functionality that records a patient's description of his or her condition. The telemedicine software can store this audio or video and transmit it to the clinician device, so that the clinician can review it asynchronously, e.g., at a different time instead of live.

Additional CCHD Embodiments

Figure 28:
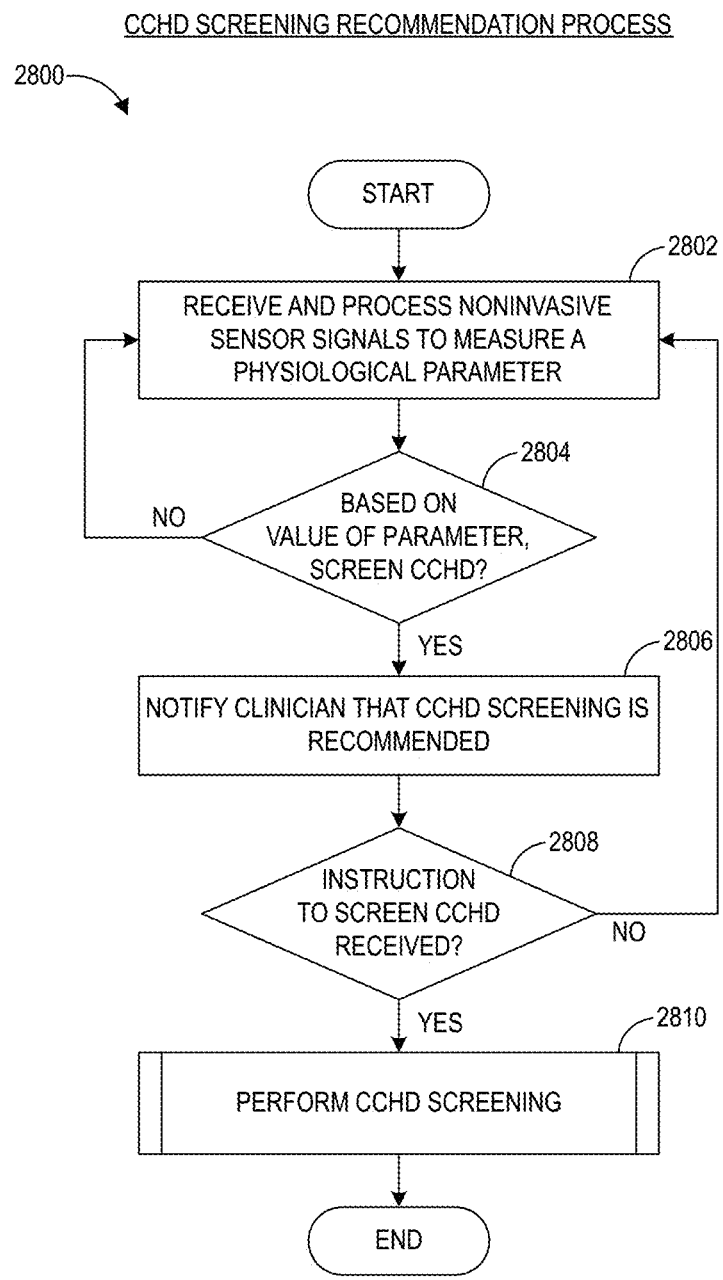
FIG. 28 illustrates an embodiment of a CCHD screening process.

FIG. 28 depicts an embodiment of a CCHD screening recommendation process 2800. Like the process 1900 described above, the process 2800 may be implemented by any of the patient devices or electronic devices described herein, including by devices described below respect to FIG. 29. The CCHD screening recommendation process 2800 can advantageously determine whether a patient is a candidate for CCHD screening or rescreening. For instance, although a patient may have been screened for CCHD already, the CCHD condition may have been missed, and the patient's physiological measurements may deteriorate.

The process 2800 can monitor physiological parameter values, including any of the parameters discussed herein, and determine whether those parameter values indicate that CCHD rescreening would be desirable. If screening was not previously performed, the process 2800 may have a similar effect in recommending screening based on measured physiological parameter values.

At block 2802, where a process 2800 receives and processes a non-invasive sensor signal to measure a physiological parameter. Any physiological parameter discussed herein may be used, such as oxygen saturation. At block 2804, based on a value of the parameter, the process 2800 determines whether to recommend CCHD screening or rescreening. If not, the process 2800 loops back to block 2802, where the patient device continues to monitor physiological signals obtained from the non-invasive sensor.

However, if screening of CCHD is recommended, then the process 2800 moves on to block 2806, where the process 2800 notifies one or more clinicians that CCHD screening is recommended. If a clinician then instructs CCHD screening to be performed at block 2808, then at block 2810 CCHD screening is performed using any of the methods described herein. Otherwise, the process 2800 loops back to block 2802, where the patient's physiological parameters continue to be measured.

Figure 29:
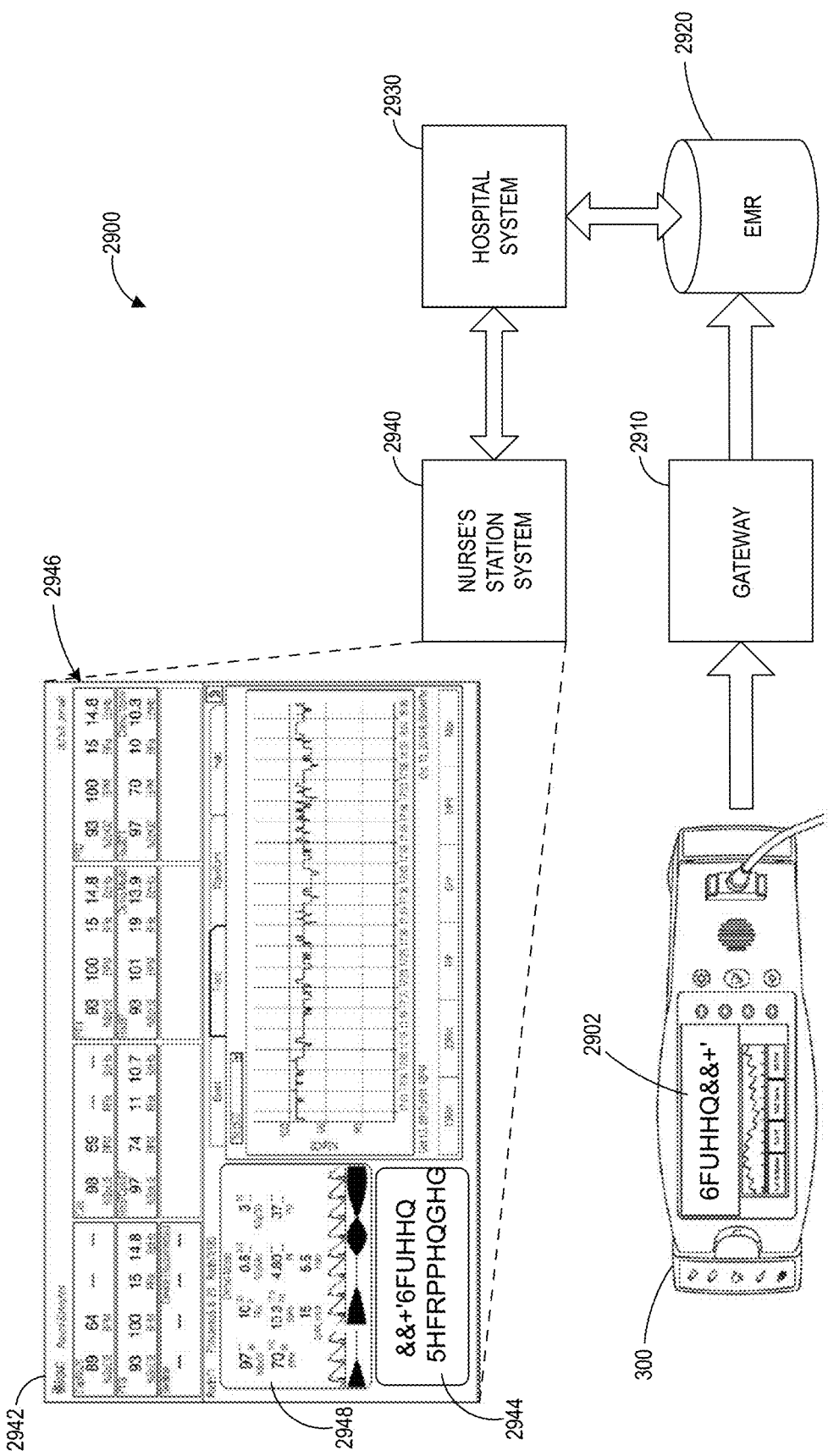
FIG. 29 illustrates an embodiment of a CCHD screening environment.

The process 2800 can be used in the context of a computing environment 2900 shown in FIG. 29. The computing environment 2900 of FIG. 29 includes a patient monitor 300 in communication with a gateway 2910, which is in communication with an EMR 2920. The EMR 2920 is in communication with a hospital system 2930, which is in communication with a nurse's station system 2940.

The patient device 300 is an example representation of any of the patient devices discussed herein. The gateway 2910 may be a server or appliance that collects data from multiple patient monitors and forwards that data to the EMR 2920. The EMR 2920 is an example electronic medical record database that stores patient medical data. While an EMR is illustrated in the example of FIG. 29, in various other implementations the EMR 2920 may comprise any database system or data ingestion layer, such as a national database system, or the like. The hospital system 2930 may be a server or set of servers in communication with the nurse's station system 2940 as well as in communication with other nurse's station systems throughout the hospital. The hospital system 2930 may manage electronic scheduling for clinicians as well as paging or other features. The gateway 2910 and the hospital system 2930 may be part of the same system in one embodiment. In some implementations, the hospital system 2930 (and including the nurse's station system 2940) are optional or not included, and the patient device 300, gateway 2910, and EMR 2920 function as otherwise described herein. Although not shown, the various devices and systems shown can communicate across a network.

The patient device 300 can be in communication with one or more non-invasive sensors coupled to a patient (not shown). The patient device 300 can be used for continuous or spot check monitoring of one or more physiological parameters. The patient device 300 may include hardware and software that processes physiological signals received from the one or more non-invasive sensors to determine whether the patient is a candidate for a CCHD screening or rescreening, as set forth in the process 2800.

Commonly, many infants are screened for CCHD initially about 24 hours after birth. While many infants may pass the test, at some point in time later, an infant's condition may deteriorate, indicating that the infant should be rescreened. Thus, the patient device 300 can look for such conditions. One example of such a condition is when the infant's oxygen saturation level drops below a certain value, for example 95%. With reference again to the process 2800 of FIG. 28 at block 2804, if the value of oxygen saturation is too low (e.g., below a threshold), then the patient device 300 shown in FIG. 29 may recommend that CCHD screening or rescreening be performed for the patient.

This recommendation may be provided to clinicians in one or more ways. As shown, a recommendation 2902 to rescreen for CCHD can be displayed on the patient device 300. In addition, the patient monitor 300 can communicate a recommendation to rescreen to the hospital system 2930 across the network so that clinicians not close to the patient monitor can be informed. The recommendation can also be provided directly to clinician devices (see, e.g., FIG. 18) over the network.

The recommendation provided to the hospital system 2930 can pass through the gateway 2910 to the EMR 2920 to the hospital system 2930, or directly from the gateway 2910 to the hospital system 2930. The hospital system 2930, upon receipt of the recommendation, which can forward this recommendation on to the nurse's station system 2940. The nurse's station system 2940 receives the recommendation from the hospital system 2930 and may output the recommendation on a display 2942. The display 2942 includes data 2946 corresponding to a plurality of patients as well as detailed data 2948 corresponding to a specific patient. The screening recommendation 2944 corresponds to the detailed data 2948 for the particular patient in this embodiment.

The recommendation 2944 may be in the form of a popup or other user interface control, and it may be selectable such as by a mouse or a touch input. Selection of the recommendation 2944 may cause the display 2942 to show data that went into the screening recommendation, such as the oxygen saturation, pulse rate, profusion index or respiratory rate value or values that caused the patient device 300 to recommend CCHD screening. By supplying these values along with the recommendation, the patient device 300 can enable a nurse at the nurse's station system 2940 to evaluate whether or not to perform CCHD screening or rescreening.

The nurse or other clinician may determine the CCHD screening is warranted and send a notification from the nurse's station system 2940 to the patient device 300 and/or to a clinician device or devices over the network (not shown) to enable one or more clinicians to participate in CCHD screening or rescreening.

Alternatively, the hospital system 2930 can automatically schedule a rescreening in response to receiving the rescreening recommendation from the patient device 300. The hospital system 2930 can communicate the scheduled rescreening to the nurse's station system 2940, which can output the scheduled rescreening on the display 2942.

Figure 30:
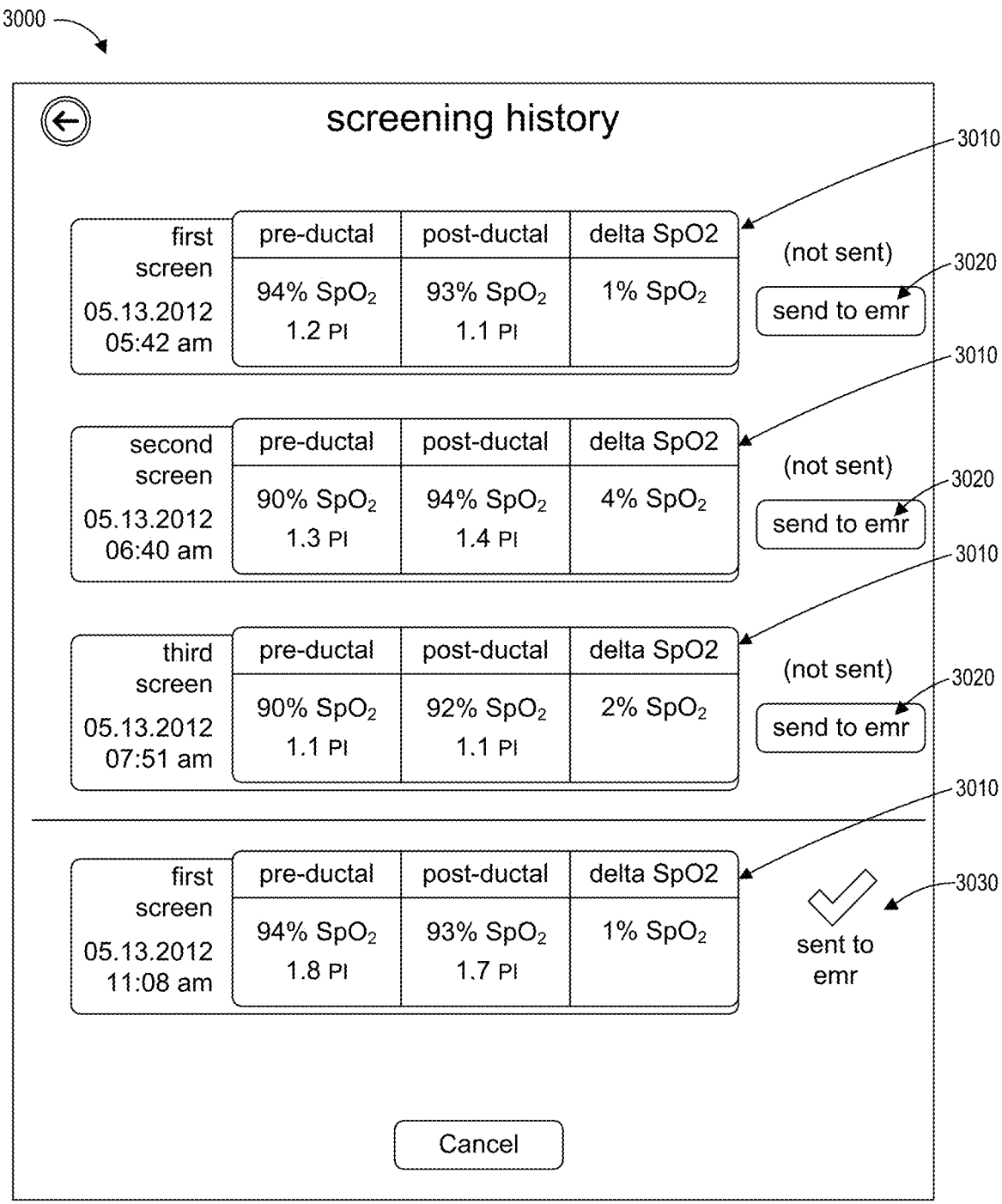
FIG. 30 illustrates an example user interface containing CCHD screening data and functionality for sending that data to an electronic medical record.

FIG. 30 depicts an example user interface 3000 for displaying a screening history of past CCHD screening results. The user interface 3000 may be generated by any of the patient devices or nurse's station systems described herein. The user interface 300 includes a plurality of entries 3010 of screening results. Each of these entries 3010 represents values obtained from CCHD screening performed previously. A user is notified to the right of the entry 3010 that some of the entries have not been sent to the EMR. Next to these entries 3010 a button 3020 is provided to send the entry to the EMR so that the data such as parameter values, time, date, etc. would be sent to the EMR for this particular patient. One of the entries 3010 includes an indication 3030 that the screening results have been sent to the EMR.

By providing the user interface 3000, the patient device or nurse's station system can advantageously provide control over what data is sent to the EMR. Some screening results may be poor results, for example, due to movement or crying of the patient. Thus, it may be undesirable to store the resulting screening data in the EMR, whereas other results may represent more valid results that may be desirable to store in the EMR.

Figure 31:
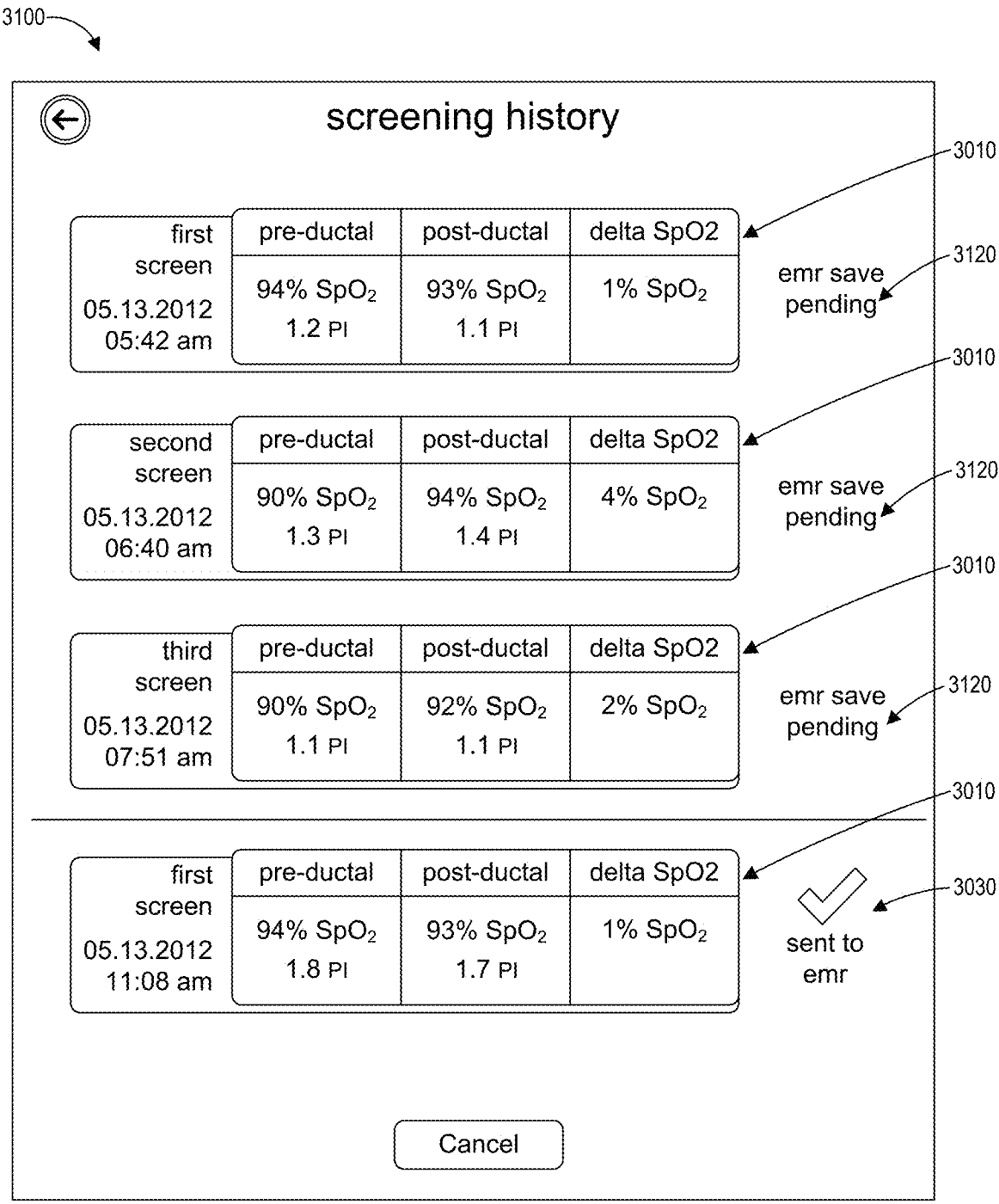
FIG. 31 illustrates an example user interface containing CCHD screening data and functionality for reporting that that data has been sent to an electronic medical record.

FIG. 31 depicts an example alternative user interface 3100 to the user interface 3000. In the user interface 3100, indicators 3120 indicate that data has been sent to the EMR and that a save of that data to the EMR is pending. An indicator 3030 indicates that one set of data has been saved to the EMR. In this embodiment, all screening data is sent to the EMR, and the user interface 3100 simply shows which data has been sent and which is in the process of being sent. This display may be modified in many ways while keeping the core concept of notifying a clinician that some data has been saved in the EMR while other data has not yet been saved in the EMR. For instance, instead of displaying the top three entries 3010, the user interface could simply display an indication that recent screening results are being saved in the EMR, or have been saved, or the like.

Figure 32:
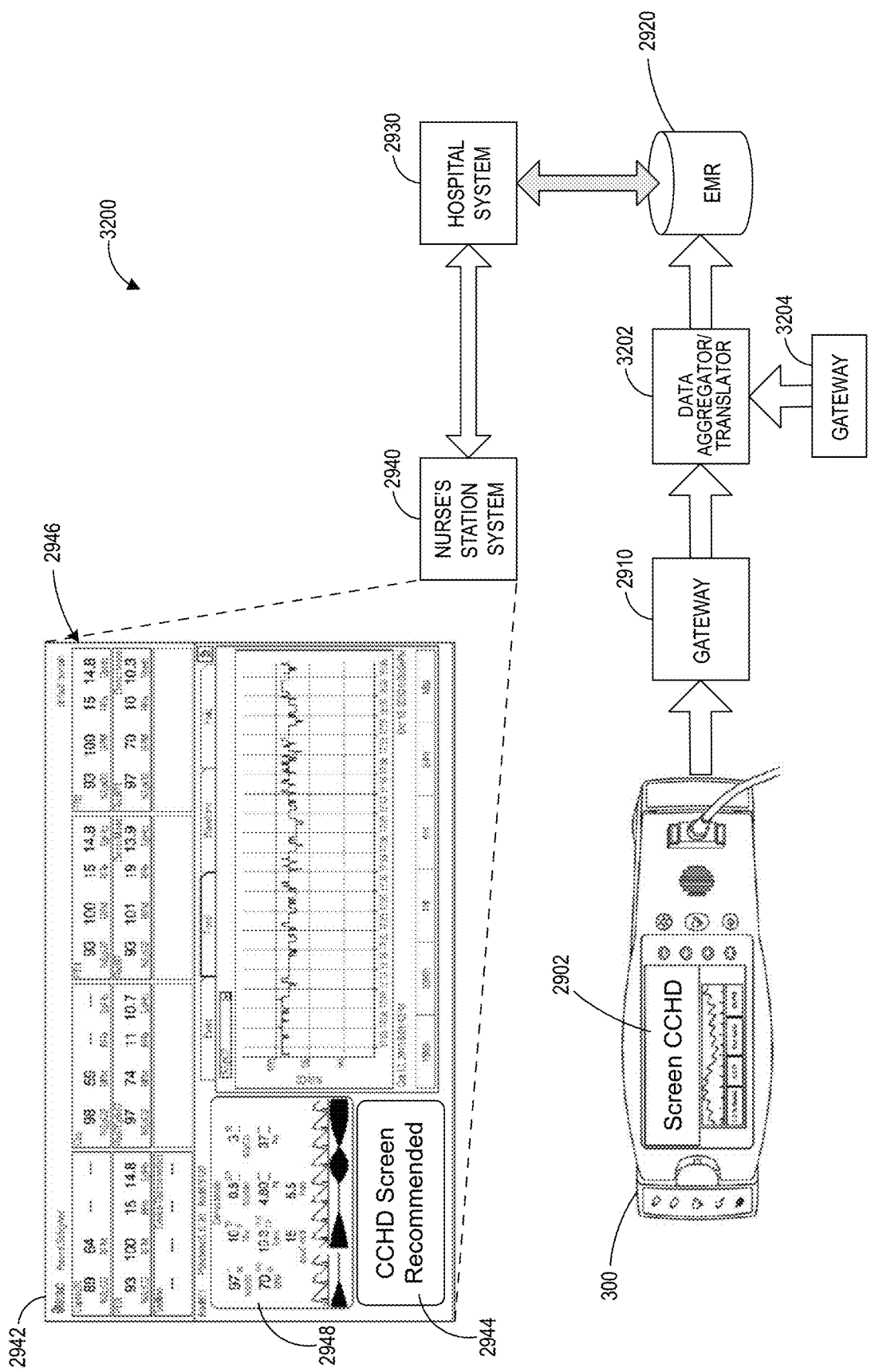
FIG. 32 illustrates another embodiment of a CCHD screening environment.

The process 2800, and other similar process as described herein, can be also used in the context of a computing environment 3200 shown in FIG. 32. The computing environment 3200 of FIG. 32 includes many of the same aspects as the computing environment 2900 described in reference to FIG. 29 above, and these aspects function similarly in the computing environment 3200. Computing environment 3200 further includes a data aggregator/translator 3202 (which may also be referred to herein simply as the "data aggregator", "data translator", "data aggregator computing device", "data translator computing device", and/or the like), which is in communication with the gateway 2910, and optionally in communication with additional gateways (e.g., gateway 3204, which represents one or more additional gateways in communication with the data aggregator/translator 3202). Communications among the various devices and systems of computing environment 3200 (e.g., patient device 300, gateway 2910, data aggregator/translator 3202, EMR 2920, hospital system 2930, nurse's stations system 2940, etc.) may be via secure communications channels, protocols, etc. In some embodiments of the computing environment 3200, each site (e.g., hospital, clinic, house, etc.) may include a gateway such as gateway 2910, and one or more patient devices (e.g. patient device 300) at the site may be in communication (either wired or wireless, or both) with the on-site gateway. The on-site gateways (e.g., gateways 2910 and 3204, which may be located at different sites) may function as generally described herein, gathering patient data (including CCHD screening results) from the patient devices, and may pass on the patient data to the data aggregator/translator 3202. The data aggregator/translator 3202 may then optionally process the patient data, and/or pass on the patient data to the EMR 2920, as further described herein.

In various implementations, the data aggregator/translator 3202 may be a server or appliance (or other appropriate computing device) that communicates with the one or more gateways and the EMR. In some implementations of the computing environment 3200, the nurse's station 2940 and/or the hospital system 2930 may be in direct communication (either wired or wireless, or both) with the on-site gateway 2910, and may thereby communicate with the EMR 2920 via the data aggregator/translator 3202 and the gateway 2910. In some implementations, as described above, the EMR 2920 may comprise any database system or data ingestion layer, such as a national database system, or the like. Further, as described above, in some implementations, the hospital system 2930 (and including the nurse's station system 2940) are optional or not included, and the patient device 300, gateway(s) 2910, data aggregator/translator 3202, and EMR 2920 function as otherwise described herein.

In the computing environment 3200, multiple on-site gateways (e.g., gateways 2910 and 3204) may each receive data from one or more patient devices at their respective sites, and may then each pass on patient data to a data aggregator/translator 3202, which may be located remotely from the sites, or in some implementations, close to one or more of the sites. In this implementation, the gateways may advantageously be lower powered (e.g., with regard to processing power, energy needs, storage needs, etc.) computing devices as compared to the data aggregator/translator 3202, as each of the gateways are only tasked with gathering and forwarding data from a relatively small number of patient devices. Advantageously, lower powered gateways are more easily and inexpensively replaceable as compared to the data aggregator/translator 3202, which may be more complex and have higher power requirements (e.g., with regard to processing power, energy needs, storage needs, etc.) so as to gather data from multiple gateways. Such an arrangement provides a significant efficiency and maintenance advantage as the gateways, which may be located in potentially remote locations, can be easily replaceable, while the data aggregator/translator 3202, which may be located in a more central location, can provide a single computing device to handle a majority of data collection and communication with the EMR 2920.

In various implementations, one or more data aggregators/translators 3202 may be geographically distributed, and each of the data aggregators/translators 3202 may communicate with a set of on-site gateways (e.g., gateways 2910 and 3204) that are located relatively near the respective one or more data aggregators/translators 3202. Each of the one or more data aggregators/translators 3202 may then communicate with the EMR 2920.

Figure 33A:
FIGS. 33A and 33B illustrate example user interfaces of a patient device.
Figure 33B:

As mentioned above, unique patient identifiers may be associated with screening data. FIGS. 33A and 33B illustrate example user interfaces for obtaining mother and/or newborn patient IDs (e.g., unique identifiers), or any other patient IDs, in association with a CCHD screening, or any other patient screening or patient data acquisition, at patient device 300. Such patient IDs may be used, at least in part, for associating CCHD screening results (and/or any other patient data) with the appropriate patients in the EMR 2920. In various implementations, the example user interfaces of FIGS. 33A and 33B may be presented on a display of patient device 300 as part of a screening workflow as described above. For example, the example user interfaces of FIGS. 33A and 33B may be presented to a user prior to the flow described above in reference to FIGS. 12A-12C. In various implementations, the patient device 300 may be configured to require input of a mother's patient ID, and newborn's patient ID, both patient IDs, or neither.

In some implementations, patient IDs may be validated by the patient device 300 (or another device in communication with the patent device 300). Validation of patient IDs may be accomplished by applying one or more validation rules or formulas to input patient IDs. Such validation rules may be provided via one or more validator files, which rules and/or files may be digitally signed such that only signed, authenticated files can be installed on the patent device 300. The validation rules may include, for example, one or more of, or any combination of: checking for correct checksum values, checking for certain digits being within allowable ranges, checking for a correct format, checking for a correct number of digits, and/or the like. In some implementations, the validation rules may be configurable (e.g., by a user or administrator), such that they may be customized per-device, per-site (e.g., for differing patient ID characteristics at different locations), and/or the like. Customization of validation rules may be accomplished via manual input at individual devices, via electronic input (e.g., download from a memory device) at individual devices, via download or configuration through a network (e.g., via a computing device communicating with multiple patient devices via a hospital network), any combination of the foregoing, and/or the like. In some implementations, the user is notified if an input patient ID does not validate. In some implementations, the user may optionally bypass a validation error (e.g., in an emergency situation). In some implementations, patient IDs may be obtained via automated functionality, such as scanning of a barcode on a patient wristband, facial recognition, or the like.

Patient data (e.g., CCHD screening results and/or any other patient data) transmitted from the patient device 300 to the gateway 2910, then to the data aggregator/translator 3202, and then to the EMR 2920, may, for example, be associated with the input patient ID(s). The patient data may further be associated with a timestamp and/or other appropriate data properties or metadata. The gateway 2910 and/or the data aggregator/translator 3202 may store (or temporarily store) and/or keep track of which items of patient data have been transmitted from the patient device 300. Such tracking may advantageously enable deduplication of patient data. For example, if the patient device transmits the same patient data multiple times (e.g., in the event of communication loss, etc.) the gateway 2910 and/or the data aggregator/translator 3202 may compare the transmitted data to a log of previously received patient data, and discard any patient data that was previously received. In another example, if the gateway 2910 transmits the same patient data multiple times (e.g., which may be stored, and/or which may be re-transmitted in the event of communication loss, etc.) the data aggregator/translator 3202 may compare the transmitted data to a log of previously received patient data, and discard any patient data that was previously received. The comparison may be based on, for example, patient ID(s), timestamps, etc. In an implementation, the comparison and deduplication of patient data is done at the data aggregator/translator 3202, rather than at the gateway 2910. In this implementation, advantageously (and as described above) the gateway may be made a simpler and lower powered computing device, that may be easily replaceable. For example, in the event of failure of the gateway, the gateway may be easily replaced without concern for loss of log data needed to perform deduplication of patient data. Rather, the replaced gateways may continue on transmitting data to the data aggregator/translator 3202, which may redundantly store a log of patient data, and perform the deduplication.

In various implementations, the data aggregator/translator 3202 may perform one or more additional processing or monitoring tasks. For example, data aggregator/translator 3202 may perform a translation of data or a format conversion from a data format used by the patient device 300 and/or the on-site gateways 2910 and 3204, to a data format recognized by the EMR 2920. In various implementations, the data translation/format conversion may be configurable, such that the data aggregator/translator 3202 may receive data in various or multiple formats, and may then output that data in various or multiple different formats. In another example, the data aggregator/translator 3202 may monitor a health or status of the on-site gateways 2910 and 3204, and may, for example, provide a notification (e.g., via EMR 2920, hospital system 2930, and/or nurse's station system 2940) if an on-site gateway is failing or has gone offline. Thus, advantageously, as a centralized device, the data aggregator/translator 3202 may be configured to report when communications with one or more gateways and/or patient devices is lost, or when patient data is no longer being received from certain sources.

Additionally, as a centralized store of patient data, including CCHD screening results from multiple sites/patient, the EMR 2920 may be used to run analyses, and generate reports, of patient data to gain insights on system-wide (e.g., across multiple sites) trends, characteristics, etc. In an implementation, a human reviewer or automated process or algorithm may determine, based on a review of patient data (e.g., at the EMR), that a re-screening for CCHD is needed. Accordingly, a message may be sent back from the EMR, through the data aggregator/translator 3202 and/or gateway 2910, and to the patient device 300 to cause the patient device 300 to indicate to a clinician that a re-screening is needed. In another implementation, the message may be provided to the nurse's station system 2940, or other appropriate device or system to notify a clinician to re-screen a patient for CCHD. In various implementations, other information may be transmitted back from the EMR to the data aggregator/translator, gateway, and/or patient device, e.g., status information, error information, success information, etc.

Figure 34:
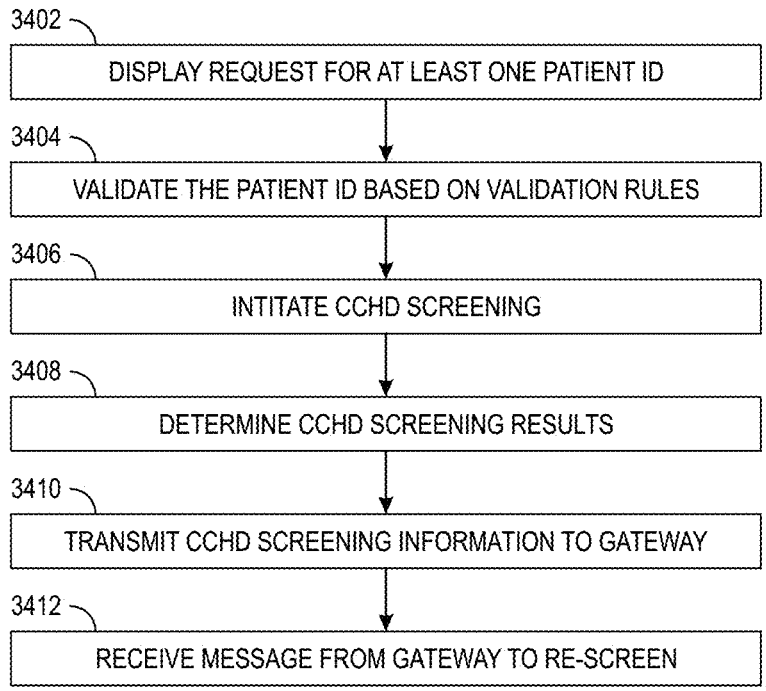
FIG. 34 illustrates an embodiment of a CCHD screening process.

FIG. 34 illustrates an example CCHD screening process. Like the processes 1900 and 2800 described above, the screening process may be implemented by any of the patient devices or electronic devices described herein, including by devices described above with respect to FIGS. 29 and 32. In various implementations, the screening process of FIG. 34 may be re-ordered and/or combined with other screening processes described herein. Further, various blocks of the screening process of FIG. 34 may be optional.

At block 3402, one or more user interfaces (e.g., similar to the example user interfaces of FIGS. 33A-33B) are provided to the user requesting input of one or more patient IDs. At block 3404, the patient IDs may be validated, as described above. At block 3406, a CCHD screening workflow may be initiated, as described in reference to various Figures herein (e.g., FIGS. 12A-12C, 13A-13C, 14A-14D, and/or 28), and at block 3408, CCHD screening results may be determined, as described in detail in reference to various implementations and embodiments herein.

At block 3410, the CCHD screening information, including the CCHD screening results, associated patient ID(s), and other related information, is communicated to the gateway (e.g., gateway 2910). The gateway then communicates the information to the data aggregator (e.g., data aggregator 3202), where the information may be processed and then communicated to the EMR. In general, the information transmitted among the various patient devices, gateways, and data aggregators/translators, may referred to as "patient data" and/or the like, and may include one or more of the various types of information described in the present application.

At optional block 3412, the patient device may receive a message (e.g., via the data aggregator/translator and gateway) to re-screen the patient for CCHD, in response to which the patient device may display a notification to a clinician to initiate a re-screening. In various implementations, other information may be received by the patient device, e.g., status information, error information, success information, etc.

Figure 35:
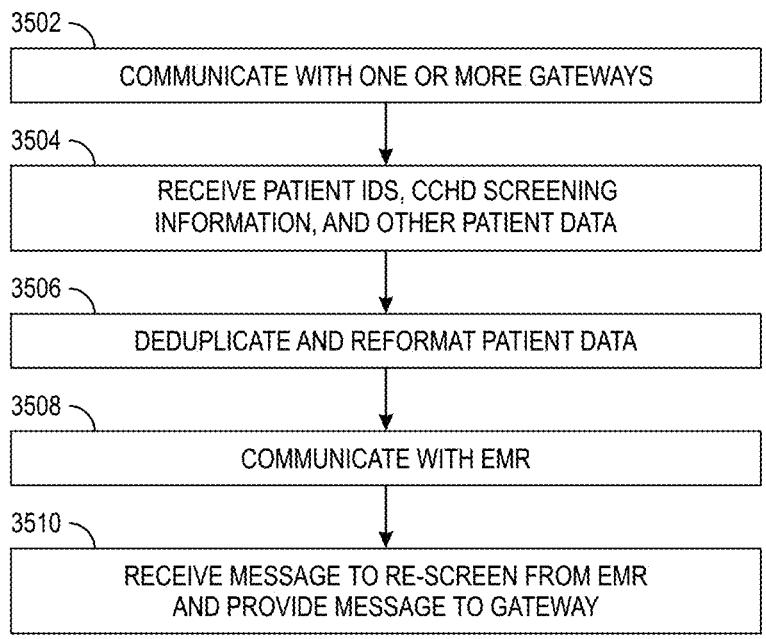
FIG. 35 illustrates an embodiment of a data handling process.

FIG. 35 illustrates an example data handling process that may be implemented by the data aggregator/translator 3202. In various implementations, the process of FIG. 35 may be re-ordered and/or combined with other processes described herein. Further, various blocks of the process of FIG. 35 may be optional.

At block 3502, the data aggregator/translator 3202 is in communication with one or more gateway devices, as generally described above. Communication may be via any suitable electronic communications method or protocol, including wired or wireless, via one or more networks, via the Internet, and/or the like.

At block 3504, the data aggregator/translator 3202 receives patient data from a gateway device (which may have been received by the gateway device from one or more patient devices), which patient data may include CCHD screening information and associated patient IDs. At block 3506, the data aggregator/translator 3202 may optionally de-duplicate the patient data, as generally described above. For example, if, based on log data, the data aggregator/translator 3202 determines that the received patient data was previously received (e.g., in the event that it is re-transmitted to the data aggregator/translator 3202 from a gateway as a result of an error in the gateway or temporary loss of communication), the received patient data may be discarded. The data aggregator/translator 3202 may also optionally re-format the patient data as appropriate for communication to the EMR.

At block 3508, the patient data is communicated to the EMR. At optional block 3510, the data aggregator/translator 3202 may receive a message to re-screen from the EMR. The message may be associated with one or more patient IDs. The message may further include an identification of the relevant patient device to which the message is to be communicated, or alternatively the data aggregator/translator 3202 may determine the relevant patient device. The data aggregator/translator 3202 may then communicate the message to the relevant patient device. In various implementations, other information may be received by the data aggregator/translator and/or the gateway, e.g., status information, error information, success information, etc.

In various implementations, other types of patient data (besides CCHD screening information) may be communicated and processed via the various systems and processes described herein. As noted above, in various implementations, communications among the various devices and systems described herein, e.g., patient device 300, gateway 2910, data aggregator/translator 3202, EMR 2920, hospital system 2930, nurse's stations system 2940, etc., may be via secure communications channels, protocols, etc.

Accordingly, the data aggregator/translator 3202 and/or the gateways 2910, 3204 may be computing systems or devices including memory/storage and one or more processing devices configured to execute computer executable program instructions.

Terminology

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While certain embodiments of the inventions disclosed herein have been described, these embodiments have been presented by way of example only, and are not intended to limit the scope of the inventions disclosed herein. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein.

What is claimed is:

1. A system for noninvasively measuring a physiological parameter of a user to facilitate a diagnosis, the system comprising:
   an electronic device comprising a display, a wireless transceiver, a memory device comprising processor-executable instructions stored thereon, and one or more hardware processors in communication with the display, the wireless transceiver, and the memory device;
   the one or more hardware processors programmed to execute the processor-executable instructions stored in the memory device to:
      display, on the display, a request for at least one patient ID associated with a user;
      receive an input including the at least one patient ID;
      validate the at least one patient ID using one or more validation rules, wherein the one or more validation rules comprise at least one of: checking for correct checksum values, checking for certain digits being within allowable ranges, or checking for a correct format;
      display, on the display, instructions to obtain a first measurement by positioning a first noninvasive sensor at a first measurement site on the user;
      receive, from the first noninvasive sensor, first signals responsive to a first physiological characteristic of the user;
      calculate a first measured physiological parameter responsive to the first signals;
      display, on the display, instructions to obtain a second measurement by positioning a second noninvasive sensor at a second measurement site on the user;
      receive, from the second noninvasive sensor, second signals responsive to a second physiological characteristic of the user;
      calculate a second measured physiological parameter of the user responsive to the second signals;
      display, on the display, the first and second measured physiological parameters;
      transmit, via the wireless transceiver, at least the first and second measured physiological parameters, in association with the at least one patient ID, over a network to a clinician; and
      initiate, with the wireless transceiver, a telemedicine session with the clinician over the network to obtain a diagnosis based on the first and second measured physiological parameters.

2. The system of claim 1, wherein the first and second noninvasive sensors are the same noninvasive sensor.

3. The system of claim 1, wherein the one or more hardware processors are programmed to execute the processor-executable instructions stored in the memory device to further:
   in response to determining that the at least one patient ID is not valid:
      provide a notification to the user; and
      allow the user to bypass the notification and proceed with measurements despite determining that the at least one patient ID is not valid.

4. The system of claim 1, wherein the first or second measured physiological parameters include at least one of: oxygen saturation, blood pressure, or temperature.

5. The system of claim 1, wherein at least the first and second measured physiological parameters, are transmitted, in association with the at least one patient ID, to a data aggregator computing device.

6. The system of claim 5, wherein the one or more hardware processors are programmed to execute the processor-executable instructions stored in the memory device to further:
   in response to receiving a message indicating a need to re-screen a user, display a notification.

7. The system of claim 6, wherein the message is received via the data aggregator computing device, and wherein the data aggregator computing device determines the message is to be provided to the system.

8. The system of claim 5, wherein the data aggregator computing device is configured to de-duplicate patient data.

9. The system of claim 8, wherein the data aggregator computing device is configured to transmit at least the first and second measured physiological parameters in association with the at least one patient ID to an electronic medical record (EMR) system or other database system.

10. The system of claim 9, wherein the data aggregator computing device is further configured to aggregate patient data from a plurality of computing devices.

11. The system of claim 1, wherein the one or more hardware processors are programmed to execute the processor-executable instructions stored in the memory device to further:
    output a selection of clinicians, receive a selection of one of the clinicians from the user, and initiate a communication session with the clinician.

12. The system of claim 1, wherein the telemedicine session comprises a video of the clinician.

13. The system of claim 1, wherein the one or more hardware processors are programmed to execute the processor-executable instructions stored in the memory device to further:
    instruct the user to perform at least one of the first measurement or the second measurement again due to low signal confidence in the at least one of the first measurement or the second measurement.

14. A computer-implemented method for noninvasively measuring a physiological parameter of a user to facilitate a diagnosis, the method comprising:
    by one or more processors executing program instructions:
       displaying, on display, a request for at least one patient ID associated with a user;
       receiving an input including the at least one patient ID;
       validating the at least one patient ID using one or more validation rules, wherein the one or more validation rules comprise at least one of: checking for correct checksum values, checking for certain digits being within allowable ranges, or checking for a correct format;
       displaying, on the display, instructions to obtain a first measurement by positioning a first noninvasive sensor at a first measurement site on the user;
       receiving, from the first noninvasive sensor, first signals responsive to a first physiological characteristic of the user;
       calculating a first measured physiological parameter responsive to the first signals;

displaying, on the display, instructions to obtain a second measurement by positioning a second noninvasive sensor at a second measurement site on the user;

receiving, from the second noninvasive sensor, second signals responsive to a second physiological characteristic of the user;

calculating a second measured physiological parameter of the user responsive to the second signals;

displaying, on the display, the first and second measured physiological parameters;

transmitting, via a wireless transceiver, at least the first and second measured physiological parameters, in association with the at least one patient ID, over a network to a clinician; and initiating, with the wireless transceiver, a telemedicine session with the clinician over the network to obtain a diagnosis based on the first and second measured physiological parameters.

15. The computer-implemented method of claim 14, wherein the first and second noninvasive sensors are the same noninvasive sensor.

16. The computer-implemented method of claim 14 further comprising:
by the one or more processors executing program instructions:
in response to receiving a message indicating a need to re-screen a user, displaying a notification.

17. The computer-implemented method of claim 16, wherein:
at least the first and second measured physiological parameters, are transmitted, in association with the at least one patient ID, to a data aggregator computing device,
the message is received via the data aggregator computing device, and
the data aggregator computing device determines the message is to be provided for display.

18. The computer-implemented method of claim 14 further comprising:
by the one or more processors executing program instructions:
outputting a selection of clinicians, receive a selection of one of the clinicians from the user, and initiate a communication session with the clinician.

19. The computer-implemented method of claim 14, wherein the telemedicine session comprises a video of the clinician.

20. The computer-implemented method of claim 14 further comprising:
by the one or more processors executing program instructions:
instructing the user to perform at least one of the first measurement or the second measurement again due to low signal confidence in the at least one of the first measurement or the second measurement.

* * * * *